(12) United States Patent
Margiott et al.

(10) Patent No.: US 12,721,554 B2
(45) Date of Patent: Sep. 1, 2026

(54) HANDHELD OXIMETER WITH DISPLAY OF REAL-TIME, AVERAGE MEASUREMENTS AND STATUS INDICATOR

(71) Applicant: ViOptix, Inc., Newark, CA (US)

(72) Inventors: Alex Michael Margiott, Dunbarton, NH (US); William Welch, Sunnyvale, CA (US); Sushant Potdar, Fremont, CA (US); Scott E. Coleridge, New York, NY (US)

(73) Assignee: ViOptix, Inc., Newark, CA (US)

( * ) Notice: Subject to any disclaimer, the term of this patent is extended or adjusted under 35 U.S.C. 154(b) by 826 days.

(21) Appl. No.: 18/047,627

(22) Filed: Oct. 18, 2022

(65) Prior Publication Data

US 2023/0225638 A1 Jul. 20, 2023

Related U.S. Application Data

(60) Provisional application No. 63/262,680, filed on Oct. 18, 2021.

(51) Int. Cl.
*A61B 5/1455* (2006.01)
*A61B 5/00* (2006.01)
*A61B 5/1459* (2006.01)

(52) U.S. Cl.
CPC ........ *A61B 5/14552* (2013.01); *A61B 5/7221* (2013.01); *A61B 5/7246* (2013.01); *A61B 5/7278* (2013.01); *A61B 5/742* (2013.01); *A61B 5/743* (2013.01); *A61B 5/7445* (2013.01); *A61B 5/7475* (2013.01); *A61B 5/1459* (2013.01); *A61B 2560/0431* (2013.01);
(Continued)

(58) Field of Classification Search
CPC .................................................... A61B 5/1455
See application file for complete search history.

(56) References Cited

U.S. PATENT DOCUMENTS 6,516,209 B2 2/2003 Cheng et al.
6,587,703 B2 7/2003 Cheng et al.
6,597,931 B1 7/2003 Cheng et al.
(Continued)

FOREIGN PATENT DOCUMENTS

EP 1006863 B1 6/2000
WO 2014/026200 A1 2/2014

OTHER PUBLICATIONS

Extended European Search Report for European patent application 22884380.1 dated Jun. 4, 2025, 9 pages.
(Continued)

*Primary Examiner* — Marjan Fardanesh
(74) *Attorney, Agent, or Firm* — Aka Chan LLP

(57) ABSTRACT

An oximetry device sealed in a sheath directs a user to allow the oximetry device to make oximetry readings at a number of different tissue locations of a patient and average two or more of the oximetry readings by directing the lifts and placements of the oximetry device and sheath to and from the different tissue locations and detecting the lift and placements. The averages are generated and displayed on a display of the device for the oximetry readings if the lifts are made while use directions for the lifts are displayed on a display of the oximetry device. The averages are not generated if the lifts are not made while the user directions for the lifts are not displayed. The averages are simultaneously displayed with the oximetry readings which are instantaneous measurement for patient tissue.

18 Claims, 33 Drawing Sheets

(52) U.S. Cl.
CPC ................. *A61B 2560/0475* (2013.01); *A61B 2562/0219* (2013.01); *A61B 2562/166* (2013.01); *A61B 2562/18* (2013.01)

(56) References Cited

U.S. PATENT DOCUMENTS

| | | | |
|---|---|---|---|
| 6,735,458 | B2 | 5/2004 | Cheng et al. |
| 6,801,648 | B2 | 10/2004 | Cheng |
| 7,247,142 | B1 | 7/2007 | Elmandjra et al. |
| 9,186,112 | B2 | 11/2015 | Bechtel et al. |
| 9,216,000 | B2 | 12/2015 | Bechtel et al. |
| 9,345,439 | B2 | 5/2016 | Bechtel et al. |
| 9,392,978 | B2 | 7/2016 | Bechtel et al. |
| 9,398,870 | B2 | 7/2016 | Bechtel et al. |
| 9,498,157 | B2 | 11/2016 | Bechtel et al. |
| 10,575,763 | B2 | 3/2020 | Bechtel et al. |
| 10,722,156 | B2 | 7/2020 | Lonsinger et al. |
| 10,722,158 | B2 | 7/2020 | Heanue et al. |
| 10,750,986 | B2 | 8/2020 | Bechtel et al. |
| 10,786,187 | B2 | 9/2020 | Bechtel et al. |
| 10,820,863 | B2 | 11/2020 | Bechtel et al. |
| 10,827,957 | B2 | 11/2020 | Bechtel et al. |
| 10,849,536 | B2 | 12/2020 | Bechtel et al. |
| 10,932,708 | B2 | 3/2021 | Bechtel et al. |
| 11,439,330 | B2 | 9/2022 | Bechtel et al. |
| 2021/0007649 | A1 | 1/2021 | Bechtel et al. |
| 2021/0212583 | A1 | 7/2021 | Kmak et al. |
| 2021/0212584 | A1 | 7/2021 | Margiott et al. |
| 2021/0212610 | A1 | 7/2021 | Margiott et al. |
| 2021/0212612 | A1 | 7/2021 | Hohl et al. |
| 2021/0212613 | A1 | 7/2021 | Margiott et al. |
| 2021/0212614 | A1 | 7/2021 | Kmak et al. |
| 2021/0212615 | A1 | 7/2021 | Bechtel et al. |

OTHER PUBLICATIONS

International Search Report and the Written Opinion of the International Searching Authority for International Application No. PCT/US2022/047062 dated Sep. 14, 2023, 15 pages.

HANDHELD OXIMETER WITH DISPLAY OF REAL-TIME, AVERAGE MEASUREMENTS AND STATUS INDICATOR

CROSS-REFERENCE TO RELATED APPLICATIONS

This patent application claims the benefit of U.S. patent application 63/262,680, filed Oct. 18, 2021. This application is incorporated by reference along with all other references cited in this application.

BACKGROUND OF THE INVENTION

This invention relates generally to optical systems that monitor parameters related to oxygen levels in tissue. More and sheaths for the optical probes that shield the optical probes from contaminants during use and specifically, the present invention relates to optical probes, such as compact, handheld oximeters, communicate status information to the optical probes regarding contaminant protection so that the optical probes are reusable.

Oximeters are medical devices used to measure the oxygen saturation of tissue in humans and living things for various purposes. For example, oximeters are used for medical and diagnostic purposes in hospitals and other medical facilities (e.g., operating rooms for surgery, recovery room for patient monitoring, or ambulance or other mobile monitoring for, e.g., hypoxia); sports and athletic purposes at a sports arena (e.g., professional athlete monitoring); personal or at-home monitoring of individuals (e.g., general health monitoring, or person training for a marathon); and veterinary purposes (e.g., animal monitoring).

In particular, assessing a patient's oxygen saturation, at both the regional and local levels, is important as it is an indicator of the state of the patient's health. Thus, oximeters are often used in clinical settings, such as during surgery and recovery, where it can be suspected that the patient's tissue oxygenation state is unstable. For example, during surgery, oximeters should be able to quickly deliver accurate oxygen saturation measurements under a variety of non-ideal conditions.

Pulse oximeters and tissue oximeters are two types of oximeters that operate on different principles. A pulse oximeter requires a pulse in order to function. A pulse oximeter typically measures the absorbance of light due to pulsing arterial blood. In contrast, a tissue oximeter does not require a pulse in order to function, and can be used to make oxygen saturation measurements of a tissue flap that has been disconnected from a blood supply.

Human tissue, as an example, includes a variety of light-absorbing molecules. Such chromophores include oxygenated hemoglobin, deoxygenated hemoglobin, melanin, water, lipid, and cytochrome. Oxygenated and deoxygenated hemoglobins are the dominant chromophores in tissue for much of the visible and near-infrared spectral range. Light absorption differs significantly for oxygenated and deoxygenated hemoglobins at certain wavelengths of light. Tissue oximeters can measure oxygen levels in human tissue by exploiting these light-absorption differences.

Despite the success of existing oximeters, there is a continuing desire to improve oximeters by, for example, improving the reuse of oximeters; reducing or eliminating contamination during use; improving remote communication; improving measurement accuracy; reducing measurement time; lowering cost through reuse; reducing size, weight, or form factor; reducing power consumption; and for other reasons, and any combination of these.

Therefore, there is a need for improved tissue oximetry devices and methods of shielding oximetry devices during use for reuse of the devices.

BRIEF SUMMARY OF THE INVENTION

Embodiments relate to a compact, handheld oximeter and measurement averaging of oximetry readings performed by the handheld oximeter. The average measurement and real-time oximetry readings can be displayed on a display of the oximeter to provide medical professionals with valuable oximetry information useful for diagnosing an oximetry state of patient tissue.

In an implementation, an oximetry device is sealed in a sheath where a user can contact the sheath to a number of different tissue locations to allow the oximetry device to make oximetry measurements of the tissue. The oximetry device averages two or more of the oximetry readings by detecting the sheath being placed in contact with the tissue locations and being lifted from contact from the tissue locations. The average is generated and displayed on a display of the oximetry device for the oximetry readings if the lifts are made while use directions for the lifts are displayed on a display of the oximetry device. The averages are not generated if the lifts are not made while the user directions for the lifts are not displayed. The averages are simultaneously displayed with the oximetry readings which are instantaneous measurement for patient tissue. The averaging allows a user of the oximetry device to monitor the oximetry information as an average as tissue conditions of the tissue change during a surgery. Being able to monitor how the average value changes over time by viewing the average displayed on the display allows the user to obtain a history of the tissue during the surgery to perform more successful surgeries, such as tissue flap surgeries where real-time and average oximetry information of a tissue flap allows for the flap to be trimmed or not trimmed based on the real-time and average information for more successful flap grafting.

Other objects, features, and advantages of the present invention will become apparent upon consideration of the following detailed description and the accompanying drawings, in which like reference designations represent like features throughout the figures.

DETAILED DESCRIPTION OF THE INVENTION

Figure 1:
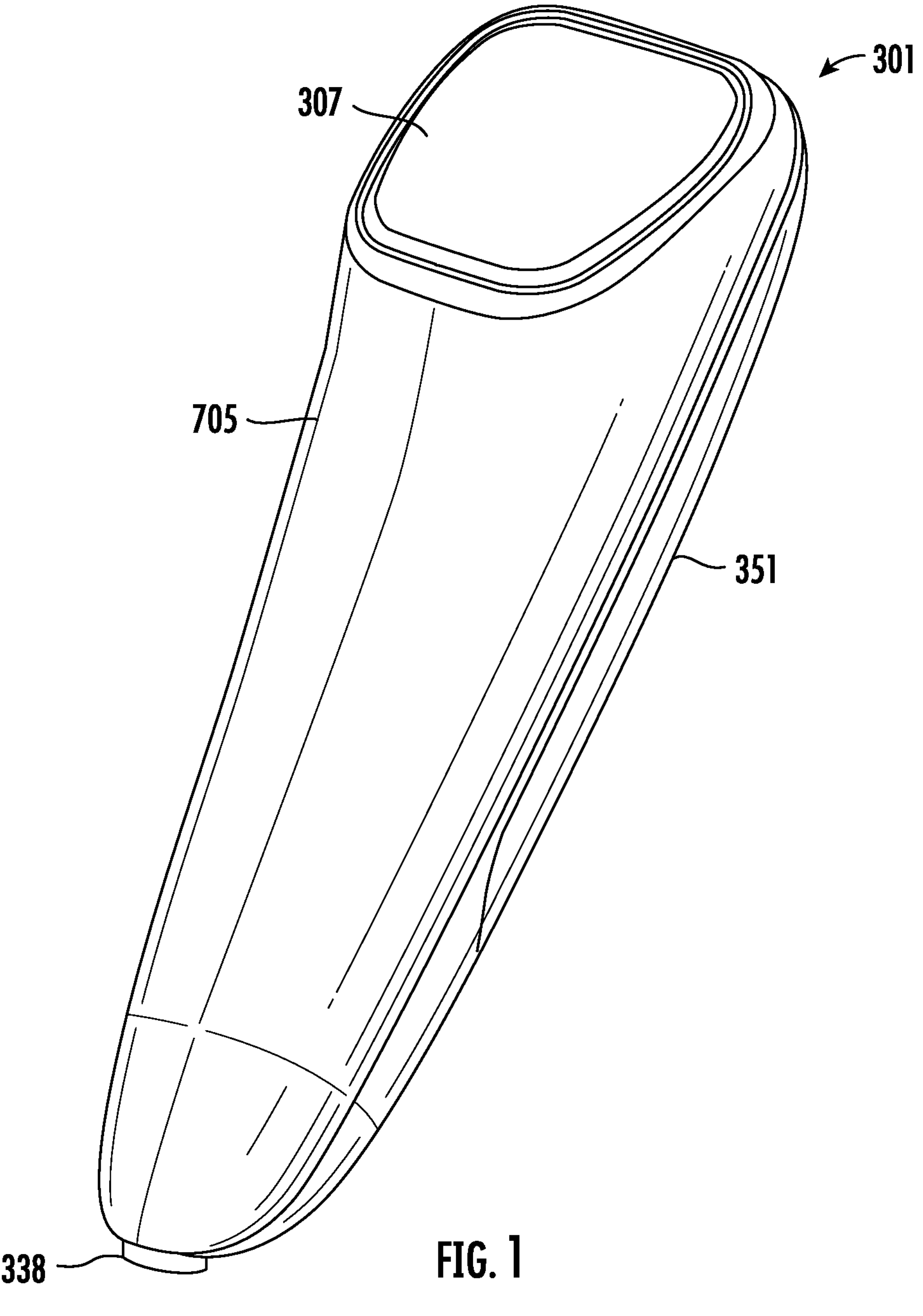
FIG. 1 shows a perspective view of a system unit for measuring various oximetry parameters of patient tissue where the system unit can be an oximeter.

Spectroscopy has been used for noninvasive measurements of various physiological properties in animal and human subjects. Visible (e.g., red light) and near-infrared spectroscopy is often utilized because physiological tissues have relatively low scattering in these spectral ranges. Human tissues, for example, include numerous light-absorbing chromophores, such as oxygenated hemoglobin, deoxygenated hemoglobin, melanin, water, lipid, and cytochrome. The hemoglobins are the dominant chromophores in tissue for much of the visible and near-infrared spectral range and via light absorption, contribute to the color of human tissues. In the visible and near-infrared range, oxygenated and deoxygenated hemoglobins have significantly different absorption features. Accordingly, visible and near-infrared spectroscopy has been applied to exploit these different absorption features for measuring oxygen levels in physiological media, such as tissue hemoglobin oxygen saturation (sometimes referred to as oxygen saturation) and total hemoglobin concentrations.

Spatially-resolved spectroscopy (SRS) is one type of visible and near-infrared spectroscopy that allows tissue absorption to be determined independently from tissue scattering, thereby allowing absolute measurements of chromophore concentrations, such as oxygenated and deoxygenated hemoglobins. More specifically, an SRS instrument may emit light into tissue through a light source and collect the diffusely reflected light at two or more detectors positioned at different distances from the light source.

One field in which visible and near-infrared spectroscopy, such as SRS, is useful in tissue flap surgery in which a tissue flap is moved from one location on a patient to another location for reconstructive surgery. Visible and near-infrared spectroscopy techniques can be used to measure oxygen saturation in a tissue flap so that the viability of the tissue flap can be determined in surgery and after surgery. Intraoperative tissue flap oximetry probes that employ visible and near-infrared SRS should be able to quickly deliver accurate oxygen saturation measurements under a variety of non-ideal conditions.

The following patent applications are incorporated by reference along with all other references cited in this application: U.S. patent application Ser. Nos. 13/887,130, 13/887,178, 13/887,213, and 13/887,220, filed May 3, 2013; Ser. No. 13/965,156, filed Aug. 12, 2013; Ser. No. 13/887,152, filed May 3, 2013; Ser. Nos. 15/493,111, 15/493,121, and 15/493,132, Apr. 20, 2017; Ser. No. 15/493,444, filed Apr. 21, 2017; Ser. Nos. 15/495,194, 15/495,205, and 15/495,212, filed Apr. 24, 2017; Ser. No. 15/652,201, filed Jul. 17, 2017; Ser. Nos. 15/652,638 and 15/652,929, filed Jul. 18, 2017; Ser. Nos. 17/146,176, 17/146,182, 17/146,186, 17/146,190, 17/146,194, 17/146,197, and 17/146,201, filed Jan. 11, 2021. The implementations, embodiments, features, aspects, concepts, and ideas described in this patent can be combined with one or more implementations, embodiments, features, aspects, concepts, or ideas described in these references as well as other systems and techniques described elsewhere, in any order or combination.

This patent describes some examples of implementations with specific dimensions, measurements, temperatures, values, percentages, and times. These are not intended to be exhaustive or to limit the invention to the precise form described. The specific dimensions, measurements, temperatures, values, percentages, and times are approximate values. These values can vary due to, for example, measurement or manufacturing variations or tolerances or other factors. For example, depending on the tightness of the manufacturing and measurement tolerances, the temperature and time values can vary plus or minus 2 percent, 2.5 percent, plus or minus 5 percent, plus or minus 7.5 percent, plus or minus 10 percent, plus or minus 12.5 percent, plus or minus 15 percent, plus or minus 20 percent, or plus or minus 25 percent, or other ranges.

Further, the values are for a specific implementation, and other implementations can have different values, such as certain values made larger for a larger-scaled sized process or product, or smaller for a smaller-scaled process or product. A device, apparatus, or process may be made proportionally larger or smaller by adjusting relative measurements proportionally (e.g., maintaining the same or about the same ratio between different measurements). In various implementations, the values can be the same as the value given, about the same of the value given, at least or greater than the value given, or can be at most or less than the value given, or any combination of these.

Some flow implementations are presented in this patent, but it should be understood that the invention is not limited to the specific flows and steps presented. A flow may have additional steps (not necessarily described in this application), different steps which replace some of the steps presented, fewer steps or a subset of the steps presented, or steps in a different order than presented, or any combination of these. Further, the steps in other implementations may not be exactly the same as the steps presented and may be modified or altered as appropriate for a particular application or based on the data.

An implementation of the invention includes a probe, such as the described system unit or laparoscopic oximeter, and accompanying techniques to calculate and display an average oxygen saturation measurement of a number of previous measurements. The average measurement can be reset by the user by making a gesture with the probe. An example of a gesture is inverting the probe, relative to its standard operating orientation. And then after returning the probe to its standard operating orientation, the average value will be reset or initialized, and calculating of the average value will start at a count of 1. The instantaneous or instant oxygen saturation value can be displayed on the same screen as the average value, so that the user will be able to compare the oxygen saturation value with the average value of previous oxygen saturation measurements.

An accelerometer integrated circuit or chip is used to detect gestures or motion of the probe. The probe can be an oximeter, such as a tissue oximeter or pulse oximeter, which makes oxygen saturation measurements. The probe can be a standalone probe, where the unit is self contained, and the oxygen saturation measurements and calculations to determine these measurements and the average values are contained within an enclosure of the standalone probe. Some components of the standalone probe include a processor, memory, display, signal emitters, light detectors, batteries (e.g., disposable or rechargeable), accelerometer, and others.

In other implementations, the probe can be a connected wirelessly (e.g., Bluetooth or Wi-Fi) or wired to another device or unit (e.g., system unit, smartphone, or display console, or combination) or a number of devices or units, or to the cloud via a network or the Internet. The components and calculations can be divided among the connected devices or the cloud. For example, data from the probe can be transmitted to another device for determine of the oxygen saturation value and average saturation value, and then these value can be displayed on a screen separate from the probe. In such implementations, the components resident on the probe can be, for example, signal emitters, light detectors, the accelerometer (to detect gestures), and wireless or wired interface circuits; the processor and memory can be external to the probe. By removing some of the components, this would reduce the size and power consumption of the probe.

Various data structures can be used to implement the oxygen saturation averaging feature. In an implementation, there is a first memory location to accumulate a sum of the previous instant oxygen saturation measurements and a second memory location to keep a count of the number of measurements made. The second memory location may be referred to as a counter. The second memory location can have a maximum value, and if the maximum value is achieved, then no further measurements will be added to the first memory location. And the average displayed on the screen will no longer change or update, even when further instant oxygen saturation measurement are made and displayed.

Other data structures may be used to implement the oxygen saturation averaging feature, and more specifically a rolling or continuous moving average. For example, the instant oxygen saturation measurements may be stored in a queue data structure (e.g., implemented using an array or linked list structure). There can be a first memory location to keep a sum of the values in the queue, or the sum can be calculated by an arithmetic logic unit each time an average is desired. And another memory location will keep a count of the number of entries in the queue. The count may have a maximum value. And when that is achieved, the first oxygen saturation added to the queue will be removed (first-in, first-out or FIFO operation) and its value subtracted from sum memory location. The values in the queue will be moved back one location in the queue. And a current instant oxygen saturation measurement is added at an end of the queue. Other data structures and techniques can be used to implement a moving or rolling average.

Figure 2:
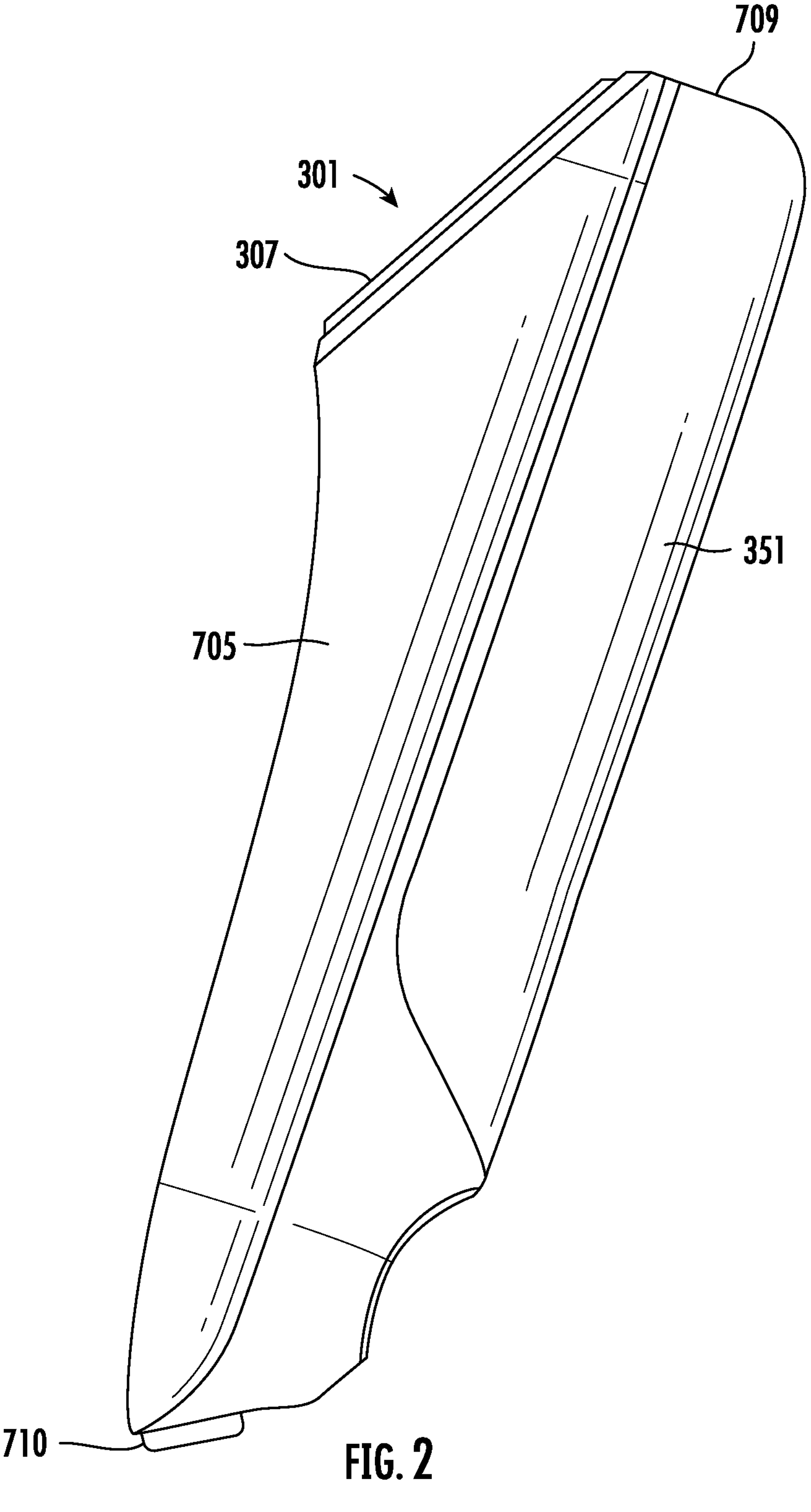
FIG. 2 shows a side view of the system unit.

FIGS. 1 and 2 show a perspective view and a side view of a system unit 301 and power block 351 coupled to the system unit, in an implementation. System unit 301 can be a tissue oximeter. In another implementation, system unit 301 can be a pulse oximeter. The system unit includes a display 307 at a first end of a housing 705 on which oximetry information can be displayed by the system unit. The system unit can include one or more light sources, one or more detectors, one or more memories (e.g., flash memory or RAM), a processor for controlling the light sources and detectors, and a battery for providing power to the light sources, detector, memories, processor, and display. The processor can control the system unit to make oximetry readings of tissue.

FIG. 2 shows a side view of system unit 301, in an implementation. The housing 705 of the system unit includes a bezel 710 that houses a portion of the probe tip. The bezel includes an opening the exposes a probe face of the probe tip.

Figure 3:
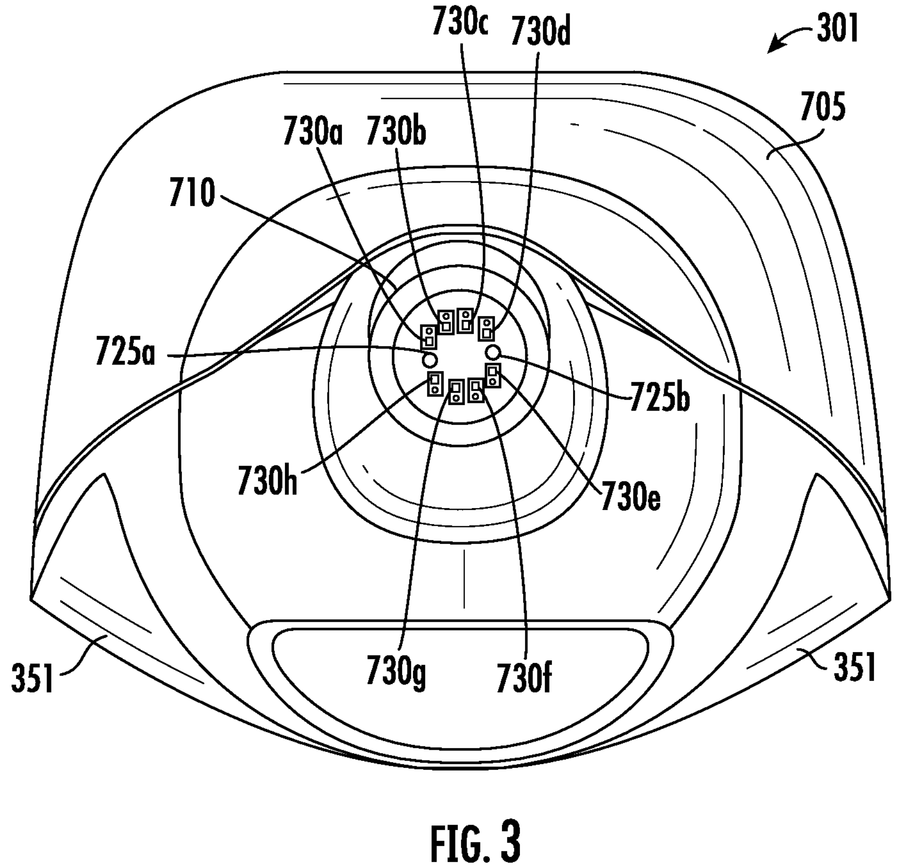
FIG. 3 shows an end view of a sensor head end of the system unit, in an implementation.

FIG. 3 shows an end view of a second end of the housing and system unit, in an implementation. The first and second ends of the system unit are located at opposite ends of the unit. The end of bezel 710 is shown with the probe face 715 in the opening of the bezel. The probe face may include an aperture plate 720 that includes a number of source apertures, for example, source apertures 725*a* and 725*b*, and includes a number of detector apertures, such as apertures 730*a*-730*h*. Each of the source apertures may be included in a source structure that may include light sources, such as one or more optical fibers, laser diodes, LEDs, one or more portions of the aperture plate, or other structures at the probe tip in any combination. Each of the detector apertures may be included in a detector structure that may include light detectors, such as one or more optical fibers, photodetectors, one or more portions of the aperture plate, or other structures at the probe tip in any combination.

Figure 4:
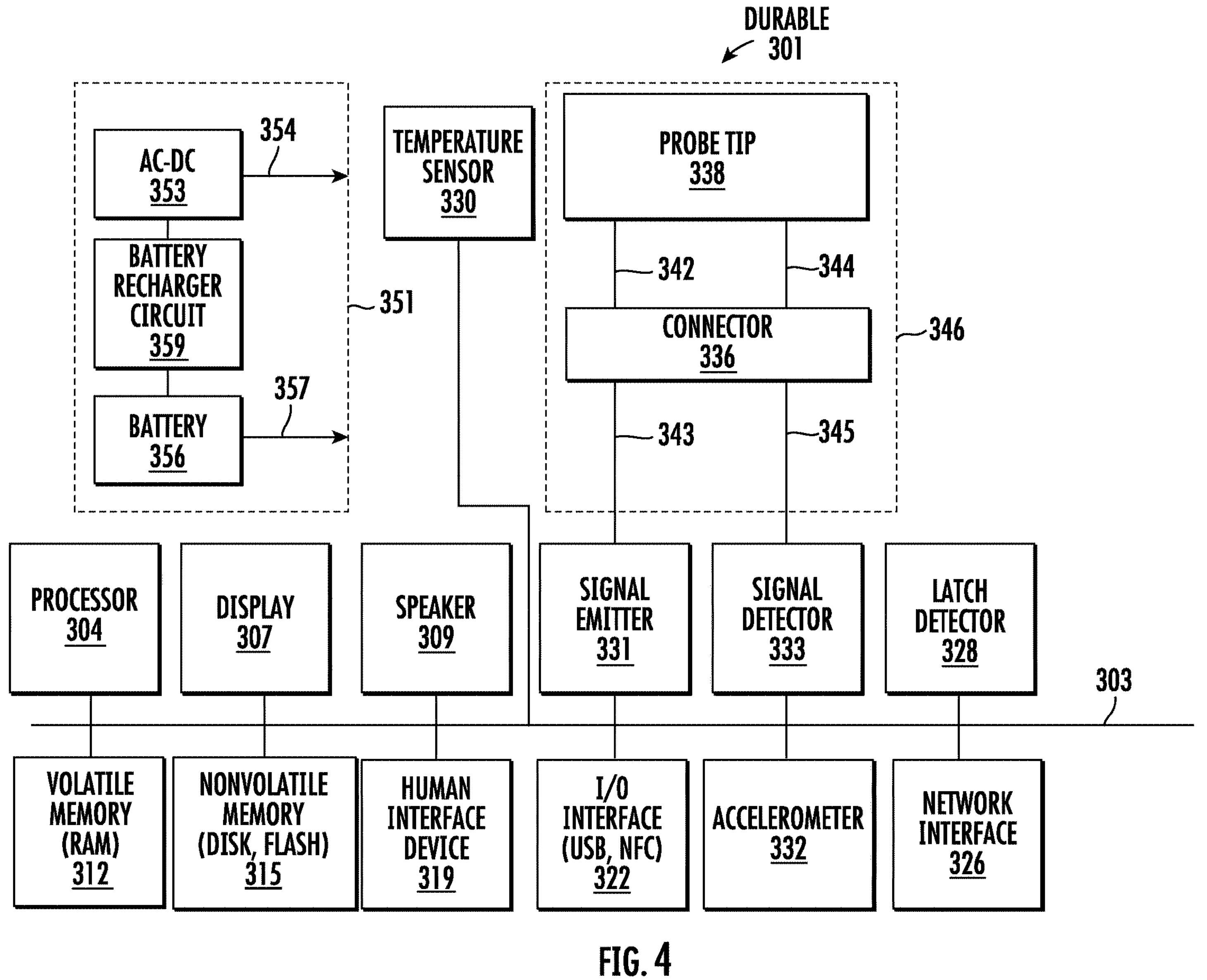
FIG. 4 shows a block diagram of the system unit, in an implementation.

FIG. 4 shows a block diagram of system unit 301, in an implementation. The system unit includes a processor 304, display 307, speaker 309, signal emitter 331, signal detector 333, volatile memory 312, nonvolatile memory 315, human interface device (HID) 319, input-output (I/O) interface 322, network interface 326, latch detector 328, temperature sensor 330, and accelerometer 332, in an implementation. These components are housed within housing 705. Different implementations of the system may include any number of the components described, in any combination or configuration, and may also include other components not shown.

The components are linked together via a bus 303, which represents the system bus architecture of the system unit. Although FIG. 4 shows one bus that connects to each component of the system unit, bus 303 is illustrative of any interconnection scheme that links the components of the system unit. For example, one or more bus subsystems can interconnect one or more of the components of the system unit. Additionally, the bus subsystem may interconnect components through one or more ports, such as an audio port (e.g., a 2.5-millimeter or 3.5-millimeter audio jack port), a universal serial bus (USB) port, or another port. Components of the system unit may also be connected to the processor via direct connections, such as direct connections through a printed circuit board (PCB).

In an implementation, system unit 301 includes a sensor probe 346. The sensor probe includes a probe tip 338 and a connector 336. The probe tip is connected to the connector via a first communication link 342 and a second communication link 344. First communication link 342 may include an electrical wire, a set of electrical wires (e.g., a ribbon cable), a waveguide (e.g., fiber optic cables), a set of waveguides (e.g., a set of fiber optic cables), a wireless communication link, or any combination of these types of links. The second communication link may include an electrical wire, a set of electrical wires (e.g., a ribbon cable), a waveguide (e.g., a fiber optic cable), a set of waveguides (e.g., a set of fiber optic cables), a wireless communication link, or any combination of these types of links. The electrical wire or sets of electrical wires of the first communication link, the second communication link, or both can include one or more electrical traces on a printed circuit board.

The connector connects (e.g., removably connects) the probe tip, the wires, waveguides, or any combination of these elements to the signal emitter and signal detector of the system unit. For example, a communication link 343 may connect the signal emitter to the connector and a communication link 345 may connect the signal detector to the connector. Each of the communication links 343 and 345 may include an electrical wire, a set of electrical wires (e.g., a ribbon cable) one waveguide, a set of waveguides, a wireless communication link, or any combination of these links. Each communication link can also include one or more electrical traces on a printed circuit board. For example, the connector may include one or more connectors that are mounted on a PCB. Communication links 342, 344, or either one of these links may be ribbon cables that connect to the probe tip and connect to connectors mounted on a PCB. In this implementation, communication links 343 and 345 can be electrical traces on the PCB that link to the single emitter, signal detector, or both. In this implementation, the signal emitters and signal detectors may be electrical emitters and detectors that control light emitters, light detectors, or both in the probe tip.

In an implementation where the probe tip is separable from the system unit 301, connector 336 may have a locking feature, such as an insert connector that may twist or screw to lock. If so, the connector is more securely held to the system unit and it will need to be unlocked before it can be removed. This will help prevent the accidental removal of the probe tip from the system unit.

The connector may also have a first keying feature, so that the connector can only be inserted into a connector receptacle of the system unit in one or more specific orientations. This will ensure that proper connections are made.

The connector may also have a second keying feature that provides an indication to the system unit that a type of probe (e.g., a probe from many different types of probes) that is attached. The system unit may be adapted to make measurements for a number of different types of probes. When a probe is inserted in the system unit, the system uses the second keying feature to determine the type of probe that is connected to the system unit. Then the system unit can perform the appropriate functions, use the appropriate algorithms, or otherwise make adjustments in its operation for the specific probe type.

In an implementation, signal emitter 331 includes one or more light sources that emit light (visible light, infrared light, or both) at one or more specific wavelengths. In a specific implementation, the light sources emit five or more wavelengths of light (e.g., 730 nanometers, 760 nanometers, 810 nanometers, 845 nanometers, and 895 nanometers). Other wavelengths of light are emitted by the light sources, including shorter and longer wavelengths of light in other implementations. The signal emitter may include one or more laser diodes or one or more light emitting diodes (LEDs).

In an implementation, signal emitter 331 is an emitter that emits electrical signals to one or more light sources, which may emit light based on the received electrical signals. In some implementations, the signal emitter includes one or more light sources and electrical signal emitters that are connected to the light sources.

In an implementation, signal detector 333 includes one or more photodetectors capable of detecting the light at the wavelengths produced and emitted by the signal emitter. In another implementation, the signal detector 333 is an electrical signal detector that detects electrical signals generated by one or more photodetectors. In another implementation, the signal detector includes one or more photodetectors and one or more electrical detectors that are connected to the photodetectors.

In an implementation, HID 319 is a device that is adapted to allow a user to input commands into the system unit. The HID may include one or more buttons, one or more slider devices, one or more accelerometers, a computer mouse, a keyboard, a touch interface device (e.g., a touch interface of display 307), a voice interface device, or another HID.

In an implementation where the HID is an accelerometer and the system unit is a handheld unit, the accelerometer may detect movements (e.g., gestures) of the system unit where the system unit may be moved by a user. Movements may include a left movement, right movement, forward movement, back movement, up movement, down movement, one or more rotational movements (e.g., about one or more axes of rotation, such as the x-axis, y-axis, z-axis, or another axis), any combinations of these movements, or other movements.

Information for the various movements detected by the accelerometer may be transmitted to the processor to control one or more systems of the system unit. For example, an upward movement (e.g., a lifting movement) may be transmitted to the processor for powering on the system unit. Alternatively, if the system unit is set down and left unmoved for a predetermined period of time, then the processor may interpret the lack of movement detected by the accelerometer as a standby mode signal and may place the system unit in a standby power mode (a lower power mode than a normal operation mode where oximetry measurements can be made by the system unit), or a power-down signal and may power down the system unit.

When the system unit is powered on, information for a left movement or a right movement detected by the accelerometer and transmitted to the processor may be used by the processor to control the system unit. For example, a left or right movement of the system unit may be used by the processor to change menu items displayed on the display. For example, the processor may use the information for a left movement to scroll menu items on the display to the left (e.g., scroll a first menu item left and off of the display to display a second menu item on the display). The processor may use the information for a right movement of the system unit to scroll menu items to the right (e.g., scroll a first menu item right and off of the display, and display a second menu item on the display).

The HID and processor may be adapted to detect and use various movements to activate a menu item that is displayed on the display. For example, information for an upward movement or a downward movement may be detected and used to activate a menu item that is displayed on the display. For example, if a user is prepared to take an oximeter measurement and a menu option is displayed for taking an oximeter measurement, a quick downward movement of the system unit may start a measurement when the probe tip is placed in contact with tissue The HID may include one or more accelerometers to detect motion in various directions (e.g., linear, rotational, or both). The accelerometers can include one or more capacitive micro-electro-mechanical system (MEMS) devices, one or more piezoresistive devices, one or more piezoelectric devices, or any combination of these devices.

In an embodiment, accelerometer 332 is adapted to detect relatively high G-force accelerations associated with a shock that the system unit experiences. The shock may be from bumping the system into something, dropping the system unit (e.g., dropping the system unit on a table or the floor), or other shock events. In an implementation, if the accelerometer indicates to the processor that a shock event has occurred, the processor can take a number of actions. For example, the processor can shut down the system unit. The processor can display one or more messages on the display. The messages may indicate that the system unit should be recalibrated. The message may indicate that contact between the system unit and the sheath should be checked. The accelerometer may include one or more capacitive micro-electro-mechanical system (MEMS) devices, one or more piezoresistive devices, one or more piezoelectric devices, or any combination of these devices.

The nonvolatile memory 315 may include a FLASH memory, other nonvolatile solid-state storage (e.g., USB flash drive), battery-backed-up volatile memory, tape storage, reader, and other similar media, and combinations of these. In some implementations, the nonvolatile memory includes a mass disk drive, magnetic disks, optical disks, magneto-optical disks, fixed disks, hard disks, CD-ROMs, recordable CDs, DVDs, recordable DVDs (e.g., DVD-R, DVD+R, DVD-RW, DVD+RW, HD-DVD, or Blu-ray Disc). The volatile memory may include a random access memory (RAM).

The processor may include a microcontroller, a microprocessor, an application specific integrated circuit (ASIC), programmable logic (e.g., field programmable gate array), or any combination of these circuits, such as a microprocessor and an FPGA or a microcontroller and an FPGA. The processor may include multiple processors or a multicore processor, which may permit parallel processing of information.

In an implementation, the system unit is part of a distributed system. In a distributed system, individual systems are connected to a network and are available to lend resources to another system in the network as needed. For example, a single system unit may be used to collect results from numerous sensor probes at different locations.

Aspects of the invention may include software executable code, firmware (e.g., code stored in a read only memory (ROM) chip), or both. The software executable code or firmware may embody algorithms used in making oxygen saturation measurements of the tissue. The software executable code or firmware may include code to implement a user interface by which a user uses the system, displays results on the display, selects or specifies parameters that affect the operation of the system, or execute algorithms and calculations to generate a result.

Further, a computer-implemented or computer-executable version of the invention may be embodied using, stored on, or associated with a computer-readable medium. A computer-readable medium may include any medium that participates in providing instructions to one or more processors for execution. Such a medium may take many forms, including but not limited to, nonvolatile, volatile, and transmission media. Nonvolatile media includes, for example, flash memory, or optical or magnetic disks. Volatile media includes static or dynamic memory, such as cache memory or RAM. Transmission media includes coaxial cables, copper wire, fiber optic lines, and wires arranged in a bus. Transmission media can also take the form of electromagnetic, radio frequency, acoustic, or light waves, such as those generated during radio wave and infrared data communications.

For example, a binary, machine-executable version, of the software of the present invention may be stored or reside in RAM or cache memory, or on a mass storage device. Source code of the software of the present invention may also be stored or reside on a mass storage device (e.g., hard disk, magnetic disk, tape, or CD-ROM). As a further example, code of the invention may be transmitted via wires, radio waves, or through a network such as the Internet. Firmware may be stored in a ROM of the system.

Computer software products may be written in any of various suitable programming languages, such as C, C++, C #, Pascal, Fortran, Perl, MATLAB (from MathWorks, www.mathworks.com), SAS, SPSS, JavaScript, AJAX, and Java. The computer software product may be an independent application with data input and data display modules. Alternatively, the computer software products may be classes that may be instantiated as distributed objects. The computer software products may also be component software such as Java Beans (from Sun Microsystems) or Enterprise Java Beans (EJB from Sun Microsystems).

An operating system for the system may be one of the Microsoft Windows® family of operating systems (e.g., Windows XP, Windows XP x64 Edition, Windows Vista, Windows CE, Windows 7, Windows 8, Windows 10, Windows 11, Windows Mobile), Linux, HP-UX, UNIX, Solaris, Mac OS X, Alpha OS, AIX, IRIX32, or IRIX64. Microsoft Windows is a trademark of Microsoft Corporation. Other operating systems may be used, including custom and proprietary operating systems.

Furthermore, the system may be connected to a network and may communicate with other systems using this network. The network may be an intranet, internet, or the Internet, among others. The network may be a wired network (e.g., using copper), telephone network, packet network, an optical network (e.g., using optical fiber), or a wireless network, or any combination of these. For example, data and other information may be passed between the computer and components (or steps) of a system of the invention using a wireless network using a protocol such as Wi-Fi (IEEE standards 802.11, 802.11a, 802.11b, 802.11e, 802.11g, 802.11i, and 802.11n, just to name a few examples). For example, signals from a system may be transferred, at least in part, wirelessly to components or other systems or computers.

In an embodiment, through a Web browser or other interface executing on a computer workstation system or another device (e.g., a laptop computer, smartphone, or personal digital assistant), a user accesses system unit 301 or laparoscopic oximeter 5, which is described below with respect to FIGS. 30-36, through a network such as the Internet. The user will be able to see the data being gathered by the system unit. Access may be through the World Wide Web (WWW). The Web browser is used to download Web pages or other content in various formats, including HTML, XML, text, PDF, and postscript, and may be used to upload information to other parts of the system. The Web browser may use uniform resource identifiers (URLs) to identify resources on the Web and hypertext transfer protocol (HTTP) in transferring files on the Web.

Figure 5:
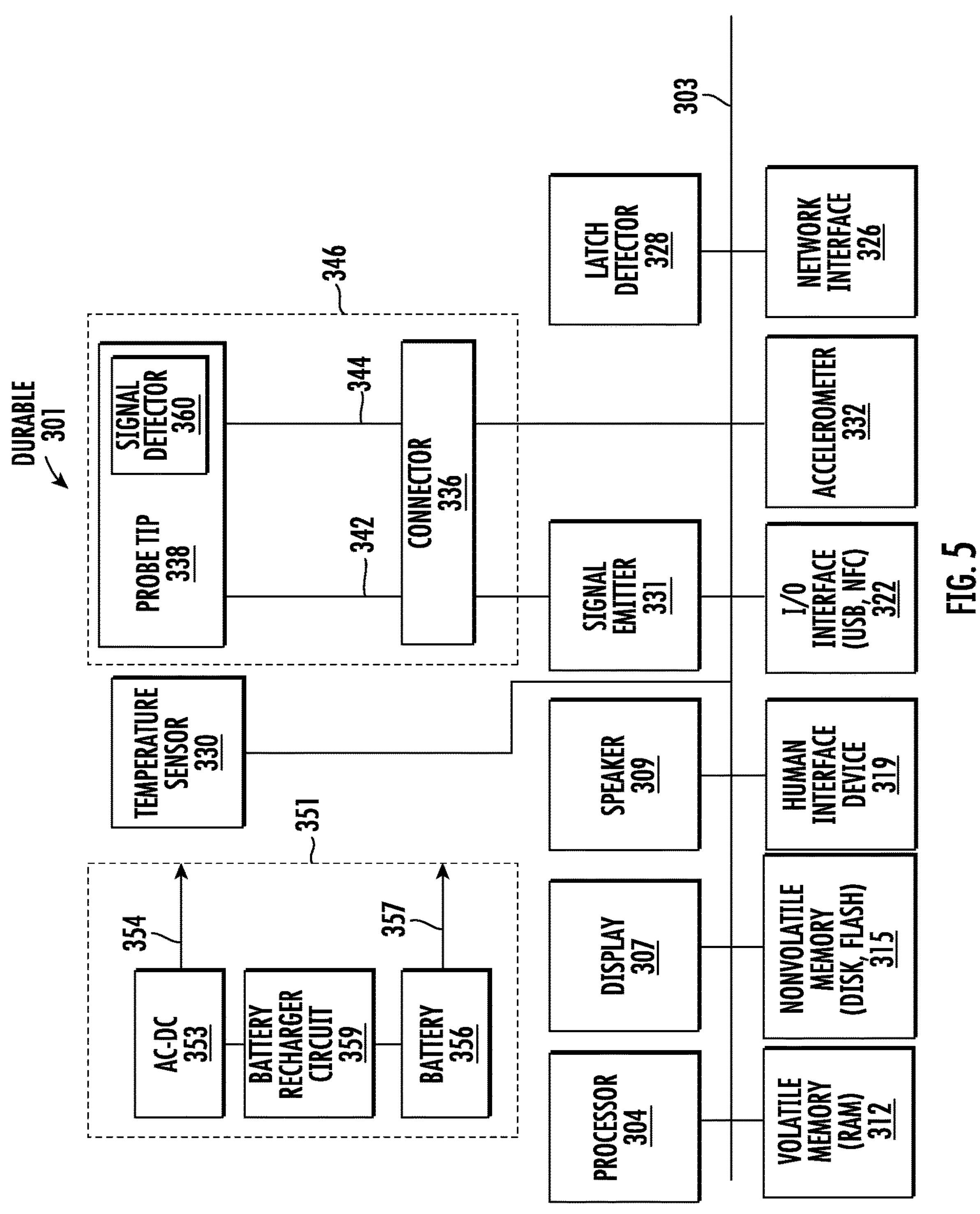
FIG. 5 shows a block diagram of the system unit, in an implementation.

FIG. 5 shows a block diagram of the system unit, in an implementation. The implementation of the system unit shown in FIG. 5 is similar to the implementation of the system unit shown in FIG. 4 but differs in that the signal detector 360 is located in probe tip 346. A wire or set of wires (e.g., a ribbon cable) may connect the signal detector to the bus and processor. For example, a ribbon cable that is connected to the signal detector may also be connected to a connector or socket mounted on a PCB that the processor and other circuits are mounted on. The signal detector may be located at a probe face of the probe tip. The signal emitter may be optically located behind the probe face of the probe tip.

Figure 6:
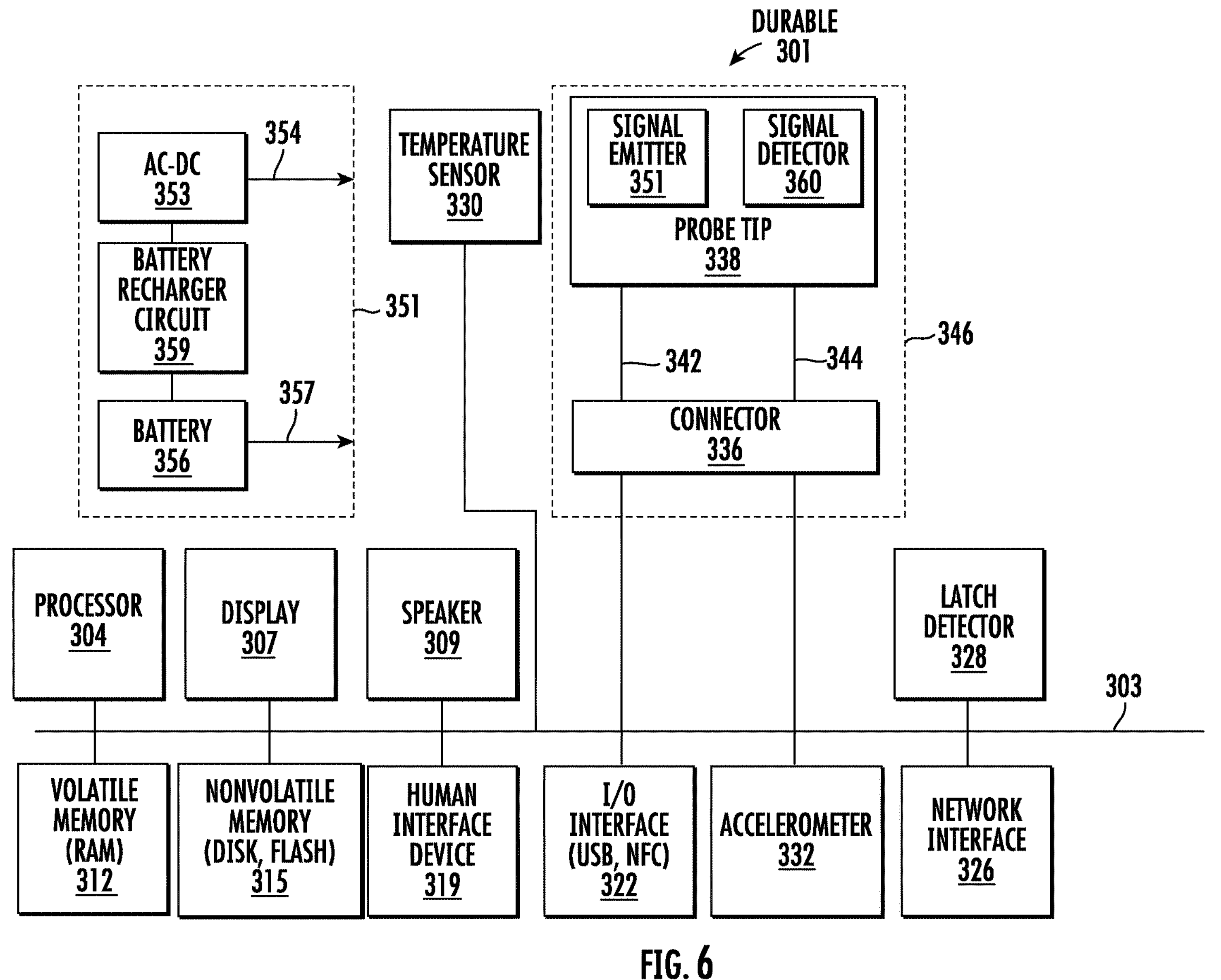
FIG. 6 shows a block diagram of the system unit, in an implementation.

FIG. 6 shows a block diagram of the system unit, in an implementation. The implementation of the system unit shown in FIG. 6 is similar to the implementations of the system units shown in FIGS. 4-5 but differs in that the signal emitter 331 and the signal detector 344 are located in probe tip 346. A wire or wires (e.g., one or more ribbon cables) may connect the signal emitter, the signal detector, or both to the bus and processor. A first ribbon cable may connect the signal emitter to the bus and processor and a second ribbon cable may connect the signal detector to the bus and processor. For example, the first ribbon cable that is connected to the signal emitter may also be connected to a connector or socket mounted on a PCB that the processor and other circuits are mounted on, and the second ribbon cable that is connected to the signal detector may also be connected to a connector or socket mounted on the PCB. The signal detector may be located at a probe face of the probe tip. The signal emitter may be optically located behind the probe face of the probe tip.

In an implementation, connector 336 includes a locking feature, such as an insert connector that inserts into a connecting port and then twists or screws to lock. If so, the connector is more securely held to the system unit and it will need to be unlocked before it can be removed. This will help prevent accidental removal of the probe.

In an implementation, connector 336 includes one or more PCBs that are connected to one or more wires (e.g., ribbon cables) that connect to the signal emitter, the signal detector, or both. For example, a first ribbon cable may connect to a first PCB that connects to the signal emitter. A second ribbon cable may connect to a second PCB that connects to the signal detector.

Block 351 shows a power block of the system unit having both AC and battery power options. In an implementation, the system includes an AC-to-DC converter 353, such as a full-wave rectifier. The converter takes AC power from a wall socket, converts AC power to DC power, and the DC output is connected (indicated by an arrow 354) to the components of the system unit needing power.

In an implementation, the system unit is battery operated. The DC output of a battery 356 is connected (indicated by an arrow 357) to the components of the system unit needing power. The battery may be recharged via a recharger circuit 359, which receives DC power from the AC-to-DC converter. The AC-to-DC converter and recharger circuit may be combined into a single circuit. In an implementation, the battery is rechargeable via magnetic charging or induction charging.

In an implementation, block 351 is a battery module that includes one or more batteries that power the components of the system unit. The batteries may be rechargeable or disposable batteries. The block may not include the AC-to-DC converter. Block 351 may be a block that is integrated with the system unit or is separable from the system unit.

Figure 7:
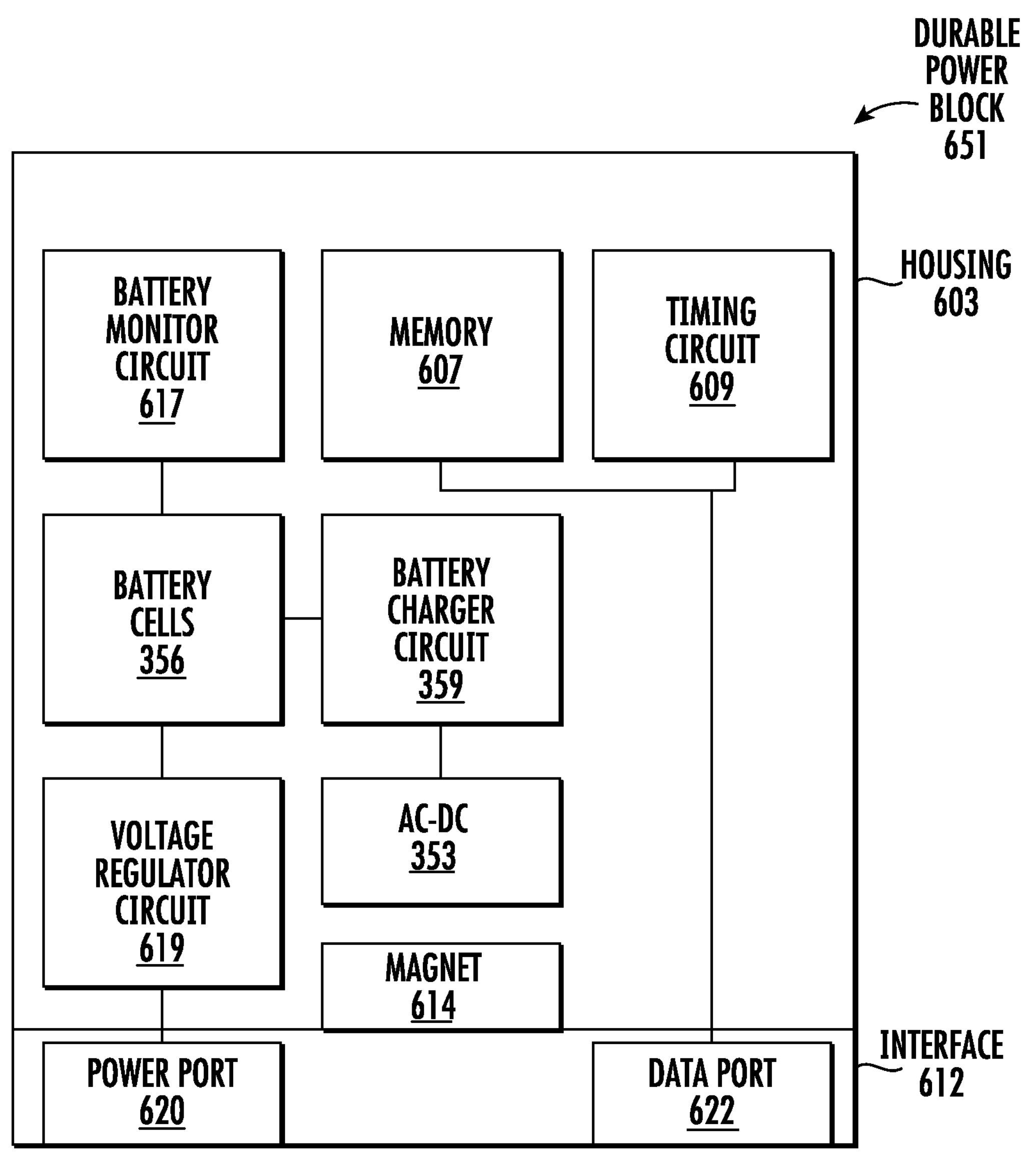
FIG. 7 shows a power block of the probe unit, in an implementation.

FIG. 7 shows block 651 that is a power block that is usable with the system unit, in an implementation. Block 651 is similar to block 351 but may include a battery monitor 617, a voltage regulator circuit 619, a memory 607, a timing circuit 609, an interface 612, which includes a power port 620 and a data port 622, a magnet 614, other circuits, or any combination of these circuits.

Battery monitor 617 may be connected to the battery cells 356 and may monitor the capability of the battery cells. For example, the battery monitor may determine a current charge state, such as a percentage of the total possible charge. The battery monitor may determine the charge capacity of the battery cells. The charge capacity may be a percentage of the charge capacity compared to the charge capacity of the battery cells when new. The battery monitor may determine the maximum power delivery capability of the battery.

The battery cells may be disposable battery cells, such as alkaline battery cells, or rechargeable battery cells, such as nickel-metal hydride, lithium battery cells (e.g., Li/FeS2 size AA, AAA, N, CR123, 18650, or others), lithium polymer, or other types of cells. The power back may include four battery cells that are AA size cells that output 1.5 volts. The four batteries may be in series to output 6 volts, or may be in series and parallel to output 3 volts.

Voltage regulator circuit 619 may be connected between the battery cells and the power port of the battery interface 612. The voltage regulator circuit conditions the voltage output from the battery to output an approximately constant voltage. The voltage regular circuit may also include a DC-to-DC converter that converts a first voltage output from the battery cells to a second voltage that is different from the first voltage.

The timing circuit is a circuit that determines the amount of time length that the battery has been used. Information for the amount of time may be stored in the memory and may be transferred through the data port to the processor when the processor queries the memory for the information.

In an embodiment, the memory may also store an encrypted identifier that identifies the power block. The processor may be adapted to retrieve the encrypted identifier via the power blocks data port. The processor or another decryption circuit of the system unit may decrypt the encrypted identifier and may identify the power block based on the identifier after decryption. The identifier may identify the manufacturer of the power block or may identify other information about the power block, such as the manufacturing date, the battery cell type, battery cell voltage, elapsed usage time, or any combination of these elements. In an implementation, if the identifier is not a known identifier that is known to the system unit, then the processor with not allow the system unit to operate with the power block. That is, the system unit will not operate with a power block manufactured by an unknown manufacturer.

Allowing the system unit to operate with known (e.g., authorized) power blocks, the system unit is assured that the power provided by the power block is within the operating specifications of the system unit. Therefore, the circuits, signal emitters, signal detectors, and other elements of the system unit will operate within predetermined parameters and will not operate outside of the predetermined parameters. Also, using a known battery from a known manufacturer provides that the stem unit will operate for a known period of time so that the system unit will not run out of battery power during a medical procedure, such as a surgery. Operating the system unit according to predetermined parameters, facilitates the system unit making accurate and reliable oximetry measurements.

In an implementation, nonvolatile memory 315 stores one or more identifiers for one or more power blocks that may operate with the system unit. The processor may compare the identifier for the power pack that has been decrypted to the one or more identifiers retrieved from the nonvolatile memory to determine whether the power block will be allowed to operate with the system unit. If the power block is not authorized for use with the system unit, the processor may cause a message to be displayed on the display that indicates that the power block is not authorized for use with the system unit. If the power block is authorized to operate with the system unit, then the system unit may operate to make oximetry measurements without displaying information on the display about the authenticity or the inauthenticity of the power block.

In an implementation, the memory of the power block stores an indicator that indicates whether the battery has been previously used. The indicator may be the time information for the amount of time that the power block has operated. A nonzero use time stored in the memory is an indicator that the power block has been previously used. Alternatively, the indicator may be an identifier of a system unit that the power block has been connected to and provided power to. For example, the nonvolatile memory of the system unit may store an identifier of a system unit. The processor of the system unit may transfer the system identifier of the system unit to the power block for storage in the power block's memory. In an implementation, the system unit tests the battery use by a threshold that is greater than zero (e.g., usage number stored in the battery's memory), to handle the case of someone accidentally disconnecting the battery before insertion into the sheath. If the system unit checked a usage of zero versus nonzero, then the battery would be rejected for use for the accidental battery disconnection situation. A threshold greater than zero allows for the system unit test to not interrupt the workflow of connecting the battery and placing the battery in the sheath. That is, the implementation attempts to ensure that a power block is fully charged and can be used for the duration of a medical procedure (e.g., a surgery) without the power block running out of stored energy. Ensuring that a power block is unused prior to using the power block during a medical procedure provides that the power block will not run out of power during the procedure and minimize risk to a patient. That is, patient risk is lowered if a system unit used during a procedure does not run out of power and can be used for patient monitoring when required.

In an implementation, when the power block is attached to a system unit, the processor of the system unit may query the power block's memory to retrieve the time information for the amount of time that the power block has operated. In an implementation, if the system unit determines that the power block has been previously used based on the time information, then the system unit will not operate with the power block. Similar to the embodiment described immediately above, ensuring that a power block is unused prior to using the power block during a medical procedure provides that the power block will not run out of power during the procedure and minimize risk to a patient.

When the power block is attached to a system unit, the processor of the system unit may query the power block's memory to retrieve any system identifier that may be stored in the power block's memory. In an implementation, if a system identifier retrieved from the power block's memory is different from the system identifier of the system unit that is retrieved the system unit from the power block's memory, then the system unit will not operate with the power block.

The power block may include one more magnets 614 that are arranged in an arrangement, such as a square, a rectangular, or another arrangement. A system unit may also have one or more magnets or one or more metal plates (e.g., ferromagnetic plates) that are arranged in an arrangement that is complementary to the arrangement of magnets in the power block. The magnets of the power block may attract the magnets or metal plates of the system unit when the power block is placed in contact with the system unit. The magnetic attraction between the magnets or plates may hold the power block in place when the system unit is being used.

The power block may include one more plates (e.g., ferromagnetic plates) that are arranged in an arrangement, such as square, rectangular, or another arrangement. The system unit may include one or more magnets that are arranged in a complementary arrangement. The magnets of the system unit may magnetically attract the metal plates of the power block when the power block is placed in contact with the system unit. The magnetic attraction between the magnets and plates may hold the power block in place when the system unit is being used.

In an implementation, the power port of the power block includes at least two electrical contacts (e.g., a power contact and a ground contact) and the data port includes at least two electrical contacts (e.g., a data line and a shared ground contact with the power port). The electrical contacts are arranged in an arrangement, such as in a row, in a square, in a rectangle, or in another arrangement. The system unit includes a power port that includes at least two electrical contacts (e.g., a power contact and a ground contact) and includes a data port that includes at least two electrical contacts (e.g., a data line and a shared ground contact with the power port). The arrangement of the electrical contacts is complementary to the electrical contacts of the power block.

When the power block is placed in contact with the system unit, the magnetic attraction between the magnets or between the magnets and metal plates forces the electrical contacts of the power port in the system unit into contact with the electrical contacts of the power port of the power block. Also, the magnetic attraction forces the electrical contacts of the data port in the system unit into contact with the electrical contacts of the data port of the power block. As such, electrical power can be transferred from the power block to the system unit to power the circuits and other elements of the system unit, and data can be transferred between the power block and the system unit.

In an implementation, the system unit performs oximetry readings of patient tissue and generates an average oximetry value from a number of the oximetry readings of the patient tissue. The system unit can display the average oximetry value on the display of the system unit. The system unit can perform oximetry readings of tissue and display the oximetry values for the reading while the system unit is located in a sheath or not located in the sheath. Sheath implementations usable with the system unit are described below with respect to FIGS. 8-12.

One or more of the oximetry readings may be for a single tissue site of a patient, different tissue sites of a patient, or a combination of these tissue sites. The averaging function performed by the system unit allows the system unit to remember oximetry reading values, such as oxygen saturation (i.e., StO2), absorption coefficient, or other oximetry reading values, and generate an average oximetry value for some or all of the remembered oximetry reading values. The oximetry reading values that are displayed on the display can include one or more oximetry reading values (e.g., oxygen saturation values) included in an average of the oximetry reading values, an average of the oximetry reading values (e.g., an average oxygen saturation value), any combination of these values, or any combination of these values can be weighted by a quality metric value. A quality metric value can be an indicator of the quality of contact of eh probe face of the system unit to tissue, the sheath to tissue, and thus an indicator of the quality of the oximeter reading values. The system unit can assess quality, for example, of contact of the probe face or sheath to the tissue, a quality of the tissue, or both, and generate a quality metric value based on one or both of these assessments In an implementation, the processor of the system unit makes oximetry readings of patient tissue at a measurement frequency of between about 0.2 hertz and about 10 hertz (e.g., about 0.5 hertz to about 6 hertz). The measurement frequency of oximetry readings performed by the system unit may vary by 0 percent, plus or minus 0.5 percent, plus or minus 1 percent, plus or minus 1.5 percent, plus or minus 2 percent, or other values as will be understood by those of skill in the art.

In an implementation, oximetry reading values that are displayed on the display of the system unit are updated on the display at a frequency that is less than the measurement frequency. For example, the system unit may display oximetry reading values for oxygen saturation of patient tissue no more often than about once per second to no more than about once per every three seconds, such as about no more than once per every two seconds. That is, about every two seconds or less, the system unit displays a newly measured oxygen saturation value on the display of the system unit.

Figure 8:
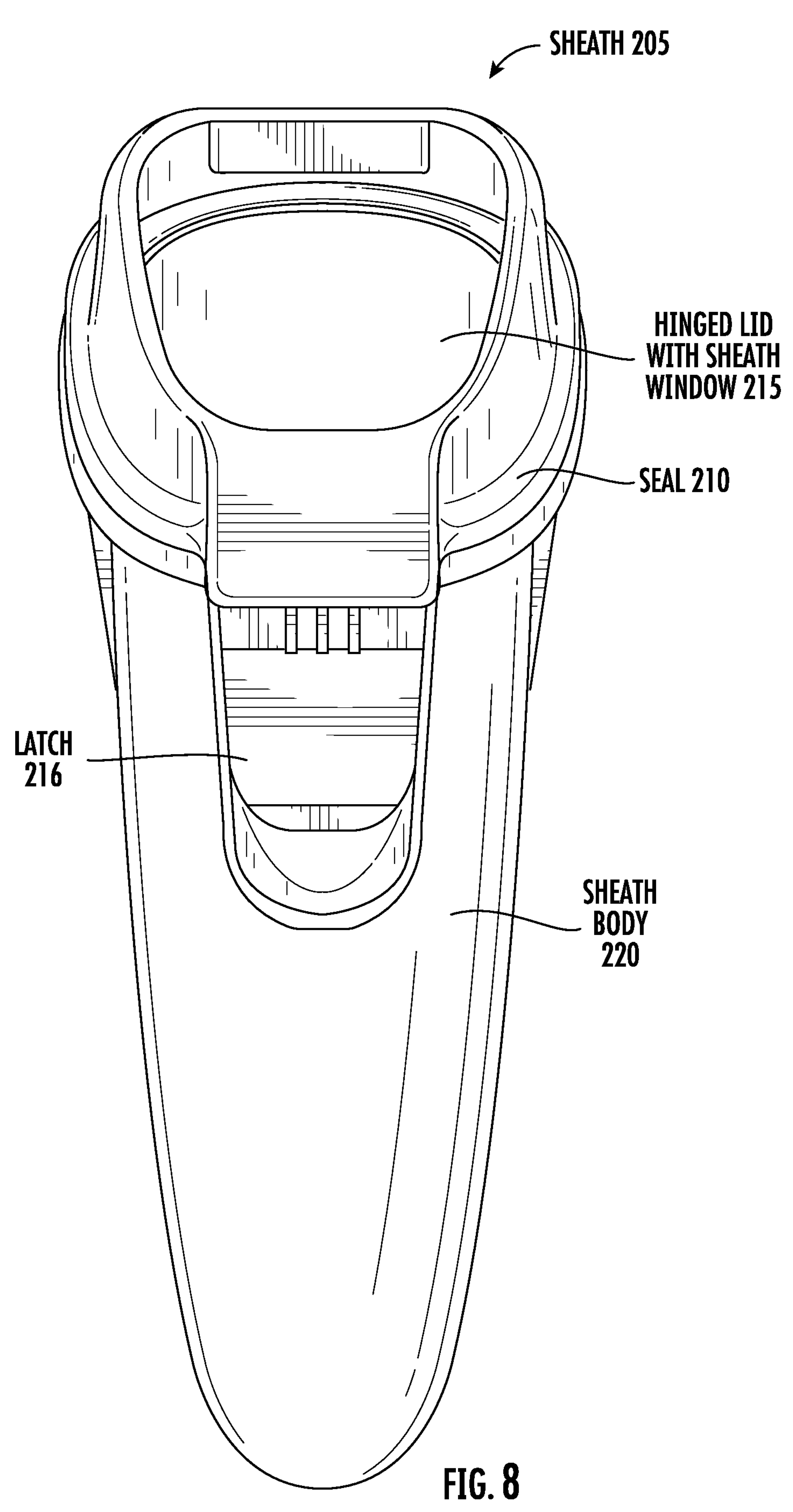
FIGS. 8-9 show various views of a sheath that is configured to house the system unit for interoperative use, in an implementation.
Figure 9:
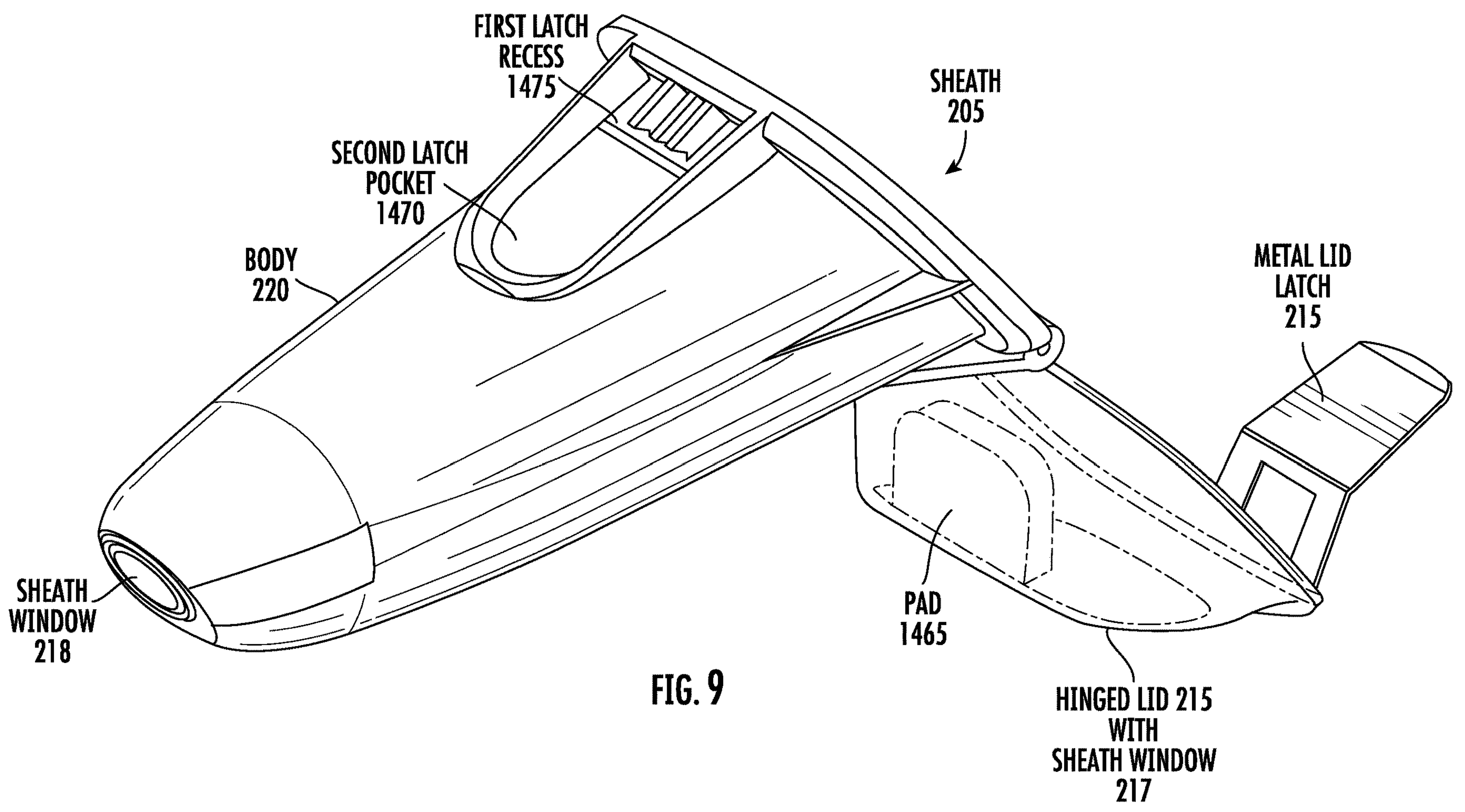

FIGS. 8-9 show various views of a sheath 205, in an implementation. The sheath can accept the system unit into an interior space of the sheath so that the system unit is sealed in the sheath. The system unit can be sealed in the sheath so that contaminants on tissue do not contact the system unit so that the system unit can be reused. Additionally, the system unit can be sealed in the sheath so that contaminants on the system unit do not contact patient tissue. The system unit sealed in the sheath also allows the system unit to be entered into the sterile field of an operating room without contaminating the sterile field. The sheath includes a body 220 and a hinged lid 215 with a window through which the display of the system unit is visible when the system unit is enclosed in the sheath with the lid closed and sealed in by a seal 210 and a latch 216. The sheath also includes a latch recess 1475, a second latch pocket 1470, and a pad 1465 for securely holding the system unit in the sheath when the sheath's lid 215 is closed to house the system unit.

The lid 215 is shown in an open position in FIGS. 8-9 with respect to the body 220 where a system unit can be inserted into the sheath or removed from the sheath. The hinge that connects the lid and the body can be on a backside of the sheath. The body can include an O-ring recess 1400 of the top of the body. An O-ring 1405 is shown in the recess. The lid can also include an O-ring recess 4110 on the bottom of the lid. The O-ring recesses of the body and lid can contact the O-ring when the lid is closed against the body. The O-ring can form a seal that seals the lib to the body so that contaminants cannot enter the seal between the lid and body. The system unit can be inserted into the sheath or removed from the sheath through the top opening of body 220.

FIG. 9 additionally shows the second sheath window 218 at the bottom of the body of the sheath. The second sheath window may generally be round from an end view. In a specific implementation, the second sheath window is circular. The upper and lower surface of the second sheath window may be approximately parallel. Light emitted and detected by the system unit may be transmitted through the sheath window.

Figure 10:
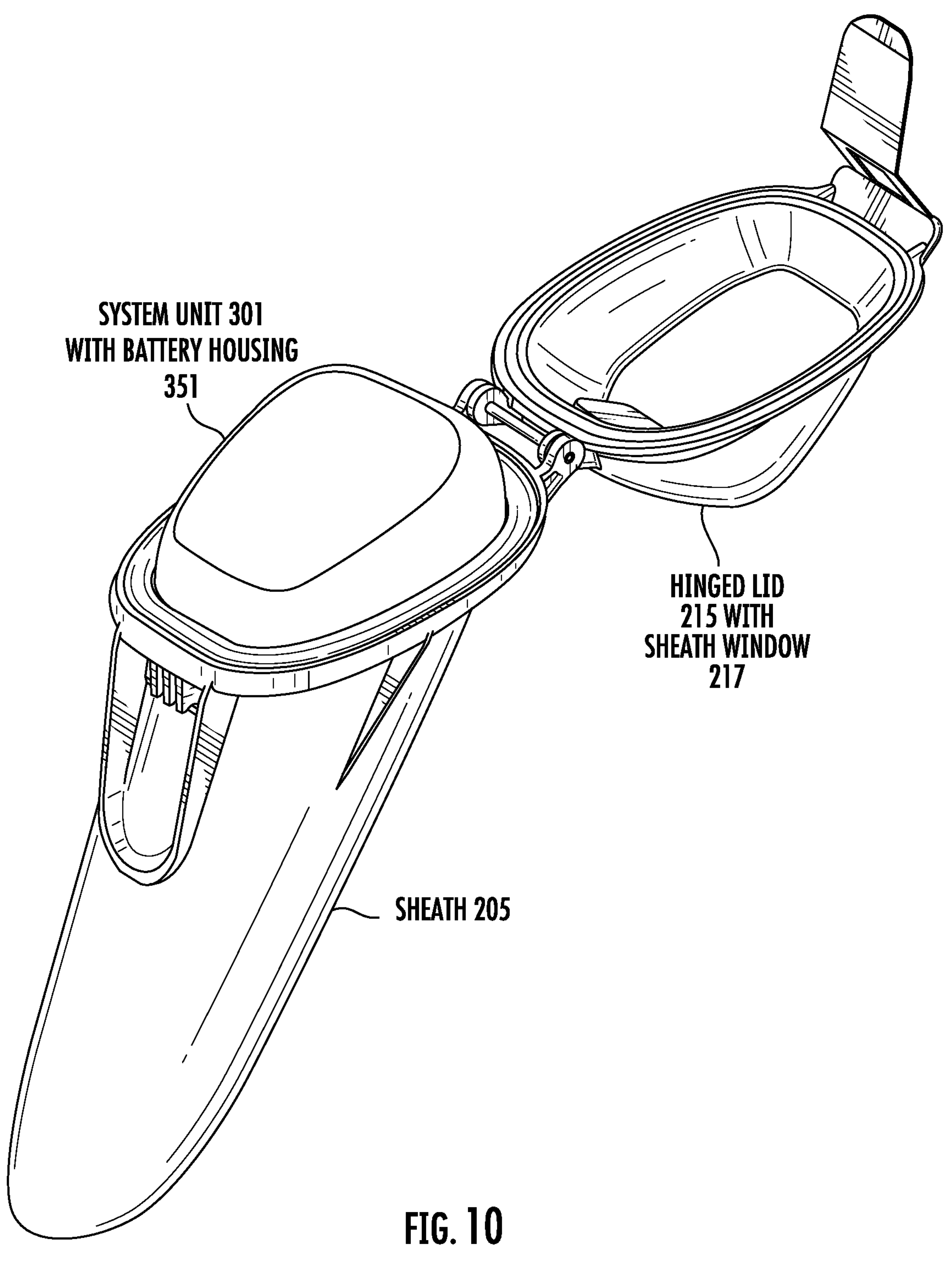
FIG. 10 shows a perspective view of the sheath where the system unit and power block are located in the sheath, in an implementation.

FIG. 10 shows a perspective view of the sheath where the system unit and power block are located in the sheath, in an implementation. The sheath is shown with the sheath lid open and the system unit above the opening of the body of the sheath. The lid may then be closed and the system unit and power block sealed in the sheath ready for use.

Figure 11:
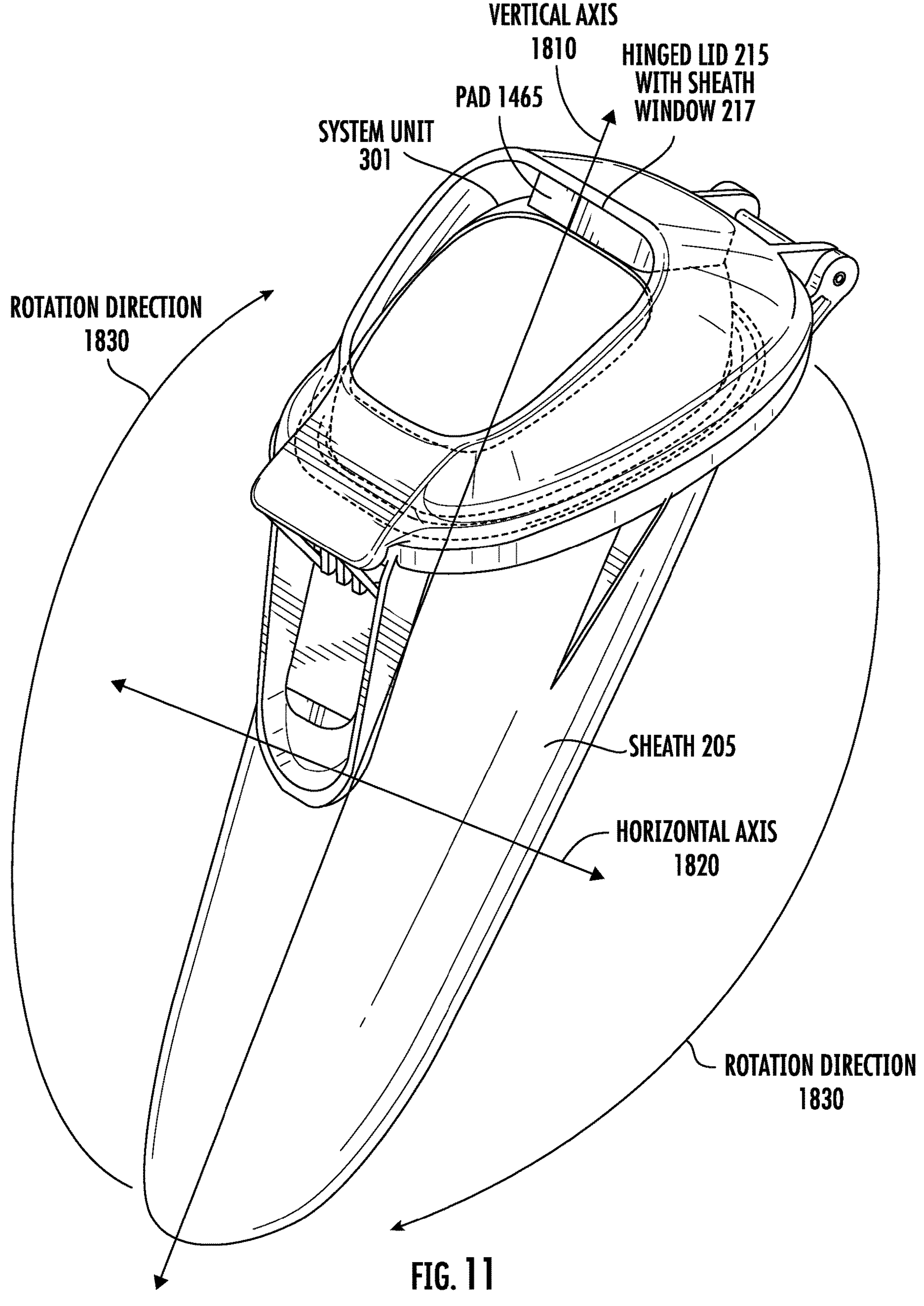
FIG. 11 shows a perspective view of the sheath where the system unit and power block are located in the sheath with the lid of the sheath in a closed position.
Figure 12:
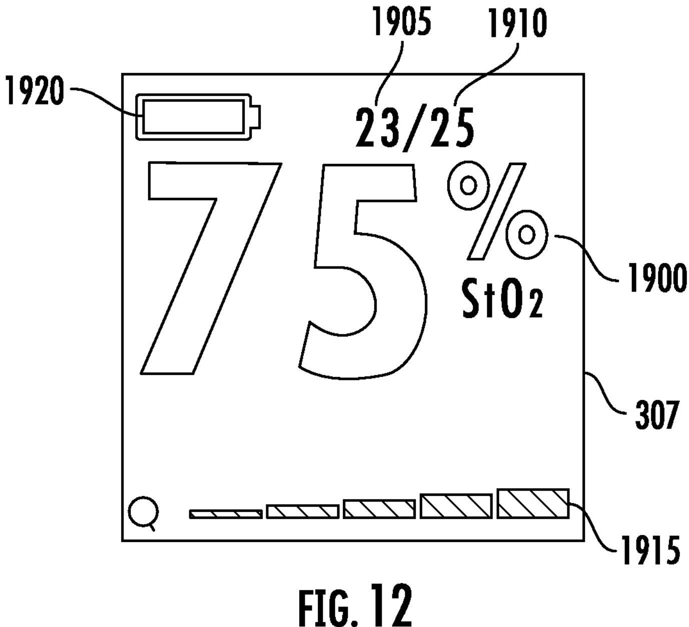
FIGS. 12-15 show the display of the system unit, in an implementation.
Figure 13:
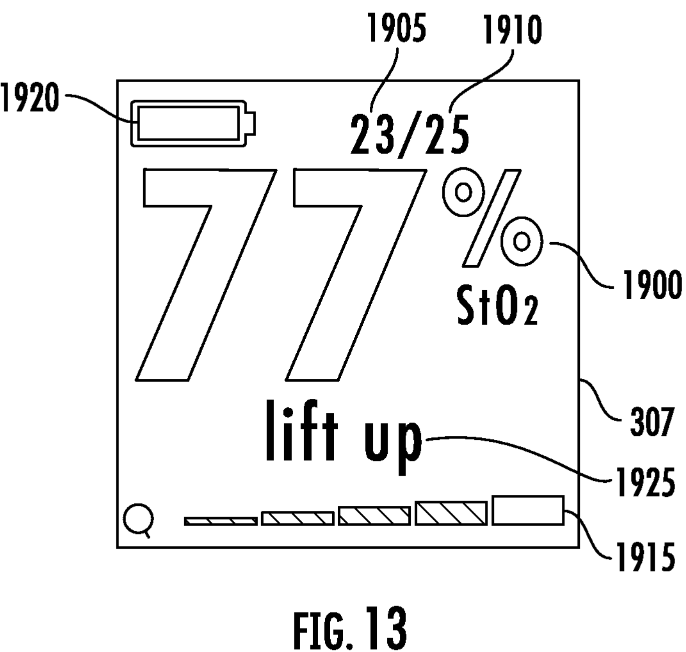

FIG. 11 shows a perspective view of the sheath where the system unit and power block are located in the sheath with the lid of the sheath in a closed position. The display of the system unit is visible through the first window of the lid of the sheath. Information (e.g., text, graphics, or both) that is displayed on the display of the system unit is visible to a user looking through the second window of the lid. The display and window are both proximally located with the probe face and second window distally located when the system is ready for use. With the second window in contact with tissue, the display faces away from the tissue so that the display, through the first window, can be seen by a user.

FIGS. 12-15 show the display 307 of the system unit 301, in an implementation. The display can display a number of pieces of information generated by the system unit. For example, the display can display oximetry information 1900, a number of permitted uses 1905 of the system unit that remain and a number of uses 1910 of the system unit that are available for a new unused system unit, a quality metric 1915, an indicator 1920 for an amount of available battery power in the battery, and a use message 1925. The oximetry information 1900 may include one or more of an oxygen saturation value (i.e., StO2), an oxygenated hemoglobin percentage (i.e., a saturated hemoglobin percentage), a deoxygenated hemoglobin percentage (i.e., an unsaturated hemoglobin percentage), an absorption coefficient, or other measured values. The total number of uses of the system unit may be from 5 to 100. In a specific implementation, the total number of uses of the system unit is 25. In the example shown in FIG. 12, the system unit has been used 2 times and 23 remaining uses are permitted by the system unit. The quality metric 1915 is a quality indicator for the displayed oximetry information 1900. The quality metric in the displayed embodiment is a bar graph. The battery power indicator 1920 may be a bar graph, a highlighted-dehighlighted graph, or other type of indicator. In the implementation shown in FIG. 12, the battery power indicator is a bar graph imposed with an image of a battery.

The use message (e.g., "lift up," "lift," or another message) may be a message for an action (e.g., lift the sheath or system unit if the system unit is used without a sheath) that a user may take so that the system unit will generate an average for a number of oximetry values that are generated by the system unit. The oximetry values can be any of the examples of the oximetry information 2100 described above, such as an oxygen saturation value. The average can be for a single tissue location of a patient or a number of tissue locations for the patient.

After the system unit has taken a first oximetry measurement and displays a first oximetry information 1900 on the display, the system unit may then display the use message. The use message may indicate that the user should "lift up" the system unit so that the second window 218 of the sheath or the probe face of the probe tip 338 of the system unit is not in contact with the tissue being measured. The probe face of the probe tip of the system unit may be in contact with the patient tissue if the system unit is used without the sheath.

Figures 14, 15:
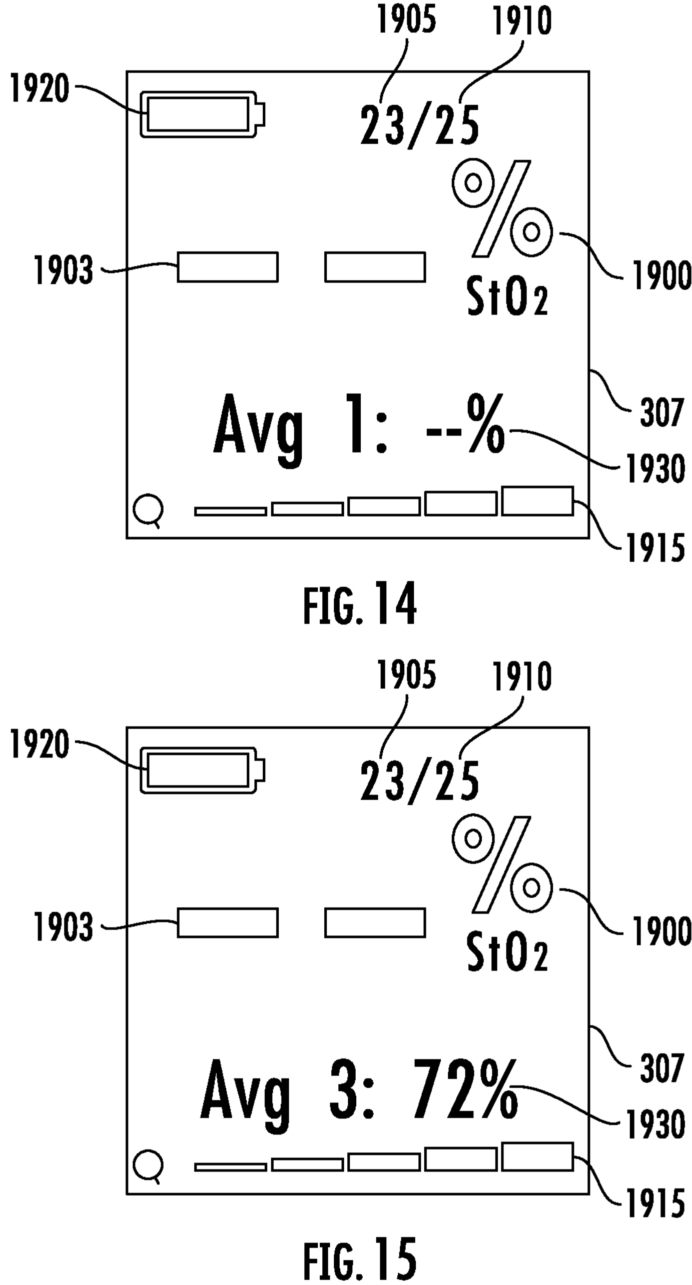

Referring to FIG. 14, after the system unit is lifted by the user and the second window or the probe face is not in contact with the tissue, the display may stop displaying oximetry information 1900 and display two bars 1903 or other information, such as another icon. When the bars are displayed the user can place the second window of the sheath or the probe face of the system unit back into contact with the tissue. The location on the tissue that the second window or probe face is placed in contact with can be the same tissue location that the system unit was lifted from or can be a different location. The system unit will thereafter generate second oximetry information (e.g., second oxygen saturation information for the tissue) for the second placement of the sheath, system unit, or both.

In an implementation, when the system unit is removed from contact with the tissue, the oximetry values for oximetry measurements may be greater than a first threshold value or less than second threshold value. The processor can determine that the system unit has been removed from contact with the tissue when one or more oximetry values are greater or less than the first and second threshold values, respectively. The first and second threshold values can be the same value. The oximetry values for when the system unit is in contact with the tissue may be values that are less than the first oximetry value and greater than the second threshold value.

In another implementation, when the system unit is removed from contact with the tissue, the oximetry values for oximetry measurements may be less than a first threshold value or greater than second threshold value. The processor can determine that the system unit has been removed from contact with the tissue when one or more oximetry values are less than or greater than the first and second threshold values, respectively. The first and second threshold values can be the same value. The oximetry values for when the system unit is in contact with the tissue may be values that are greater than the first oximetry value and less than the second threshold value. The two above describe implementations may differ based on how the system unit implements logic for how the oximetry values are reported.

The display of the system unit may continue to display the two bars 1903 when the second oximetry information is generated or may display the second oximetry information (e.g., second oxygen saturation information). The system unit may also display that there is one average generated 1930 for the first and second oximetry information (e.g., "Avg 1:—%") for the first and second placements on the tissue. In an implementation, for the tissue location, the system unit does not display an average value, but displays other information, such as an icon (e.g., two bars). In an implementation, the first oximetry information for a first tissue location is displayed on the display in the location where averages are displayed, it being understood that a single oximetry measurement for a single tissue location is not an average for a number of tissue locations (e.g., greater than two tissue locations).

After the second oximetry information is generated, the display may again display the use message (e.g., "lift up"). Thereafter the process of lifting and placing the sheath or probe face of the system unit onto the tissue (e.g., at the same tissue location or a different tissue location) may be repeated. Thereafter, the system unit may generate third oximetry information for the tissue on which the second window or probe face is placed. In an implementation, the system unit displays an average value when a third average value of the oximetry information is generated. That is, the average of the first, second, and third oximetry information is referred to as the third average value. In other implementations, the system unit displays an average value when a second average value of oximetry information is generated or a higher number of average values of the oximetry information is generated.

Referring to FIG. 15, the third average value for the oximetry information is displayed on the display. After the third oximetry information is generated, the use message may be displayed for each subsequent oximetry information generated (e.g., fourth, fifth, sixth, seventh, or more) and an average may be generated and displayed.

In an implementation, the average is no longer accumulated after a fixed number (e.g., nine) of averages are generated. In an implementation, the average is reset if the accelerometer detects that the system unit is turned upside down (i.e., inverted). In another implementation, the number of oximetry measurements (e.g., oxygen saturation values) that are included in an average is not capped to a fixed number of generated average values and the average continues to be generated when the conditions for a valid oximetry measurement is made (e.g., lift up is displayed on the display and the system unit is lifted when lift up is displayed on the display) for an oximetry measurement that is to be included into the average value. That is, if the system unit is rotated vertically by about 180 degrees+/−about 45 degrees the average will be reset.

Figure 16:
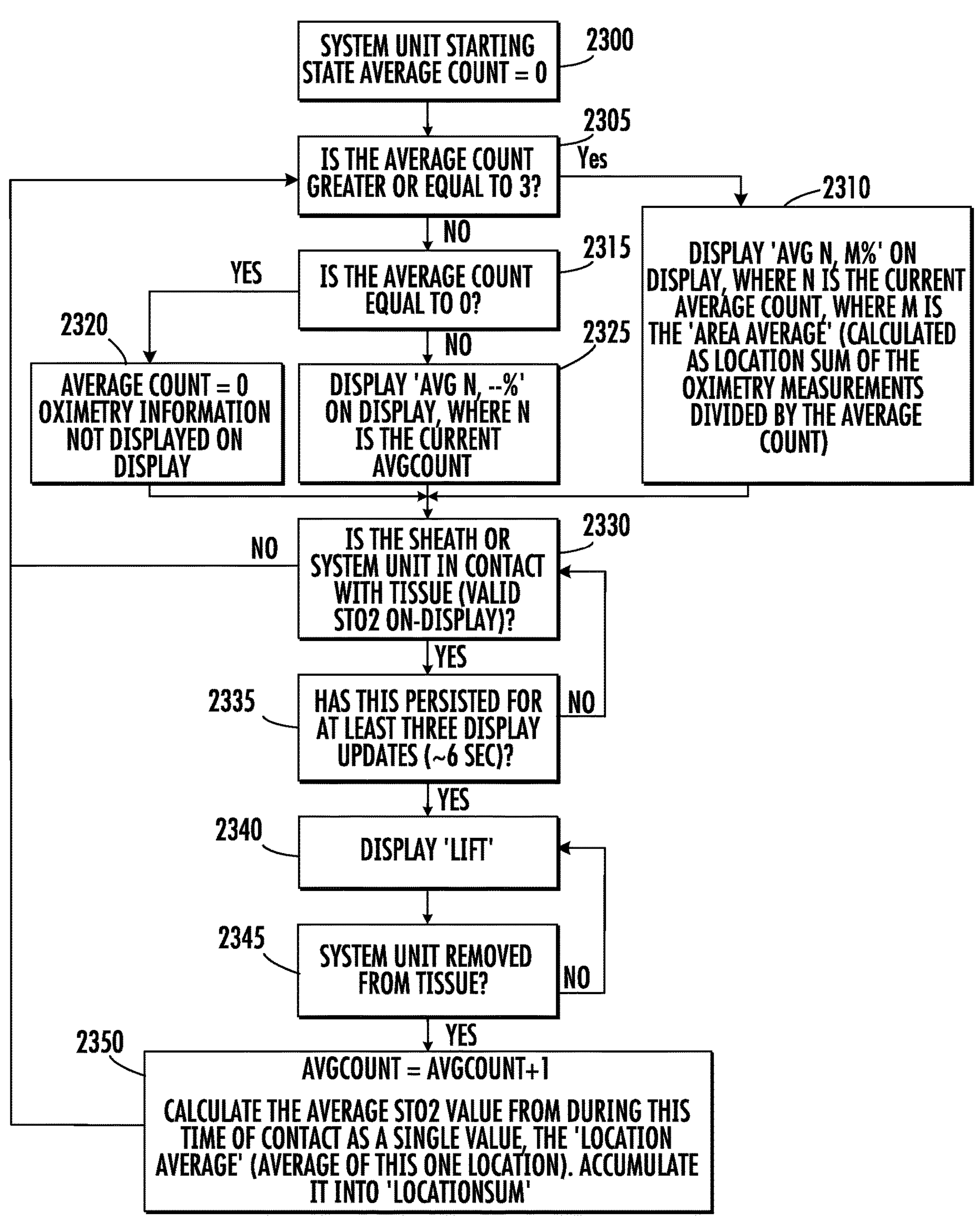
FIG. 16 is a flow diagram of a method of operation of the system unit for generating average oximetry information, in an implementation.

FIG. 16 is a flow diagram of a method of operation of the system unit for generating average oximetry information, in an implementation. The flow diagram shows an example embodiment in an implementation. Steps may be added, removed, or combined without deviating from the method.

At 2300, at an initial state of the method, no oximetry measurements (i.e., "average count") have been made for tissue to be measured of a single patient. For each tissue location that oximetry measurements are made, the average count may be incremented by one if a set of lift and place rules of the system unit are satisfied or may remain unchanged if the set lift and place rules are not satisfied. For example, if the set of rules are satisfied for a first tissue location, then the average count is one. If the set of rules are satisfied for a second tissue location, then the average count is incremented by one and is two. If the set of rules are satisfied for a third tissue location, then the average count is incremented by one and is three. If the set of rules are satisfied for a fourth tissue location, then the average count is incremented by one and is four. If the set of rules are satisfied for a fifth tissue location, then the average count is incremented by one and is five. If the set of rules are satisfied for a sixth tissue location, then the average count is incremented by one and is six. This process of incrementing the average count continues to increment by one for each subsequent tissue location that the system unit is placed at if the set of rules is satisfied.

If the lift and place rules are not satisfied, for example, for the third tissue location, then the average count is not incremented by one, and the average count may remain at two. The lift and placement rules used by the system unit to increment the average count or not increment the average count are described with respect to the following steps of the method.

In an embodiment, the values for the average count are stored in a memory (e.g., a buffer memory) of the system. The stored value for the average count is incremented when the lift and place set of rules are satisfied for tissue oximetry measurements for the tissue locations of the patient tissue of the select patient.

At 2305, the system unit interrogates the memory (e.g., the buffer memory) of the system unit to determine whether the average count is greater than or equal to three. If the average count is greater than or equal to three, then oximetry measurements have been made for three tissue locations of the patient tissue and the lift and place rules have been satisfied for the measurements made by the system unit. If the average count is less than three, then oximetry measurements have not been made for three tissue locations of the patient tissue and, lift and place rules have been satisfied for the measurements made by the system unit, or both.

At 2305, if the average count is greater than or equal to three (e.g., interrogate the memory that stores the average count), then at 2310 the display of the system unit displays the current average count and average information for the oximetry measurements (e.g., average oxygen saturation measurements) for the tissue locations. More specifically, the system unit may display "Avg N, M %" (see FIG. 15 on the display, where N is the current average count and M is the average of the oximetry measurements. The average is calculated as the sum of the oximetry measurements divided by the average count. In alternative implementations, the average is calculated by other techniques.

At 2305, if the average count is less than three, then at 2315, the system unit determines whether the average count is equal to zero.

At 2315, if the average count is zero, then at 2320, the system unit does not display oximetry information on the display.

At 2315, if the average count is greater than zero, then at 2325, the system unit displays the current average count and no average information for the oximetry measurements. For example, the system unit may display "Avg N, --%" (see FIG. 14) on the display, where N is the average count and the dashes indicate that no average information for the oximetry information is displayed. The display may display the two dashes or other text or another icon to indicate that no average for the oximetry measurement is displayed.

At 2330, the system unit makes one or more oximetry measurements for a tissue location. If the system unit is executing the method for a first time, the tissue location is a first tissue location. If the system unit is executing the method for a second time, the tissue location may be a second tissue location. If the system unit is executing the method for a third time, the tissue location may be a third tissue location. The tissue locations increase as the method continues to be executed (loop through the loop portions of the method). The system unit determines whether the sheath or system unit (e.g., system unit used without the sheath) contacts the tissue and whether the oximetry information (e.g., oxygen saturation information) for the oximetry measurement is valid oximetry information. The system unit will display the oximetry information if the oximetry information is valid oximetry information.

At 2330, if the sheath or system unit is not in contact with the tissue, if the oximetry information is not valid, or both, then the method return to step 2305 and repeats the described steps until the method is terminated, such as by inversion of the system unit described below with respect to FIGS. 21 and 22A-22B.

At 2330, if the sheath or system unit is in contact with the tissue, if the oximetry information is valid, or both, then at 2335, the system unit determines whether this state (e.g., if the sheath or system unit is in contact with the tissue, if the oximetry information is valid, or both) has persisted for at least three display update cycles. The display may update the oximetry information that is displayed on the display after one update cycle that has a threshold cycle time. The threshold cycle time may be from about 1 second to about 3 seconds, from about 2 seconds and 4 seconds, or another duration. In an implementation, the threshold cycle time is from about 2 seconds to 2.3 seconds. Thus, three update cycle times may be from about 3 seconds to about 9 seconds, about 6 seconds to about 12 seconds, or another duration. In the specific embodiment, three update cycles may be about 6 seconds.

At 2335, if the state (e.g., if the sheath or system unit is in contact with the tissue, if the oximetry information is valid, or both) has not persisted for at least three display update cycles, then the system unit continues to make oximetry measurements for the tissue location at 2330.

At 2340, if the state (e.g., if the sheath or system unit is in contact with the tissue, if the oximetry information is valid, or both) has persisted for at least three display update cycles, then the system unit displays a use message (e.g., a "lift up" message) on the display at 2340. The use message informs the user that the user has to take a specific action with the system unit so that the system unit can accumulate an average of oximetry measurements.

At 2345, the system unit determines whether the sheath or system unit has been lifted, such as if the system unit has been lifted out of contact with the tissue.

In an implementation, the lift is detected by determining that measured oximetry information is no longer valid for the patient tissue. Invalid oximetry information may be outside of a range of predetermined valid oximetry information. Invalid oximetry information may include an oxygen saturation measurement that provides an invalid result, for example, from extreme property predictions, a poor fit of measured values to a lookup database of stored Monte Carlo simulated reflectance curves, ambient light saturation (e.g., when the system unit is lifted from tissue, or other factors.

When the system unit detects that a lift has occurred, the system unit determines whether the lift occurred when the lift up message was displayed on the display. The system unit may store oximetry information in a memory location in which the average oximetry information is stored. The system unit may also store information (e.g., the average count) for the number of times oximetry information is stored for the average oximetry information.

At 2345, if the system unit has not been removed from the tissue, has been removed from the tissue when the use message is not displayed, or both, then the lift message is displayed at 2340.

At 2345, if the system unit has been removed from the tissue, has been removed from the tissue when the use message is displayed, or both, then at 2350 the average count is incremented by one. The average for the oximetry information (e.g., oxygen saturation value) is generated for the tissue locations. The incremented average count and the average oximetry information is displayed on the display. Thereafter, the flow of the method repeats at 2305.

Table A below shows information that is used by the system unit to generate an average for oximetry information, in an implementation. The table shows a number of oximetry measurements that may be made when the sheath or system unit is placed in contact with various locations on a patient's tissue. The values of Table A may be generated according to the method described above with respect to FIG. 16 and alternatives of FIG. 16 also described above.

The first column in the table, labeled "Number of measurements included in an average," shows the number of times the sheath or system unit has been removed from the tissue while the user message (e.g., "lift up") is displayed on the display. For example, the number 1 entry in the first column of the table may be for an initial lift up of the sheath or system unit for a first tissue location for a new average. The number 2 entry in the first column of the table may be for a lift up of the sheath or system unit from a second tissue location when the sheath or system unit has been lifted from the first tissue location and lifted from the second tissue location. The number 3 entry in the first column of the table may be for a third lift up of the sheath or system unit from a third tissue location when the sheath or system unit has been lifted from the second tissue location and lifted from the third tissue location. The number 4 entry in the first column of the table may be for a fourth lift up of the sheath or system unit from a fourth tissue location when the sheath or system unit has been lifted from the third tissue location and lifted from the fourth tissue location.

The second column in the table, labeled "Oximentry measurements during a placement of the sheath and system unit at a tissue location," shows a number of pieces of oximetry information (e.g., oxygen saturation values) that are generated when the sheath or system unit is placed at a location on a patient's tissue. For example, the first row of oximetry information of the second column shows six values (e.g., 27, 50, 74, 66, 79, 72) for oximetry information generated by the system unit for the first tissue location. The second row of oximetry information of the second column shows four values (e.g., 62, 71, 77, 68) for oximetry information generated by the system unit for the second tissue location. The second tissue location is the location where the second window of the sheath or the probe face of the system unit is placed after being lifted from the first tissue location. The third row of oximetry information in the second column shows five values (e.g., 0, 0, 64, 73, 70) for oximetry information generated by the system unit for the third tissue location. The third tissue location is the location where the second window of the sheath or the probe face of the system unit is placed after being lifted from the second tissue location. The fourth row of oximetry information in the second column shows four values (e.g., 0, 0, 64, 73, 70) for oximetry information generated by the system unit for the fourth tissue location. The fourth tissue location is the location where the second window of the sheath or the probe face of the system unit is placed after being lifted from the third tissue location.

The last piece of oximetry information generated for each of the tissue locations is used by the system unit to generate an average of the oximetry information. For example, the third column, labeled "Measurements used for average," of the table shows the measurements that are used for generating an average. The first data row of the third column includes the value 72 for the oximetry information. This value is the last piece of oximetry information (e.g., 72) generated by the system unit for the first tissue location, which is shown in the second column of the table.

The second data row of the third column includes the value 68 for the oximetry information. This value is the last piece of oximetry information (e.g., 68) generated by the system unit for the second tissue location, which is shown in the second column of the table.

The third data row of the third column includes the value 70 for the oximetry information. This value is the last piece of oximetry information (e.g., 70) generated by the system unit for the third tissue location, which is shown in the second column of the table. The fourth data row of the third column includes the value 74 for the oximetry information. This value is the last piece of oximetry information (e.g., 74) generated by the system unit for the fourth tissue location, which is shown in the second column of the table.

The fourth column in the table shows average values that may be displayed on the display of the system unit. In an implementation, an average value for the first and second tissue locations is not shown on the display. In an implementation, an average value for the first tissue location is not shown on the display, while an average for a second or higher number of tissue locations is displayed on the display. As described above, the display may display dashed lines or another icon for the average value for the first and second tissue locations. When the average values are generated for the third tissue location or a higher number tissue location, these average values may be displayed on the display.

TABLE A

| Number of measurements included in an average | Oximetry measurements during a placement of the sheath and system unit at a tissue location | Measurements used for average | Average |
|---|---|---|---|
| 1 | 27, 50, 74, 66, 79, 72 | 72 | — |
| 2 | 62, 71, 77, 68 | 68 | — |
| 3 | 0, 0, 64, 73, 70 | 70 | 70 |
| 4 | 55, 0, 20, 74 | 74 | 71 |

In an implementation, the system unit stores the values in two or more of the columns. The system unit may also store a sum of each of the measurements used for the average shown in column three. For example, after the measurements of the first tissue location are made, the system unit may store the value 72. After the measurements for the first and second tissue locations are made, the system unit may store the sum (e.g., 140) of the first and second values (e.g., 72 and 68) of the third column. After the measurements for the first, second, and third tissue locations are made, the system unit may store the sum (e.g., 210) of the first, second, and third values (e.g., 72, 68, and 70) of the third column. After the measurements for the first, second, third, and fourth tissue locations are made, the system unit may store the sum (e.g., 284) of the first, second, and third values (e.g., 72, 68, 70, and 74) of the third column. Fewer values may be included in the stored sum if the use message (e.g., "lift up") is not displayed when the sheath or system unit is lifted from the tissue as described above with respect to FIG. 16.

In an implementation, an average can be reset and a new average can be initiated when the system unit is rotated through one or more predetermined angles and about a predetermined axis. For the reset to occur, the system unit can be vertically rotated where the display of the system unit is rotated down as the probe face of the system unit is rotated up. That is, the system unit can be rotated vertically as indicated by arrows 1830 in FIG. 11. The rotation can be about any horizontal axis 1820 that is perpendicular to vertical axis 1810. Vertical axis can 1810 extends through the probe face of the system unit and the display of the system unit.

Figure 22A:
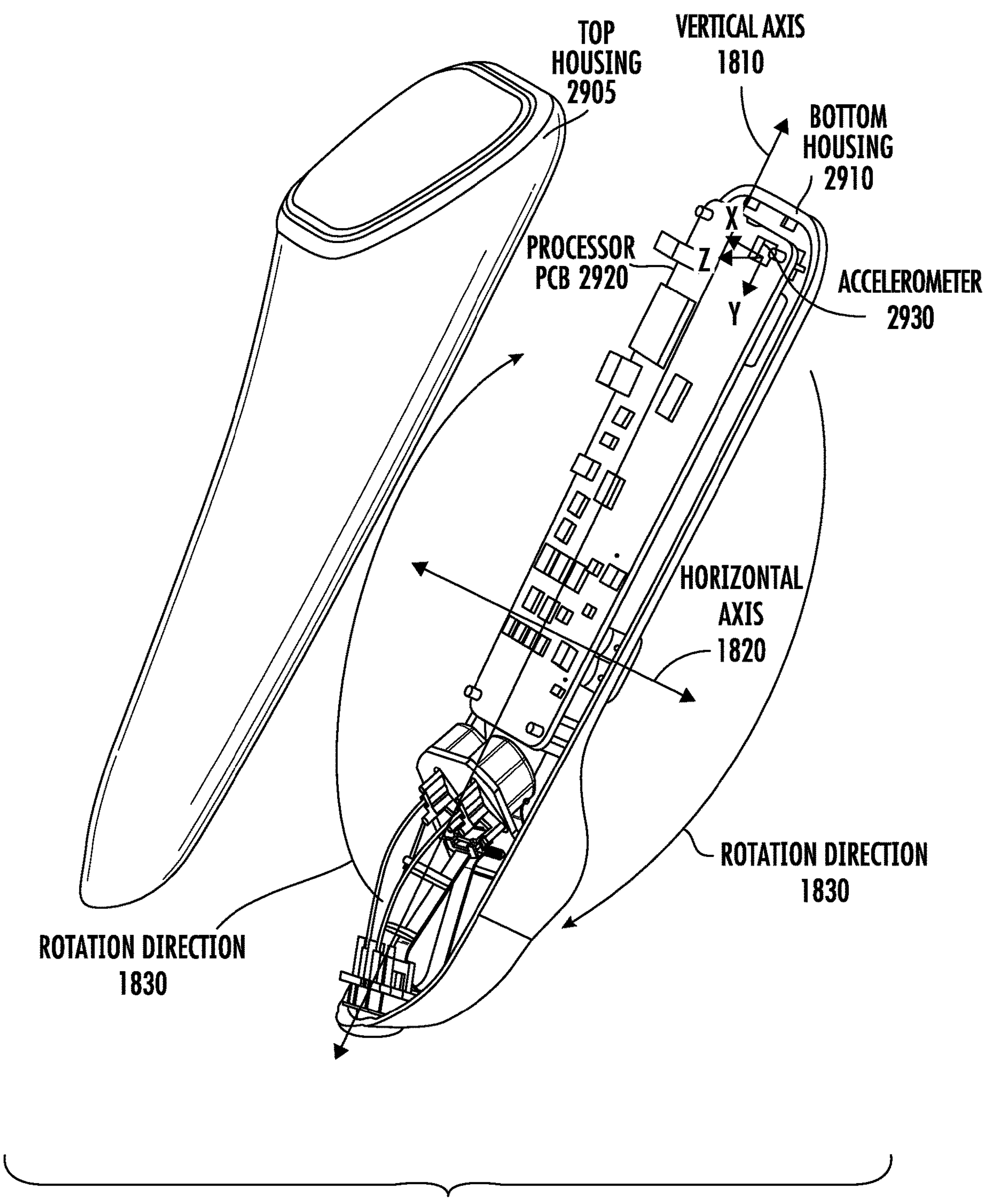
FIG. 22A shows the system unit with the top housing separated from the bottom housing.

FIG. 22A shows the system unit with the top housing 2905 separated from the bottom housing 2910. In an embodiment, the vertical axis 1810 is parallel to a surface of a printed circuit board (PCB) 2920 that is located in the system unit. The surface of the PCB is the surface on which the accelerometer circuit 2930 and other circuits of the system unit are mounted. The PCB is approximately parallel to a back surface of the bottom housing, which the PCB is mounted on.

The accelerometer can be an integrated circuit (IC), in an implementation, where the accelerometer is mounted on PCB 2920. The accelerometer can be mounted on the top surface of the PCB as shown in FIG. 22A or can be mounted on the bottom surface of the PCB. The accelerometer IC can be mounted on a PCB with a number of support circuits where the PCB is mounted on PCB 2920. The accelerometer is a three-axis accelerometer, in one implementation. The accelerometer is a two axis accelerometer, in another implementation. The accelerometer can include two, two axis accelerometers, in an implementation.

In an implementation where the accelerometer is a three axis accelerometer, the z-axis of the accelerometer is perpendicular to the top surface of PCB 2920 and extends upward from the top surface of the PCB as shown in FIG. 22. That is, the z-axis extends towards the top housing and the display of the system unit. The z-axis can extend towards bottom housing 1810, such as in an implementation where the accelerometer is mounted on the bottom surface of PCB 2920.

The y-axis of the accelerometer extends along a vertical axis 1810 of the accelerometer or is parallel to vertical axis 1810. The y-axis can extend through the probe face of the sensor head or adjacent to the probe face.

In an implementation, the x-, y-, and z-axis are oriented in directions other than described above, such as the y-axis not being parallel to the to vertical axis 1810 or the z-axis not extending toward the bottom housing and where the processor is configured to use one or more axis and mathematical calculation (e.g., trigonometry) to determine when the system unit is rotated, such as being rotated with respect to the acceleration of gravity vector. Those of skill in the art will understand the use of mathematical calculations for determining such rotations when the axis of the accelerometer are oriented in a variety of directions.

The x-axis of the accelerometer extends to the left when the top housing is viewed from the front or when the front surface of PCB 2920 is viewed as shown in FIG. 22. The x-axis can extend to the right when the accelerometer is mounted on the back surface of PCB 2920. The three axes of the accelerometer can be indicated on the IC packaging, on the PCB, or both. The axes can be indicated by arrows, a first mark (e.g., circle with a cross inside the circle) that indicates that an axis is extending into the PCB, or a second mark (e.g., circle with a dot inside the circle) indicating an axis is extending upward from the PCB. In an implementation, the accelerometer is manufactured by NXP Semiconductors N.V. of Austin Tex. and is a model MMA8452QR1.

Figure 22B:
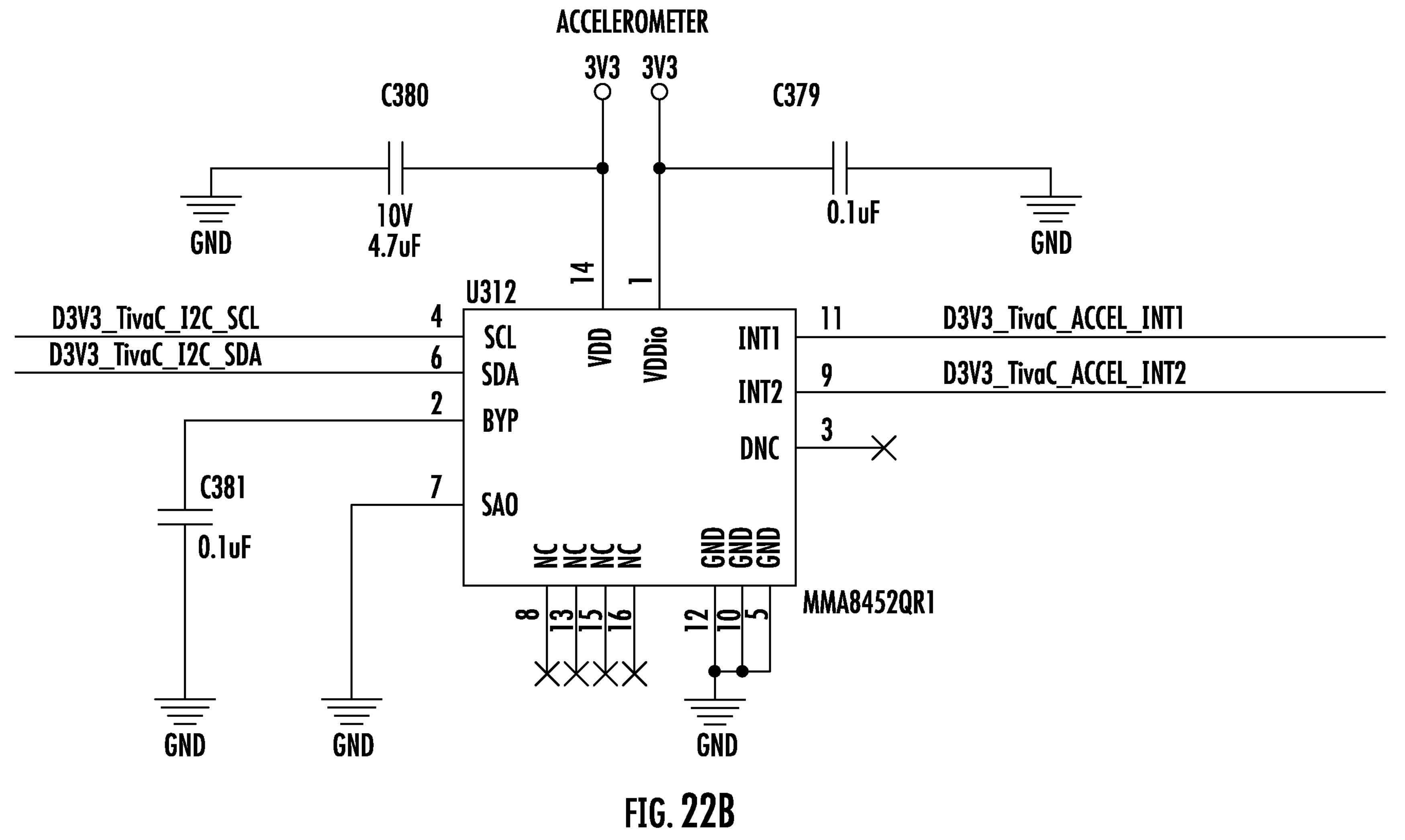
FIG. 22B shows a diagram of an accelerometer, in an implementation.

FIG. 22B shows a diagram of an accelerometer MMA8452QR1. The accelerometer is configured to provide serial data output (SDA) for determined accelerations. The accelerometer is a clocked device (SCL) that is configured for clocking data out of the serial data output. The device is configured to allow for an interrupt (INT1 and INT2) to allow a processor to control when serial data is provided from the SDA so that the processor does not have to continuously monitor the accelerometer for output. The INT1 and INT2 are user programmable to configured interrupt control for the processor.

In an implementation, the accelerometer outputs digital data to indicate the orientation of the axes with respect to the direction of the acceleration of gravity vector. For example, if an axis (e.g., positive y-axis) is in the direction of the of acceleration of gravity vector, the accelerometer can output a first value (e.g., +1000) to indicate this direction of the axis. For example, if the axis (e.g., positive y-axis) is in the opposite direction of the of acceleration of gravity vector, the accelerometer can output a second value (e.g., −1000) to indicate this direction of the axis where the first value might be a positive value and the second value might be a negative value. Those of skill in the art will realize other values that can be output by the accelerometer to indicate alignment and antialignment with the acceleration of gravity vector. Values for the orientation of the x-axis and z-axis can similarly be output by the accelerometer. In an implementation for vertical rotation 1839 of the system unit as shown in FIG. 11, output from the accelerometer for only one axis (e.g., y-axis) is monitored and used by the processor to determine whether the system unit is being vertically rotated with respect to the acceleration of gravity vector. The processor can be configured to monitor the value output for the accelerometer for a given axis (e.g., +1000 for the y-axis) to determine whether the system unit is being rotated. The processor can compare the value output (e.g., −1000 for the y-axis for a 180 degree rotation from vertical, sensor head down and top up) by the accelerometer to the maximum value output (e.g., +1000 for the y-axis) to determine the real-time angular orientation of the accelerometer. A history of the output of the accelerometer might not be stored used to detect past angular orientation of the system unit.

An average can be reset when the average number is reset (e.g., reset in memory, reset on the display, or both). New oximetry measurement information for one or more tissue locations can be stored in the memory for a new average. In an implementation, the memory storing the average information can be reset.

For the reset to occur the system unit can be rotated through a first angle downward (e.g., the display is rotated down and the probe face is rotated up). Thereafter, the system unit can be rotated through a second angle upward (e.g., the display is rotated up and the probe face is rotated down). The first and second angles can be different angles to that the reset occurs according to a hysteresis process. That it, a reset can occur after the downward rotation, but a second reset will not occur after the subsequent upward rotation.

Figure 21:
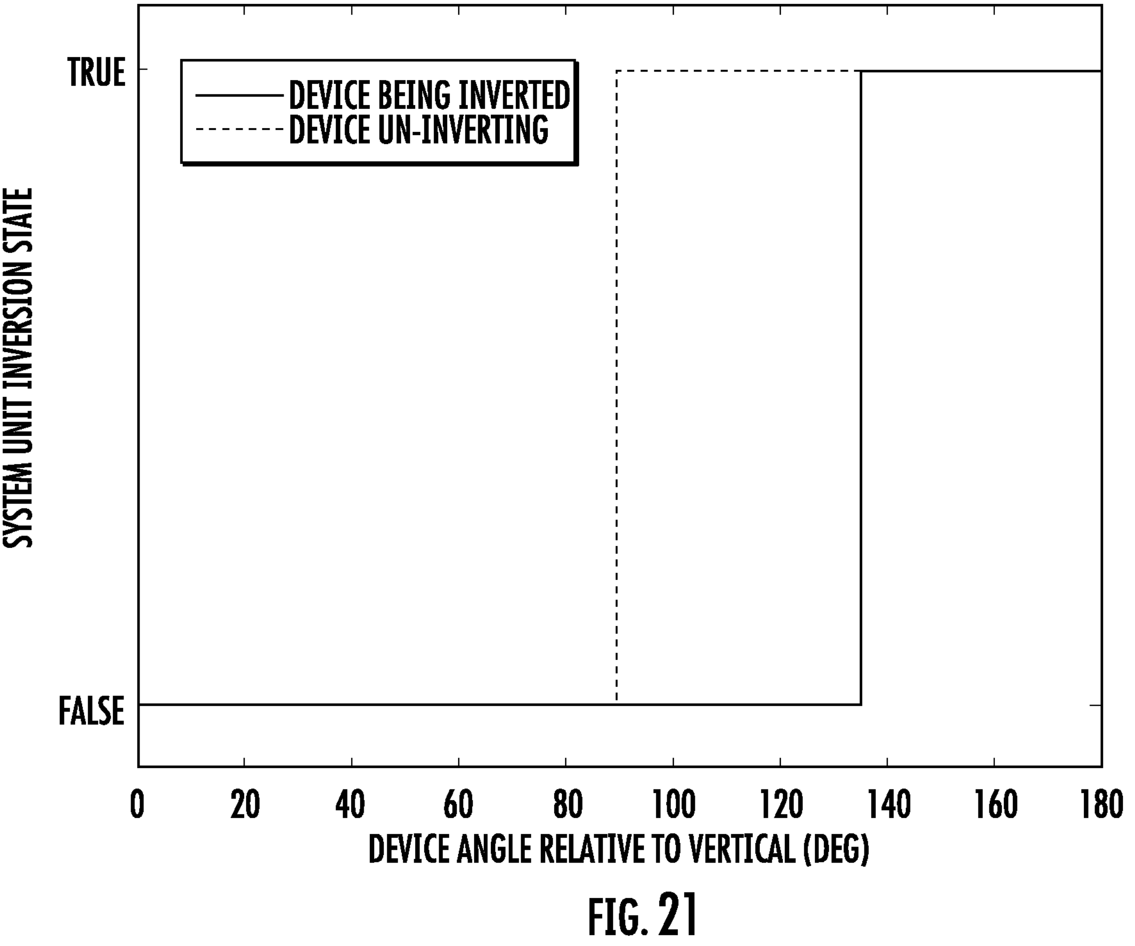
FIG. 21 is a graph showing the first rotation angle and the second rotation angle that the system unit may be vertically rotated by to affect the average reset.

FIG. 21 is a graph showing the first rotation angle and the second rotation angle that the system unit may be vertically rotated by to affect the average reset. The first angle is represented by the solid line in the graph and identified in the graph's legend as "Device being inverted," (e.g., the display is rotated down and the probe face is rotated up). The system unit being inverted is sometimes referred to as the system unit being "dipped." The first angle may be from about 130 degrees to about 150 degrees. In an embodiment, the first angle is 135 degrees. The second angle is represented by the dashed line in the graph and identified in the graph's legend as "Device being un-inverting," (e.g., the display is rotated up and the probe face is rotated down). The accelerometer of the system unit may be configured to detect vertical rotations. The accelerometer may not be configured to determine whether the device is oriented upright (e.g., display of the system unit oriented up and the probe face oriented down) or oriented down (e.g., display of the system unit oriented down and the probe face oriented up). By configuring the system to detect the system unit being rotated down at the first angle and being rotated up at the second angle, the system unit can use motion detection detected by the accelerometer and the hysteresis to determine whether the system unit is being rotated up or rotated down.

Figure 17:
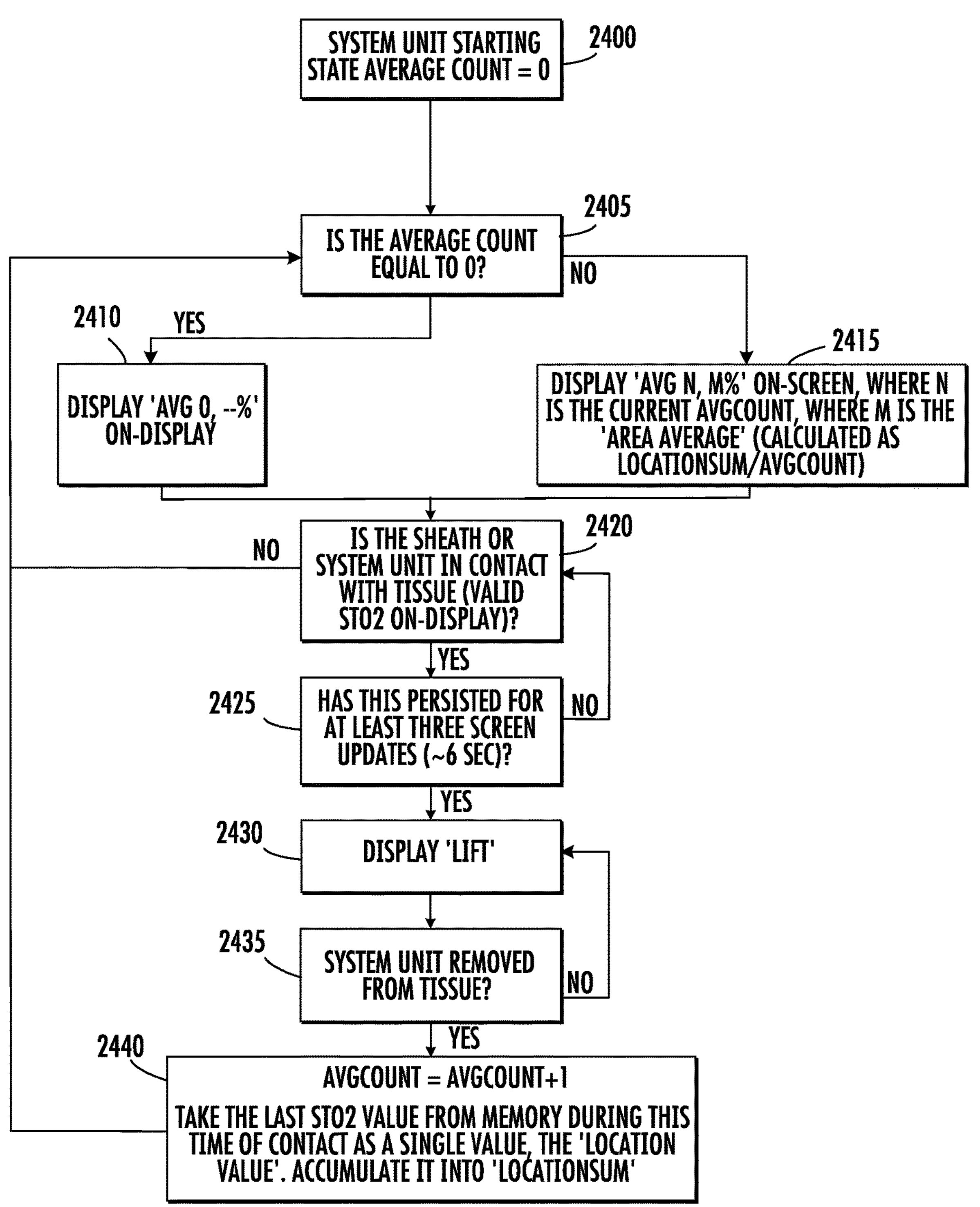
FIG. 17 is a flow diagram of a method of operation of the system unit for generating average oximetry information, in an implementation.

FIG. 17 is a flow diagram of a method of operation of the system unit for generating average oximetry information, in an implementation. The flow diagram shows an example embodiment in an implementation. Steps may be added, removed, or combined without deviating from the method.

At 2400, at an initial state of the method, no oximetry measurements (i.e., "average count") have been made for tissue to be measured of a single patient. For each tissue location that oximetry measurements are made, the average count may be incremented by one if a set of lift and place rules of the system unit are satisfied or may remain unchanged if the set lift and place rules are not satisfied. For example, if the set of rules is satisfied for a first tissue location, then the average count is one. If the set of rules is satisfied for a second tissue location, then the average count is incremented by one and is two. If the set of rules is satisfied for a third tissue location, then the average count is incremented by one and is three. If the set of rules is satisfied for a fourth tissue location, then the average count is incremented by one and is four. If the set of rules is satisfied for a fifth tissue location, then the average count is incremented by one and is five. If the set of rules is satisfied for a sixth tissue location, then the average count is incremented by one and is six. This process of incrementing the average count continues to increment by one for each subsequent tissue location that the system unit is placed at if the set of rules is satisfied.

If the lift and place rules are not satisfied, for example, for the third tissue location, then the average count is not incremented by one, and the average count may remain at two. The lift and placement rules used by the system unit to increment the average count or not increment the average count are described with respect to the following steps of the method.

In an embodiment, the values for the average count are stored in a memory (e.g., a buffer memory) of the system. The stored value for the average count is incremented when the lift and place set of rules are satisfied for tissue oximetry measurements for the tissue locations of the patient tissue of the select patient.

At 2405, the system unit interrogates the memory (e.g., the buffer memory) of the system unit to determine whether the average count is greater than zero or equal to zero. If the average count is greater than zero, then an oximetry measurement has been made for at least one tissue location of the patient tissue and the lift and place rules have been satisfied for the measurements made by the system unit. If the average count is zero, then no oximetry measurements have been made.

At 2405, if the average count is greater than zero (e.g., interrogate the memory that stores the average count), then at 2410 the display of the system unit displays the current average count and average information for the oximetry measurements (e.g., average oxygen saturation measurements) for the tissue locations. More specifically, the system unit may display "Avg N, M %" (see FIG. 15) on the display, where N is the current average count and M is the average of the oximetry measurements, which are calculated as the sum of the oximetry measurements divided by the average count.

At 2405, if the average count is zero, then at 2415, the system unit displays the current average count and no average information for the oximetry measurements. For example, the system unit may display "Avg 0, --%" (see FIG. 14) on the display, where N is the average count and the dashes indicate that no average information for the oximetry information is displayed. The display may display the two dashes or other text or another icon to indicate that no average for the oximetry measurement is displayed.

At 2420, the system unit makes one or more oximetry measurements for a tissue location. If the system unit is executing the method for a first time, the tissue location is a first tissue location. If the system unit executes the method for a second time, the tissue location may be a second tissue location. If the system unit executes the method for a third time, the tissue location may be a third tissue location. The tissue locations increase as the method continues to be executed (loop through the loop portions of the method). The system unit determines whether the sheath or system unit (e.g., system unit used without the sheath) contacts the tissue and whether the oximetry information (e.g., oxygen saturation information) for the oximetry measurement is valid oximetry information. The system unit will display the oximetry information if the oximetry information is valid oximetry information.

At 2420, if the sheath or system unit is not in contact with the tissue, if the oximetry information is not valid, or both, then the method return to step 2405 and repeats the described steps until the method is terminated, such as by inversion of the system unit described above with respect to FIGS. 21 and 22A-22B.

At 2420, if the sheath or system unit is in contact with the tissue, if the oximetry information is valid, or both, then at 2425, the system unit determines whether this state (e.g., if the sheath or system unit is in contact with the tissue, if the oximetry information is valid, or both) has persisted for at least three display update cycles. The display may update the oximetry information that is displayed on the display after one update cycle that has a threshold cycle time. The threshold cycle time may be from about 1 second to about 3 seconds. In an implementation, the threshold cycle time is about 2 seconds. Thus, three update cycle times may be from about 3 seconds to about 9 seconds. In the specific embodiment, three update cycles may be about 6 seconds.

At 2425, if the state (e.g., if the sheath or system unit is in contact with the tissue, if the oximetry information is valid, or both) has not persisted for at least three display update cycles, then the system unit continues to make oximetry measurements for the tissue location at 2420.

At 2425, if the state (e.g., if the sheath or system unit is in contact with the tissue, if the oximetry information is valid, or both) has persisted for at least three display update cycles, then the system unit displays a use message (e.g., a "lift up" message) on the display at 2430. The use message informs the user that the user has to take a specific action with the system unit so that the system unit can accumulate an average of oximetry measurements.

At 2435, the system unit determines whether the sheath or system unit has been lifted, such as if the system unit has been lifted out of contact with the tissue.

In an implementation, the lift is detected by determining that measured oximetry information is no longer valid for the patient tissue. Invalid oximetry information may be outside of a range of predetermined valid oximetry information. Invalid oximetry information may include an oxygen saturation measurement that provides an invalid result, for example, from an extreme property prediction, a poor fit of measured values to a lookup database of stored Monte Carlo simulated reflectance curves, ambient light saturation (e.g., when the system unit is lifted from tissue, or other factors.

When the system unit detects that a lift has occurred, the system unit determines whether the lift occurred when the lift up message was displayed on the display. The system unit may store oximetry information in a memory location in which the average oximetry information is stored. The system unit may also store information (e.g., the average count) for the number of times oximetry information is stored for the average oximetry information.

At 2435, if the system unit has not been removed from the tissue, has been removed from the tissue when the use message is not displayed, or both, then the lift message is displayed at 2430.

At 2445, if the system unit has been removed from the tissue, has been removed from the tissue when the use message is displayed, or both, then at 2440, the average count is incremented by one. The average for the oximetry information (e.g., oxygen saturation value) is generated for the tissue locations. The incremented average count and the average oximetry information is displayed on the display. Thereafter, the flow of the method repeats at 2405.

Table B below shows information that is used by the system unit to generate an average for oximetry information, in an implementation Similar to Table A above, Table B includes columns for the "Number of measurements included in an average," "Oximetry measurements during a placement of the sheath and system unit at a tissue location," "Measurements used for average," and "Average." Table B differs from Table A in that the average values shown in the fourth column are displayed on the display. The values of Table B may be generated according to the method described above with respect to FIG. 17 and alternatives of FIG. 17 also described above.

TABLE B

| Number of measurements included in an average | Oximetry measurements during a placement of the sheath and system unit at a tissue location | Measurements used for average | Average |
|---|---|---|---|
| 1 | 27, 50, 74, 66, 79, 72 | 72 | 72 |
| 2 | 62, 71, 77, 68 | 68 | 70 |
| 3 | 0, 0, 64, 73, 70 | 70 | 70 |
| 4 | 55, 0, 20, 74 | 74 | 71 |

Figure 18:
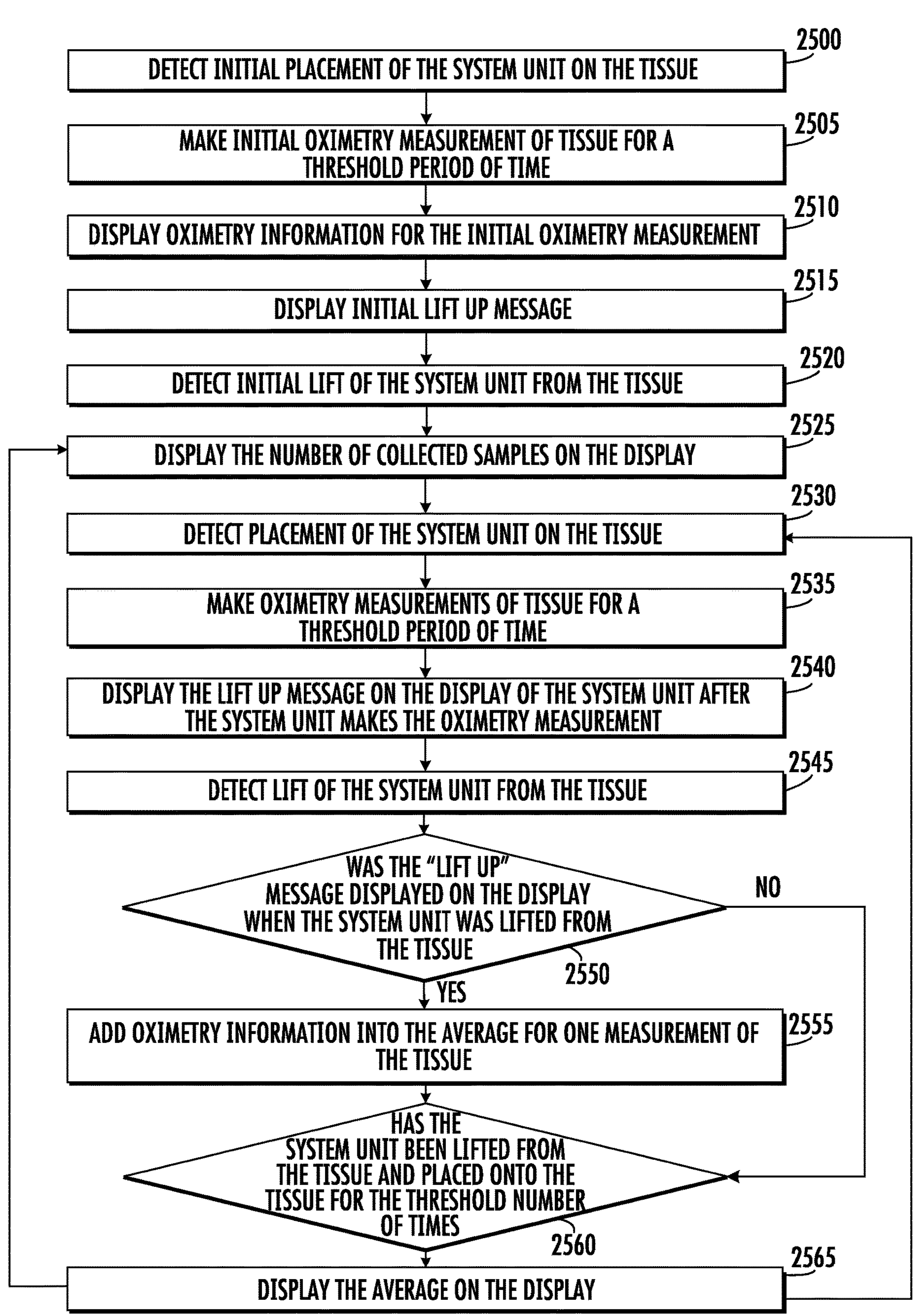
FIG. 18 is a flow diagram of a method of operation of the system unit for generating average oximetry information, in an implementation.

FIG. 18 is a flow diagram of a method of operation of the system unit for generating average oximetry information, in an implementation. The flow diagram shows an example embodiment in an implementation. Steps may be added, removed, or combined without deviating from the method.

At 2500, the second sheath window of the sheath or the probe face of the probe tip of the system unit (e.g., if used without the sheath) is initially placed into contact with patient tissue by a user at a first tissue location.

At 2505, the system unit makes a first oximetry measurement of the patient tissue and generates first oximetry information. The system unit may store the determined oximetry information in one of the memories of the system unit, such as the system unit RAM 312. This first oximetry information may be stored in a memory location in which the average oximetry information is stored.

At 2510, the display of the system unit displays the first oximetry information (e.g., oxygen saturation) that is determined by the system unit.

At 2515, after the first oximetry measurement is performed for a threshold period of time, the use message (e.g., "lift up" message) is displayed on the display. The threshold period of time may be about 1 to about 10 seconds. In an implementation, the threshold period of time is 5 seconds.

At 2520, the system unit detects that the user has initially lifted the sheath, system unit, or both from the tissue. In an implementation, the lift is detected by determining that measured oximetry information is no longer valid for the patient tissue. Invalid oximetry information may be outside of a range of predetermined valid oximetry information. Invalid oximetry information may include an oxygen saturation measurement that provides an invalid result, for example, from an extreme property prediction, a poor fit of measured values to a lookup database of stored Monte Carlo simulated reflectance curves, ambient light saturation (e.g., when the system unit is lifted from tissue, or other factors.

When the system unit detects that a lift has occurred, the system unit then determines whether the lift occurred when the lift message was displayed. The system unit may then store the first oximetry information in a memory location in which the average oximetry information is stored. The system unit may also store information (e.g., the average count number) for a number of times oximetry information is stored for the average oximetry information. At the current step of the method, the number of stored pieces of oximetry information is one.

At 2525, the number of times that the oximetry information is stored for the average oximetry reading is displayed on the display. Referring to FIG. 14, the number of times that the oximetry information is stored for the average oximetry reading is 1. When the number of times that the oximetry information is stored is displayed on the display, the average oximetry information may also be displayed. If the number of times that the oximetry information is stored is 1, then the oximetry information is not an average, but is the first oximetry information. In an embodiment, the average oximetry information is not displayed (FIG. 14) on the display until a threshold number (e.g., three, FIG. 15) of pieces of oximetry information are averaged and stored in the memory. The information displayed may be two dashes or a different icon.

At 2530, the system unit detects that the second window of the sheath or the probe face of the probe tip of the system unit is placed back into contact with the patient tissue. The location on the patient tissue may be the first tissue location associated with step 2500 or may be a different tissue location (i.e., a second tissue location). The system unit may then detect contact with the patient tissue by generating valid oximetry information that is in the range of predetermined valid oximetry information.

At 2535, the system unit makes another oximetry measurement (e.g., a second oximetry measurement) of the patient tissue and generates additional oximetry information (e.g., second oximetry information) for the threshold period of time. The system unit may store the additional oximetry information in the system unit memory. The display of the system unit may display the oximetry information (e.g., oxygen saturation) that is determined by the system unit. In an implementation, the system unit does not display the oximetry information.

At 2540, after the oximetry measurement of step 2535 is performed for the threshold period of time, the use message (e.g., "lift up" message) is displayed on the display.

At 2545, the system unit detects that the user has lifted the sheath, system unit, or both from the tissue.

At 2550, if the system unit determines that the use message (e.g., "lift up") was displayed on the display when the sheath, system unit, or both are lifted from the tissue, the additional oximetry information (e.g., the second oximetry information) is added to the prior generated oximetry information (e.g., the first oximetry information) and is stored in the memory. The system unit may generate the average of the summed oximetry information. At the current step of the method, the first and second oximetry information are averaged and stored in the memory.

The system unit may also increment the stored information for the number of times oximetry information is stored for the average oximetry information. At the current step of the method, the number of stored pieces of oximetry information is two. If the sheath, system unit, or both are lifted from the tissue and placed onto the tissue for the threshold number of times (e.g., 3 times), then the system unit displays the average generated at 2555 on the display.

At 2550, if the system unit determines that the use message (e.g., "lift up") was not displayed on the display when the sheath, system unit, or both are lifted from the tissue, the addition oximetry information (e.g., the second oximetry information) is not averaged with the prior stored average oximetry information (e.g., the first oximetry information). That is, step 2555 is skipped. Additionally, the system unit displays the current average for the oximetry information on the display (2565).

At 2565, the method repeats method steps 2530 to 2565 until the user stops the method from executing, such as by inverting the system unit to reset the average oximetry information. For example, the number of times that the sheath, system unit, or both are lifted and placed onto the tissue may be reset to zero.

In an implementation, the method begins at 2525 and proceeds to step 2565 as described above, but the number of collected samples that is displayed on the display may be zero prior to a first oximetry measurement being taken at step 2535 and prior to oximetry information (e.g., an oxygen saturation value) being displayed on the display at step 2565.

In an implementation, the method begins at 2525 and proceeds to step 2565 as described above, but the number of collected samples that is displayed on the display may be one prior to the first oximetry measurement being taken at step 2535 and prior to first oximetry information (e.g., an oxygen saturation value) being displayed on the display at step 2565.

Figure 19:
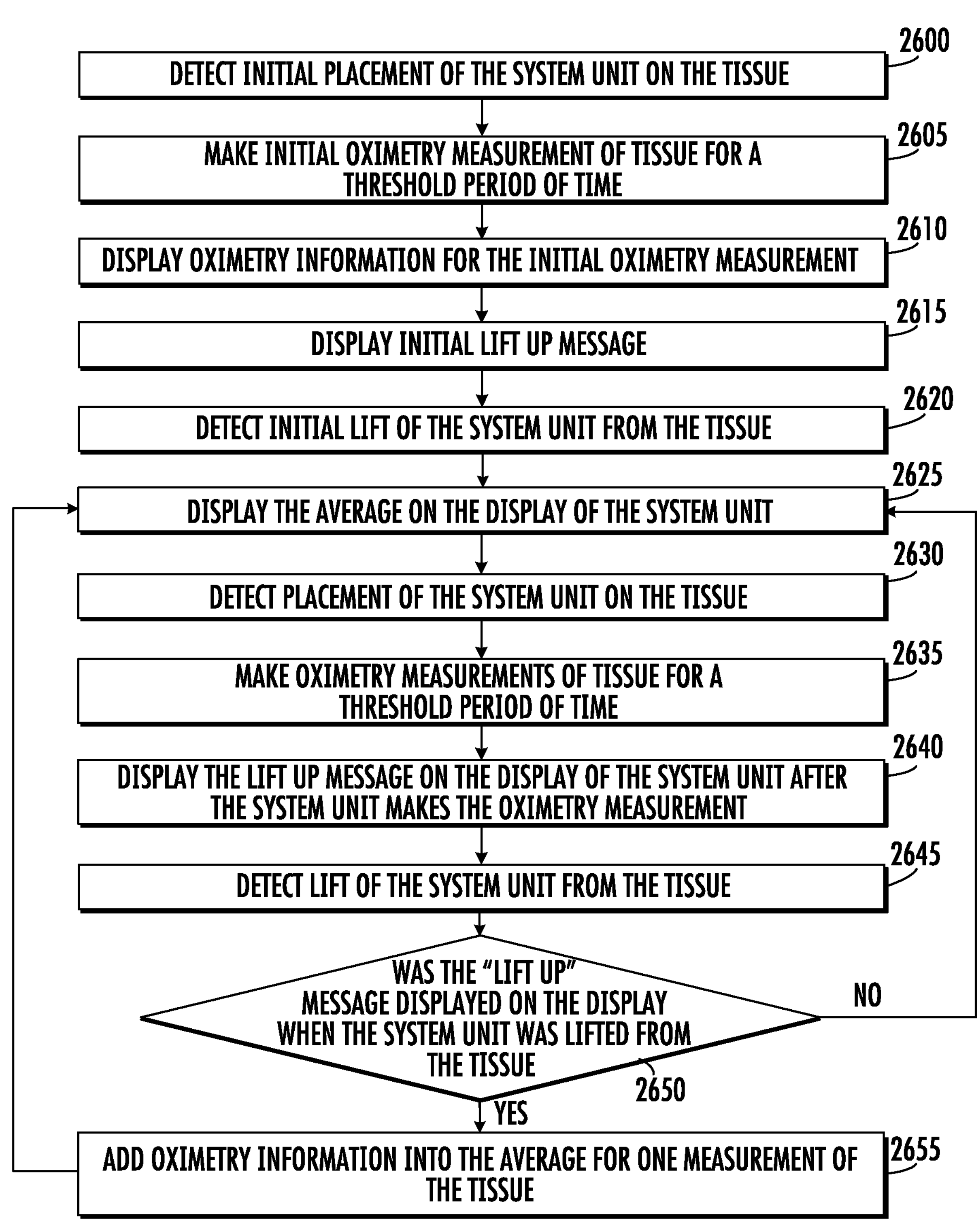
FIG. 19 is a flow diagram of a method of operation of the system unit for generating average oximetry information, in an implementation.

FIG. 19 is a flow diagram of a method of operation of the system unit for generating average oximetry information, in an implementation. The flow diagram shows an example embodiment in an implementation. Steps may be added, removed, or combined without deviating from the method.

At 2600, the second sheath window of the sheath or the probe face of the probe tip of the system unit (e.g., if used without the sheath) is initially placed into contact with patient tissue by a user at a first tissue location.

At 2605, the system unit makes a first oximetry measurement of the patient tissue and generates first oximetry information. The system unit may store the determined oximetry information in one of the memories of the system unit, such as the system unit RAM 312. This first oximetry information may be stored in a memory location in which the average oximetry information is stored.

At 2610, the display of the system unit displays the first oximetry information (e.g., oxygen saturation) that is determined by the system unit.

At 2615, after the first oximetry measurement is performed for a threshold period of time, the use message (e.g., "lift up" message) is displayed on the display. The threshold period of time may be about 1 to about 10 seconds. In an implementation, the threshold period of time is 5 seconds.

At 2620, the system unit detects that the user has initially lifted the sheath, system unit, or both from the tissue. In an implementation, the lift is detected by determining that measured oximetry information is no longer valid oximetry information for the patient tissue. Invalid oximetry information may be outside of a range of predetermined valid oximetry information.

When the system unit detects that a lift has occurred, determines that the lift occurred when the lift message was displayed, or both, the system unit may store the first oximetry information in a memory location in which the average oximetry information is stored. The system unit may also store information (e.g., a number) for a number of times oximetry information is stored for the average oximetry information. At the current step of the method, the number of stored pieces of oximetry information is one.

At 2625, the system unit displays the current average of the oximetry information on the display. The current average may be stored in a memory (e.g., RAM 312) of the system unit and retrieved from the memory for display on the display. If only a first oximetry measurement is taken at 2625, then the displayed oximetry information is for the first oximetry measurement (not an average for a number of lift ups and placements onto tissue) of the tissue. The display may also display the number of oximetry measurements in the current average of the oximetry information. For example, if only a first oximetry measurement is taken at 2625, then the number display is one (FIG. 14); if the first and second oximetry measurements are included in the average, then the number two is displayed; if the first, second, and third oximetry measurements are included in the average, then the number three is displayed; if the first, second, third, and fourth oximetry measurements are included in the average, then the number four is displayed; and the displaying of the numbers of the oximetry measurements included in the average oximetry measurement continues to be incremented for each additional oximetry measurement included in the average.

At 2630, the system unit detects that the second window of the sheath or the probe face of the probe tip of the system unit is placed back into contact with the patient tissue. The location on the patient tissue may be the first tissue location associated with step 2600 or may be a different tissue location (i.e., a second tissue location). The system unit may then detect the contact with the patient tissue by generating valid oximetry information that is in the range of predetermined valid oximetry information.

At 2635, the system unit makes another oximetry measurement of the patient tissue and generates additional oximetry information for the threshold period of time. The system unit may store the additional oximetry information in the system unit memory. The display of the system unit may display the oximetry information (e.g., oxygen saturation) that is determined by the system unit. In an implementation, the system unit does not display the oximetry information.

At 2640, after the oximetry measurement of step 2635 is performed for the threshold period of time, the use message (e.g., "lift up" message) is displayed on the display.

At 2645, the system unit detects that the user has lifted the sheath, system unit, or both from the tissue.

At 2650, if the system unit determines that the use message (e.g., "lift up") was displayed on the display when the sheath, system unit, or both are lifted from the tissue, the addition oximetry information generated at 2635 is averaged with the prior stored average oximetry information (2655). The system unit may also increment the stored information for the number of times oximetry information is stored for the average oximetry information.

At 2650, if the system unit determines that the use message (e.g., "lift up") was not displayed on the display when the sheath, system unit, or both are lifted from the tissue, the addition oximetry information is not averaged with the prior stored average oximetry information. That is, step 2655 is skipped. Additionally, the system unit displays the current average for the oximetry information on the display (2625).

At 2655, the method repeats method steps 2625 to 2655 until the user stops the method from executing, such as by inverting the system unit to reset the average oximetry information. For example, the number of times that the sheath, system unit, or both are lifted and placed onto the tissue may be reset to zero.

In an implementation, the method begins at 2625 and proceeds to step 2655 as described above, but the displayed average at 2625 may be indeterminate before a first oximetry measurement is made by the system unit. After a first oximetry measurement is made by the system unit at 2635, the average may be the first oximetry measurement, after a second oximetry measurement is made by the system unit at 2635, the average may be the average of the first and second oximetry measurements, after a third oximetry measurement is made by the system unit at 2635, the average may be an average of the first, second, and third oximetry measurements. The series of extending the average to include additional oximetry measurements may continue with fourth, fifth, sixth, seventh, eighth, ninth, or more oximetry measurements. The number that is stored for the number of oximetry measurements for the average may be zero at 2625 before a first oximetry measurement is made. The number that is stored for the number of oximetry measurements for the average may be one at 2625 before a first oximetry measurement is made. The system unit may retrieve this number from memory to determine that no valid average oximetry information has been generated. The system unit may display bars, another icon, zero, nothing, or another indicator to indicate that a first oximetry measurement has not yet been made.

Figure 20:
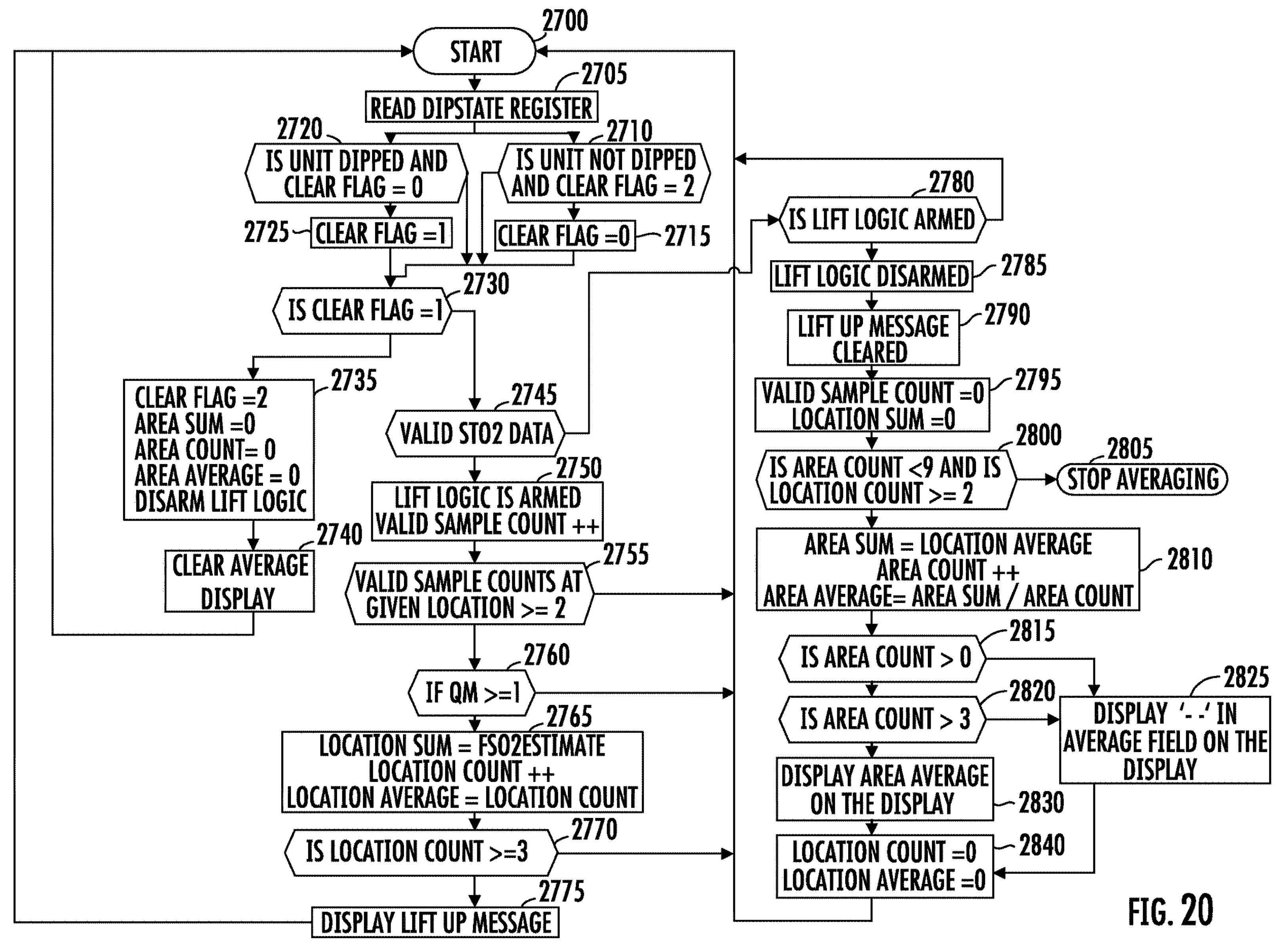
FIG. 20 is a flow diagram of a method of operation of the system unit for generating average oximetry information, in an implementation.

FIG. 20 is a flow diagram of a method of operation of the system unit for generating average oximetry information, in an implementation. The flow diagram shows an example embodiment in an implementation. Steps may be added, removed, or combined without deviating from the method.

At 2700, the second sheath window of the sheath or the probe face of the probe tip of the system unit (e.g., if used without the sheath) is initially placed into contact with patient tissue by a user at a first tissue location. In an implementation, at 2700 valid oximetry measurements have been made by the system unit (e.g., valid oxygen saturation measurements are made), and the time since the last oximetry measurement has been made is greater than 2 seconds (e.g., time_now− last_StO2updatetime>2 seconds).

At 2705, the system unit reads the dipstate register to determine the inversion state (inverted or not inverted) of the system unit.

At 2710, if the system unit is not dipped (e.g., not inverted) and the clear flag for the dip state is 2 (the system unit has been changed from inverted to not inverted), then the clear flag is set to zero (normal operation for system unit) at 2715. If the system unit is not dipped (e.g., not inverted) and the clear flag for the dip state is 0 (normal operation state), then the system unit determines whether the clear flag is one at 2730.

At 2720, the system unit determines whether the system unit is dipped (e.g., inverted) and the clear flag is zero. If the system unit is dipped (e.g., inverted) and the clear flag is zero, then the clear flag is set to one (the system unit has been changed from not inverted to inverted) at 2725. If the system unit is dipped (e.g., inverted) and the clear flag is not zero, then the system unit determines whether the clear flag is one at 2730.

If the clear flag is one at 2730, then the average information for the tissue locations is reset. Specifically, the clear flag is set to two, the sum for the average for the tissue locations is set to zero, the average count for the tissue locations is set to zero, the average for the tissue location is set to zero, and the lift logic for the system unit is disarmed. That is, the system unit is not configured to determine whether the system unit has been lifted from patient tissue.

At 2740, the average displayed on the display of the system unit is cleared, and the method returns to the start state 2700 to generate a new oximetry measurement average. If the clear flag is not one at 2730, then the system unit makes an oximetry measurement (e.g., an oxygen saturation measurement) and determines whether oximetry information generated from the oximetry measurement is valid at 2745. The system unit may display the oximetry information on the display of the system unit if the oximetry information is valid. If the oximetry information is not valid, then at 2780 the system unit determines if the lift logic is armed. The lift logic is armed if the system unit displays the use message (e.g., "lift up) on the display and monitors for the sheath or system unit from being lifted from the tissue. Steps taken at 2780 and after are described further below.

At 2750, the system unit determines whether the lift logic is armed and increments the sample count for the tissue location by one.

At 2755, the system unit determines whether the valid sample count for tissue being measured is greater than or equal to 2. If the system unit determines that the valid sample count for tissue being measured is not greater than or equal to 2, then the system unit returns to the start at 2770.

If the system unit determines that the valid sample count for tissue being measured is greater than or equal to 2, then at 2760, the system unit determines whether the quality measurement (QM) of the oximetry measurements for the tissue being measured is greater than or equal to 1. The QM is greater than or equal to one, if the oximetry measurement information is valid. If the QM is not greater than or equal to one, then the system unit returns to the start at 2770. If the QM is greater than or equal to one, then at 2765, the sum for the number of measurements taken ("location sum") for the tissue being measured is set to the oximetry measurement for the tissue ("location sum=fSo2estimate"), the measurement count for the tissue being measured is incremented by one ("location count++"), and the oximetry measurement average for the tissue being measured is calculated ("location average=location sum/location count") where the location sum include the sum of the oximetry measurement information (e.g., oximetry measurement values) for the tissue location include the latest oximetry information (e.g., latest oximetry measurement value) for the latest tissue location.

At 2770, the system unit determines whether the measurement count for the tissue being measured is greater than or equal to 3. If the measurement count for the tissue being measured is not greater than or equal to 3, then at 2780, the system unit determines if the lift logic is armed. Steps taken at 2780 and after are described further below. If the measurement count for the tissue being measured is greater than or equal to 3, then at 2775, the system unit displays the use message (e.g., "lift up") on the display of the system unit. After the lift message is displayed, the system unit returns to the start state of the method at 2700.

At 2780, if the system unit determines that the lift logic is not armed, then the system unit returns to the start at 2770. if the system unit determines that the lift logic is not armed, then at 2785, the lift logic is disarmed. That is, the system unit does not attempt to determine whether the sheath or system unit has been lifted from the tissue being measured.

At 2790, the use message (e.g., "lift up) is removed from the display.

At 2795, the sample count is set to zero, and the location sum is set to zero.

At 2800, the system unit determines whether the area count (e.g., the number of tissue locations of a patient that are measured) is less than 9 and whether the location count (e.g., number of oximetry measurements made for a tissue location) is greater than or equal to 2. If the area count is not less than 9 and if the location count is not greater than or equal to 2, then the system unit stops generating an average value for the oximetry measurements, at 2805.

If the area count is less than 9 and if the location count is greater than or equal to 2, then the system unit calculates the sum of the oximetry measurements for each of the tissue locations (i.e., "area sum=area sum+location average"), at 2810. The area count is incremented by one, at 2810. And, the average oximetry measurement for the tissue location is calculated (i.e., "area average=area sum/area count"), at 2810.

At 2815, the system unit determines whether the area count (number of tissue locations of the patient for which oximetry measurements are made) is greater than to zero. If the area count is not greater than or equal to zero, then the system unit does not display the area average until three tissue locations have been measured (e.g., oximetry measurement made) by the system unit, at 2825 (FIG. 14). Instead of displaying the are average, the system unit may display text (e.g., two dashes, "--"), an icon, or both to indicate that the area average is not being displayed. If the area count is not greater than zero, then the system unit proceeds to 2820.

At 2820, the system unit determines whether the area count (number of tissue locations of the patient for which oximetry measurements are made) is greater than three. If the area count is not greater than three, then the system unit displays the area count on the display, and does not display the area average at 2825. That is, the system unit does not display the area average until three tissue locations have been measured (e.g., oximetry measurement made) by the system unit (FIG. 14). Instead of displaying the are average, the system unit may display text (e.g., two dashes, "--"), an icon, or both to indicate that the area average is not being displayed. If the area count is greater three, then at 2830, the system unit displays the area count on the display, and displays the area average (FIG. 15).

At 2840, the location count is set to zero and the location average is set to zero. The system unit then returns to the start of the method at 2700. That is, after a pass through the method the system unit may continue to make oximetry measurements for tissue locations of the patient tissue to generate an average of the tissue location for which valid oximetry measurements are made.

In an implementation, the system unit is adapted to perform a rolling average of oximetry measurement values (e.g., oxygen saturation values). The processor can use a stack to accumulate oximetry measurement values as the values are generated by the system unit. The values can be for the 1 to n−1 oximetry measurements for all placements and lift ups of the system unit from tissue. The system unit can track and save a number for all of the oximetry measurement values that are to be included in the average to then generate that average oximetry measurement value. When the stack overflows, the value that is falling off of the stack can be subtracted from a summed value of oximetry measurement values in the stack so that the average remains accurate. The number of oximetry measurement values in an average is limited by the stack.

In an implementation, the system unit is adapted to perform a rolling average of oximetry measurement values (e.g., oxygen saturation values). The processor can use a stack to accumulate oximetry measurement values as the values are generated by the system unit. The values can be for the n−1 oximetry measurements for all placements and lift ups of the system unit from tissue. The system unit can track and save a number for all of the oximetry measurement values that are to be included in the average to then generate that average oximetry measurement value. When the stack overflows, the value that is falling off of the stack can be subtracted from a summed value of oximetry measurement values in the stack so that the average remains accurate. The number of n−1 oximetry measurement values in an average is limited by the stack.

Figure 23:
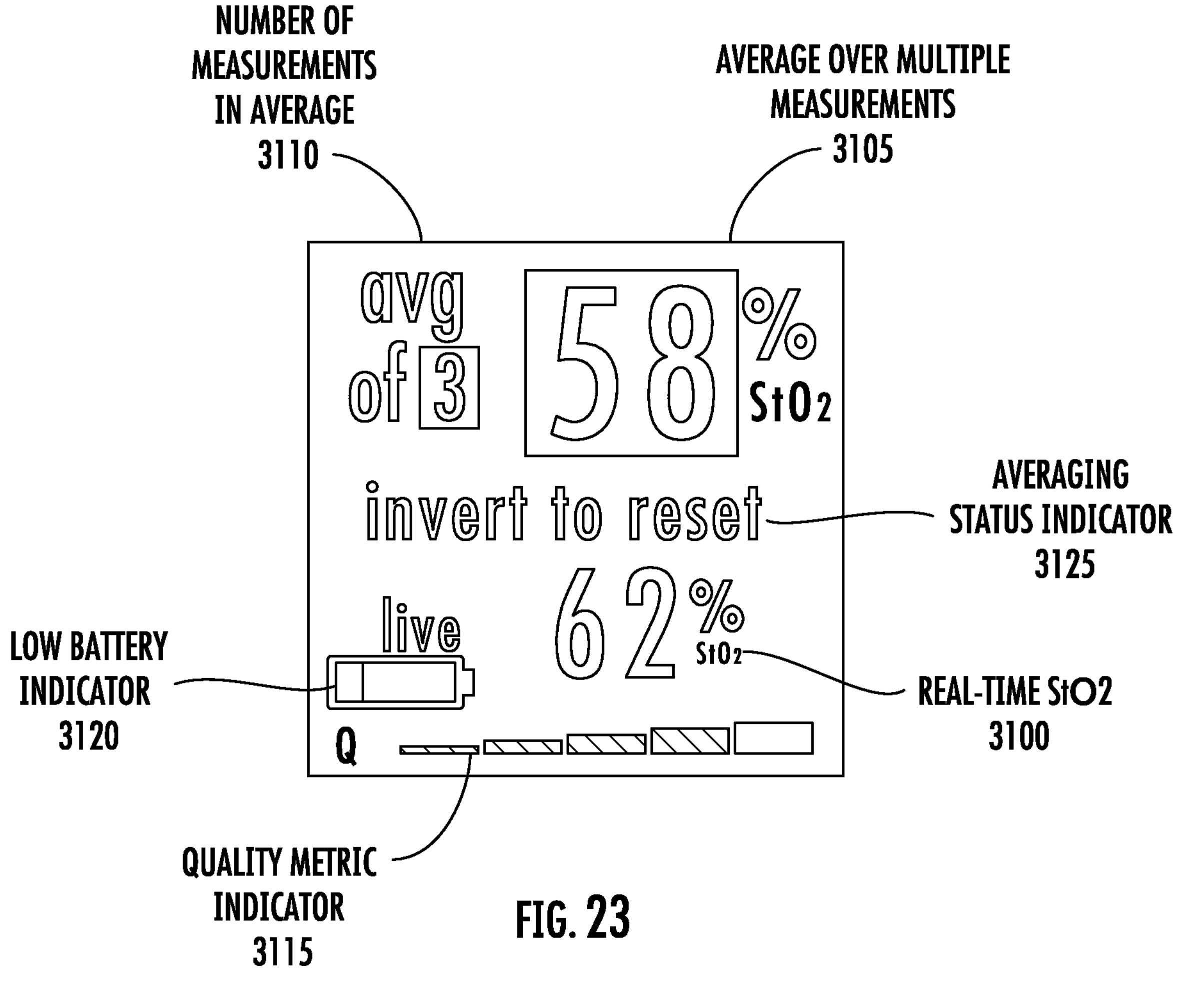
FIG. 23 shows the display of the system unit displaying a number of pieces of information generated by the system unit.

FIG. 23 shows the display of the system unit displaying a number of pieces of information generated by the system unit. In an implementation, the display displays a real-time oxygen saturation value 3100, which is labeled "Real-Time StO2" in FIG. 23. In the example display shown in FIG. 23, the real-time oxygen saturation value is 62 percent.

The display can display the average of a number of real-time oximetry reading values 3105, which is labeled "Average Over Multiple Measurements" in FIG. 23. In the example display shown in FIG. 23, the average is 58%. The display can display the number of real-time oximetry reading values 3010, which is labeled "Number of Measurements in Average" in FIG. 30, that are averaged to generate the average of the number of oximetry reading values. In the example display shown in FIG. 23, the number of real-time oximetry reading values in the average is 3.

In an implementation, the system unit makes oximetry readings when the system unit or the sheath, which the system unit is located in, makes good contact with tissue for at least three displayed readings (for example, about six seconds). In an implementation, an oximetry reading is the instantaneous oxygen saturation StO2 that is calculated by the system unit at any given time, based on the system unit sequencing through the lighting of the system unit's various LEDs (light emitting diodes), and measuring, by the unit's one or more detectors, intensities of the light after being transmitted through the illuminated tissue. An oximetry reading can further include the system unit performing various operations on the collected and measured light, such as performing one or more of digitization, various comparisons, calibration adjustments, calculations, memory storage operations, other operations, or any combination of these operations.

As described briefly above, oximetry readings are taken by the system unit's processor at a variable rate, between 0.5 hertz and 3.2 hertz, where the variability of the rate is dependent on the requirements of a thermal control measurement system and various thermal algorithms operated by the system unit. In other implementations, the rate can be above 3.2 hertz, such as from about 4 hertz to about 1 kilohertz. The system unit's ADC can sample measurement information generated by the system unit's photodetectors at a higher rate, such as about 200-300 kilohertz. In an implementation, a most recent oximetry reading value is displayed on the display. In an implementation, subsequent to an oximetry reading value being displayed on the display, the oximetry reading value is stored in one of the system unit's memory devices, such as the system unit's flash memory. Storage and use of oximetry reading values by the system unit are described further below.

Oximetry reading values are the labeled "real-time StO2" values that are displayed on the lower right portion of the display, as shown in FIG. 23. The location where the oximetry reading values are displayed on the display is sometimes referred to as the "live" field because every two seconds, for example, the system unit controls the display to display whatever the most recent oximetry reading value that the system unit has generated. Thus, a user of the system unit is able to view and ascertain the most recent tissue property of a patient.

In an implementation, the sheath with the system unit located inside the sheath can make one or more oximetry readings of tissue. In another implementation, the system unit is used without the sheath and can make one or more oximetry readings.

The following description describes the use of the system unit located in the sheath. The following description applies equally to the use of the system unit without the sheath. The system unit makes a "measurement" during a time period when a sensor window of the sheath is placed into contact with tissue by a user and is removed from contact with the tissue. The system unit can make a number of readings (e.g., five readings) when the sensor window of the sheath is placed into contact with tissue and then removed from contact with the tissue for the number of times (e.g., five series of contact and subsequent lift from contact events). When a current oximetry reading value is displayed on the display and the value is stored in memory, a time value for a time that oximetry reading is display on the display is stored in a memory of the system unit. When the oximetry reading value is displayed on the display for a time that is greater than a threshold time (e.g., about 1.5 seconds to about 3 seconds, such as about 2 seconds), a new oximetry reading value is displayed on the display. Prior to the new oximetry reading being displayed on the display for the threshold time, each most recent oximetry reading value is stored in memory. In a specific implementation, only the most recent oximetry reading value that is displayed on the display is stored in memory.

When the system unit is located in the sheath, the probe tip that includes one or more light source structures (i.e., source structures) and one or more light detector structures (i.e., detector structures) is in contact with a sensor window of the sheath. Through the sensor window, the system unit can emit light into tissue from the source structures and detect the light subsequent to the light traveling through the tissue. Light can include visible light (e.g., red light), infrared (e.g., near-infrared light), or both visible light and infrared (IR).

In an implementation, the system unit averages a number of oximetry reading values from a corresponding number of measurements. As described briefly above, the system unit stores an oximetry reading value from a measurement in the unit's memory, such as the unit's flash memory. Each stored oximetry reading value is the n−1 oximetry reading value of n oximetry reading values generated by the system unit. When a new oximetry reading value (n value) is displayed on the display, the subsequently displayed oximetry reading value (n−1) is stored in the memory. Each oximetry reading value that is stored in the memory is overwritten by a new n−1 oximetry reading value. Storing and overwriting is a continuous process for each measurement (e.g., a placement on tissue and a subsequent lift from the tissue after the placement) that the system unit makes.

Figure 24:
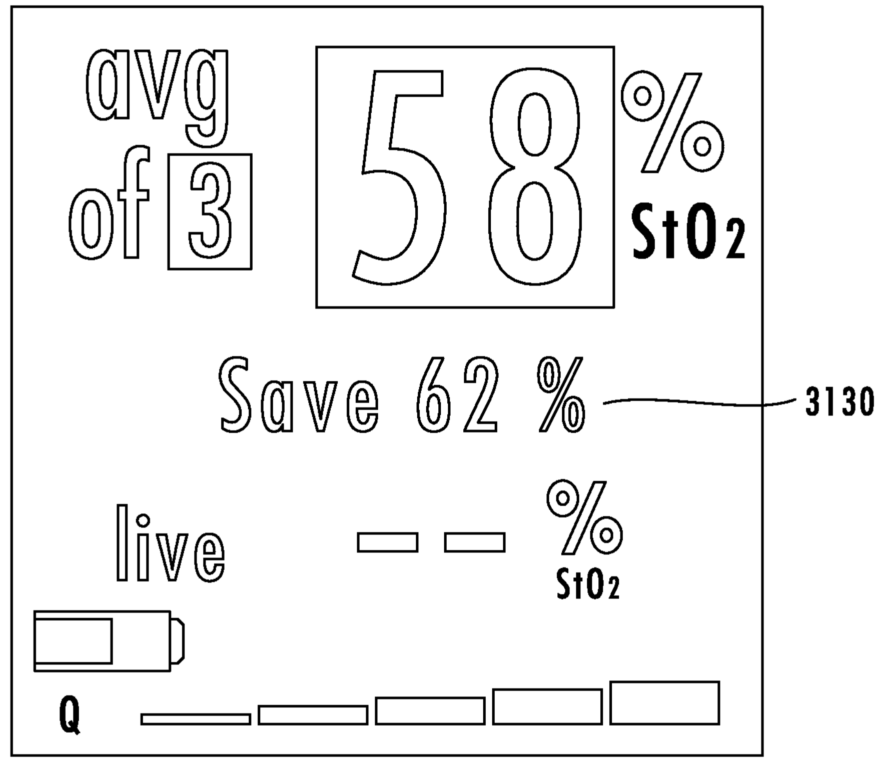
FIG. 24 shows the display with the "Saved NN %" message in the center field of the display of the system unit.

When a user removes the sheath from contact with tissue and a measurement is concluded, the system unit uses the oximetry reading value stored in memory for generating an average of oximetry reading values. Each nth oximetry reading value for a measurement is not stored in the memory and is not used for generating an average of oximetry reading values because there is a possibility that the sheath was in poor contact or out of contact with the tissue when the nth oximetry reading value was generated. Thus, each nth oximetry reading value may not be an accurate value of the oxygen saturation of the tissue. Thus, the n−1 (second to last) oximetry reading values of measurement are used by the system unit to generate an average. The system unit briefly displays the text "Saved NN %" 3130 in the center field of the display, indicating that a particular oximetry reading value has been saved to the memory and thus indicating that the value will be used by the system unit to generate the average. FIG. 24 shows the display with the "Saved NN %" message in the center field of the display. In the particular example implementation shown in FIG. 24, the saved value is Saved 62%.

The system unit increments and stores a value for the number of measurements that the system unit has taken. The number is used by the system unit to generate the average for the oximetry reading values for the measurements. In the particular example implementation shown in FIG. 24, the number of measurements is 3.

In an implementation, the system unit generates a sum for the n−1 oximetry reading values that are stored in memory when a measurement is concluded (i.e., when the sheath is removed from contact with patient tissue). This sum is stored in the memory. The average of the oximetry reading values is the sum divided by the number of measurements. The sum is sometimes referred to as a running sum and the average is sometimes referred to as a running average.

In an implementation, an average oximetry value is displayed on the display of the system unit. As shown in FIG. 23, the average oximetry value is displayed on the upper right side of the display. The average oximetry value may be displayed at other locations of the display. The number of oximetry reading values included in an average oximetry value is also displayed on the display, in an embodiment. As shown in FIG. 23, the number is displayed on the upper left side of the display. In an implementation, an oximetry reading value, an average oximetry value, and the number of measurements in an average are displayed on the display when no warnings are displayed on the display, no system unit error has occurred, or both.

Figure 25:
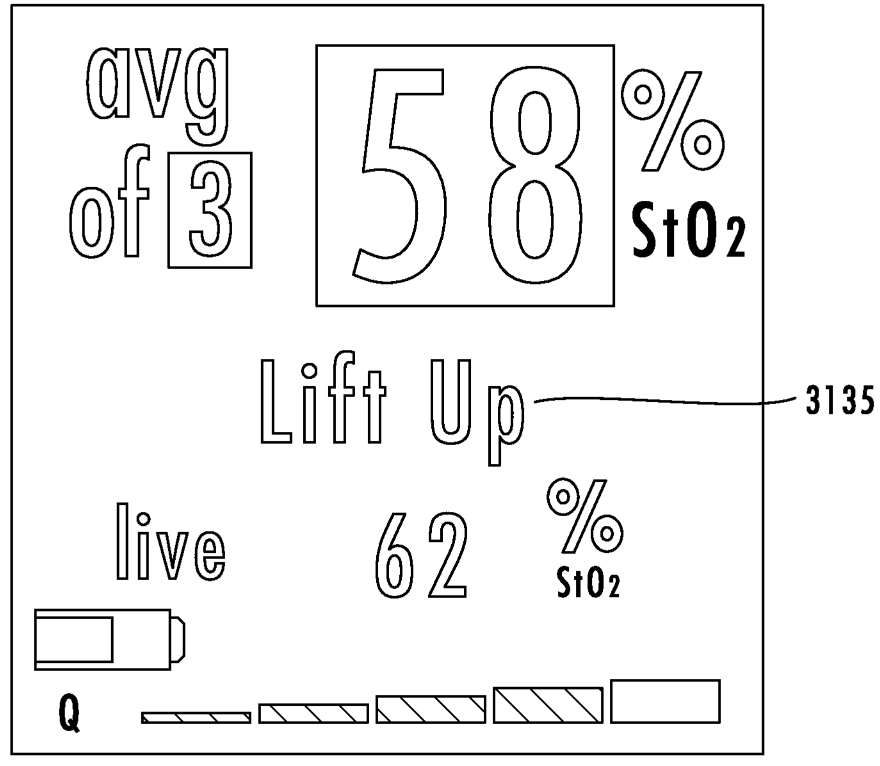
FIG. 25 shows the display with a "Lift Up" message displayed on the display of the system unit.

FIG. 25 shows the display with a "Lift Up" message 3140 displayed. In an implementation, after a number of oximetry reading values have been made and displayed on the display, typically after about 4 seconds to about 8 seconds (e.g., after about 6 seconds), the lift up message is displayed on the display. The displayed lift up message indicates that a measurement can be completed and a user can lift the sheath from contact with the tissue. The lift up message also indicates to a user that a current oximetry reading value will be stored in the memory so that the generation of an average oximetry value can occur. The lift up message may be located below the value for the number of measurements in an average, below the average oximetry value identified by the label number of measurements in average, and above the real-time StO2 value.

Figure 26:
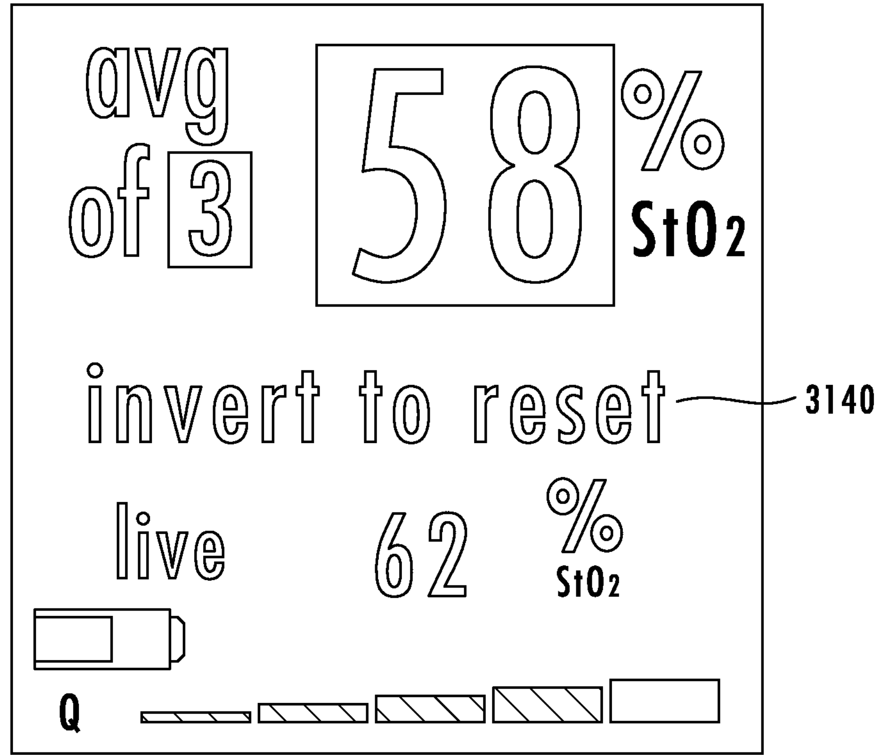
FIGS. 26-27 show the display with an "invert to reset" message displayed on the display of the system unit.
Figure 27:
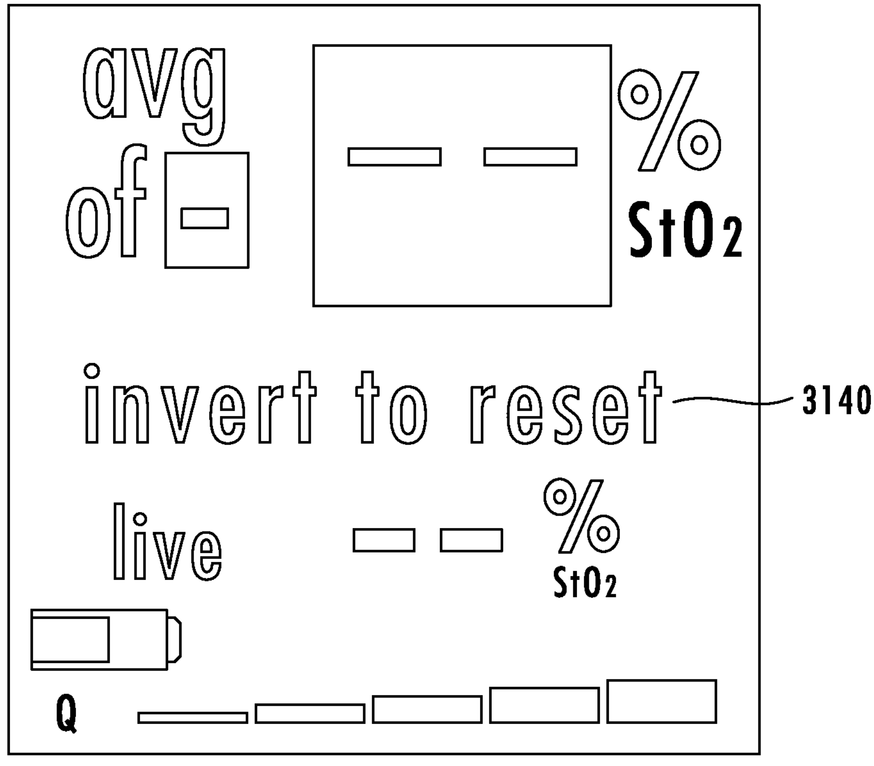
Figure 28:
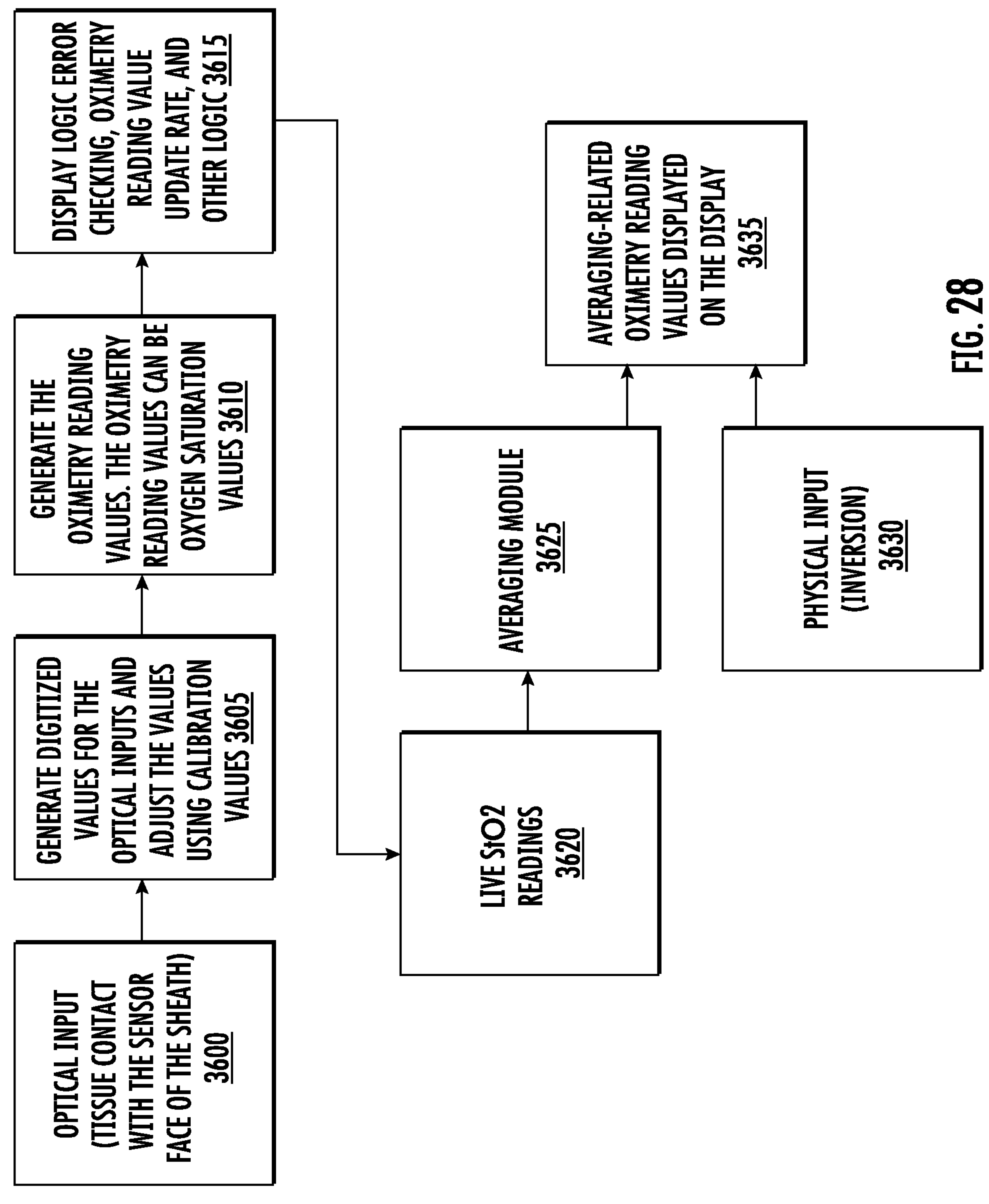
FIG. 28 is a flow diagram for a flow of information and a processing flow performed by the system unit.

FIGS. 26-27 show the display with an "invert to reset" message 3140 displayed on the display. When the system unit is making measurements and the "lift up" message is not displayed and the "Saved NN %" message is not displayed, the invert to reset message is displayed on the display. The invert to reset message informs a user that the system unit can be inverted to reset values stored in memory in the system unit. The live oximetry reading value, the average of the oximetry reading values, and the value for the number of measurements in the average may be reset when the system unit is inverted. FIG. 26 shows the display prior to the system unit being inverted with the live oximetry reading value, the average of the oximetry reading values, and the value for the number of measurements in the average displayed on the display. FIG. 27 shows the display subsequent to the system unit being inverted with each of the live oximetry reading values, the average of the oximetry reading values, and the value for the number of measurements in the average replaced with dashes displayed on the display. The dashes indicate that the values have been reset from the inversion. Other graphical images or marks may be displayed to indicate that the values have been reset.

For example, the average value for the current reading value is reset, the number of current reading values included in the average is reset, and the oximetry reading values stored in the flash memory are reset. The system unit is in an inverted state when the display is down and the probe tip is up. The values stored in the system unit may be reset by other methods, such as the system unit being subjected to one or more impulse forces, a button press of a button on the system unit, or other methods.

After the system unit is reset, no oximetry reading value is displayed in the live field. A graphic image or various characters (e.g., "- -") may be displayed to indicate that no oximetry reading value is available for display. Further, a graphic image or various characters (e.g., "- -") may be displayed to indicate that no average of the oximetry reading values is available for display.

The messages displayed in the center field of the display are sometimes referred to as "use messages." The use message indicates an action that a user can perform for operating the system unit and can inform a user of an operation that the system unit is performing. For example, the use messages inform a user that the system unit may be inverted to reset data or lift up to end a measurement. The use message can inform a user of an action that the system unit is performing, such as saving a live oximetry reading value.

In an implementation, the background of the display is displayed in a first color, such as black. The oximetry measurement reading value is displayed in a second color, such as an inverted color that is inverted with respect to the first color. The second color may be white. Text in the central field is also displayed in the second color. The oximetry reading value and the symbols and text identifying the oximetry reading value (e.g., "% StO2" and "live") can be displayed in the second color (e.g., white).

The value for the measurement average of the oximetry reading values is displayed in a color inverted background. The color inverted background can be white (i.e., the first color). The color inverted background may have a variety of shapes, such as square, rectangular, or another shape. The measurement average value displayed in the inverted background can be the first color (e.g., black). Symbols and text identifying the measurement average value (e.g., "% StO2") are displayed in the second color (e.g., white)

The value for the number of measurements in that measurement average of the oximetry reading values is displayed in a color inverted background. The color inverted background can be white (i.e., the first color). The color inverted background may have a variety of shapes, such as square, rectangular, or another shape. The number of measurement averages displayed in the inverted background can be the first color (e.g., black). Symbols and text identifying the number of measurements (e.g., "avg of") are displayed in the second color (e.g., white).

The quality metric scale 3115, which is labeled "Measurement Quality Indicator" in FIG. 22A can be displayed in the second color. The battery indicator 3120, which is labeled "Low Battery Indicator" in FIG. 22A, can be displayed in a combination of the first and second colors.

Table C below shows an example series of events of operation of the system unit. The example series of events includes generating and displaying oximetry reading values, generating and displaying averages of oximetry reading values, generating and displaying a number of oximetry reading values in the averages, and displaying various messages on the display. As a general overview of table C, a user uses the system unit to make two measurements. Each measurement includes a number of oximetry readings in which a number of oximetry reading values are generated.

At line item 1 in table C, a user, such as a surgeon, holds the system unit in the air in preparation to contact the sheath window of the sheath to patient tissue. The system unit displays two dashes or other information that indicates no oximetry reading values are available for display in the live StO2 field of the display. The system unit displays two dashes or other information that indicates that no average of the oximetry reading values is available for display in the average StO2 field of the display. The number of oximetry reading values is zero, and zero may be displayed in the field for the number of measurements in the average. The system unit displays the message "Invert to Reset" on the display in an "Averaging Status Indicator" field 3125, indicating to a user that the system unit can be inverted to reset the stored oximetry information in the unit. The state of the system unit at line item 1 is the state of the unit after being inverted.

At line item 2 in table C, the sheath (e.g., sheath window 218) is placed into contact with patient tissue. The system unit makes a tissue measurement and generates an oximetry reading value labeled value A that is displayed on the display in the live field. The system unit displays two dashes or other information that indicates that no average of the oximetry reading values is available for display in the average StO2 field of the display. The number of oximetry reading values is zero, and zero may be displayed in the field for the number of measurements in average. The system unit displays the message "Invert to Reset" on the display, indicating to a user that the system unit can be inverted to reset the stored oximetry information in the unit.

At line item 3 in table C, after the sheath (e.g., sheath window 218) has been in contact with the tissue for about 5 to about 6 seconds, the system unit makes a tissue measurement and generates an oximetry reading value labeled value B that is displayed on the display in the live field. The sheath has been in contact with tissue for a sufficient time (e.g., about 5 seconds to about 6 seconds) such that the logic used by the system unit for generating an average of the oximeter oximetry reading value is initiated. The system unit displays two dashes or other information that indicates that no average of the oximetry reading values is available for display in the average StO2 field of the display. The number of oximetry reading values is zero, and zero may be displayed in the field for the number of measurements in an average. The system unit displays the message "Lift Up" on the display, indicating to a user that the system unit can be lifted so that a measurement can be completed and a value is available to enter into the memory for generating an average of the oximeter reading values.

At line item 4 in table C, the user continues to hold the sheath in contact with the tissue where the system unit makes n tissue measurement and generates an oximetry reading value labeled value N that is displayed on the display in the live field. The system unit displays two dashes or other information that indicates that no average of the oximetry reading values is available for display in the average StO2 field of the display. The number of oximetry reading values is zero, and zero may be displayed in the field for the number of measurements in an average. The system unit continues to display the message "Lift Up" on the display indicating to a user that the system unit can be lifted so that a measurement can be completed and a value is available to enter into the memory for generating an average of the oximeter reading values.

At line item 5 in table C, the user removes the sheath from being in contact with the tissue and the system unit detects the sheath being out of contact. The system unit displays two dashes or other information that indicates that no average of the oximetry reading values is available for display in the average StO2 field of the display. The system unit displays the oximetry reading value n−1 in the average StO2 field of the display. The number of oximetry reading values is 1, and 1 may be displayed in the field for the number of measurements in an average. The system unit displays the saved oximetry reading value n−1 on the display.

At line item 6 in table C, the user holds the sheath in the air in preparation to contact the sheath to patient tissue. The system unit displays two dashes that indicate no oximetry reading values are available for display in the live StO2 field of the display. The system unit displays the oximetry reading value n−1 in the average StO2 field of the display. The number of oximetry reading values is 1, and 1 may be displayed in the field for the number of measurements in the average. The system unit displays the message "Invert to Reset" on the display, indicating to a user that the system unit can be inverted to reset the stored oximetry information in the unit.

At line item 7 in table C, the sheath is placed into contact with patient tissue. The system unit makes a tissue measurement and generates an oximetry reading value labeled value C that is displayed on the display in the live field. The system unit displays the oximetry reading value n−1 in the average StO2 field of the display. The number of oximetry reading values is 1, and 1 may be displayed in the field for the number of measurements in average. The system unit displays the message "Invert to Reset" on the display, indicating to a user that the system unit can be inverted to reset the stored oximetry information in the unit.

At line item 8 in table C, the user removes the sheath from being in contact with the tissue and the system unit detects the sheath being out of contact. The user lifts the sheath from being in contact with the tissue before the sheath is in contact with the tissue for about 5 seconds. Because the Lift Up message was not displayed on the display a new oximetry reading value will not be used to generate a new average of the oximetry reading values. The system unit continues to display the oximetry reading value n−1 in the average StO2 field of the display. The number of oximetry reading values is 1, and 1 may be displayed in the field for the number of measurements in the average. The system unit displays the message "Invert to Reset" on the display, indicating to a user that the system unit can be inverted to reset the stored oximetry information in the unit.

At line item 9 in table C, the user holds the sheath in the air in preparation to contact the sheath to patient tissue. The system unit displays two dashes that indicate no oximetry reading values are available for display in the live StO2 field of the display. The system unit displays the oximetry reading value n−1 in the average StO2 field of the display. The number of oximetry reading values is 1, and 1 may be displayed in the field for the number of measurements in an average. The system unit displays the message "Invert to Reset" on the display, indicating to a user that the system unit can be inverted to reset the stored oximetry information in the unit.

At line item 10 in table C, the sheath is placed into contact with patient tissue. The system unit makes a tissue measurement and generates an oximetry reading value labeled value D that is displayed on the display in the live field. The system unit displays the oximetry reading value n−1 in the average StO2 field of the display. The number of oximetry reading values is 1, and 1 may be displayed in the field for the number of measurements in average. The system unit displays the message "Invert to Reset" on the display, indicating to a user that the system unit can be inverted to reset the stored oximetry information in the unit.

At line item 11 in table C, after the sheath has been in contact with the tissue for about 5 to about 6 seconds, the system unit makes a tissue measurement and generates an oximetry reading value labeled value M that is displayed on the display in the live field. The sheath has been in contact with tissue for a sufficient time (e.g., about 5 seconds to about 6 seconds) such that the logic used by the system unit for generating an average of the oximeter oximetry reading value is initiated. The system unit displays two dashes or other information that indicates that no averages of the oximetry reading values are available for display in the average StO2 field of the display. The number of oximetry reading values is zero, and zero may be displayed in the field for the number of measurements in the average. The system unit displays the message "Lift Up" on the display, indicating to a user that the system unit can be lifted so that a measurement can be completed and a value is available to enter into the memory for generating an average of the oximeter reading values.

At line item 12 in table C, the user removes the sheath from being in contact with the tissue and the system unit detects the sheath being out of contact. The system unit displays two dashes or other information that indicates that no average of the oximetry reading values is available for display in the average StO2 field of the display. The system unit displays the average of the oximetry reading value n−1 and m−1 in the average StO2 field of the display. The number of oximetry reading values is 2, and 2 may be displayed in the field for the number of measurements in the average. The system unit displays the saved oximetry reading value m−1 on the display.

At line item 13 in table C, the user removes the sheath from being in contact with the tissue and inverts the system unit and the system unit resets. The system unit is in an inverted state when the display is down and the probe tip is up. The system unit includes an accelerometer that can detect the system unit being inverted. During the reset, the average value for the current reading value is reset, the number for the number of current reading values included in the average is reset, and the oximetry reading values stored in the flash memory are reset. A message indicating that the system unit is being reset is displayed on the display.

At line item 14 in table C, the user holds the sheath in the air in preparation to contact the sheath to patient tissue. The system unit displays two dashes or other information that indicates no oximetry reading values are available for display in the live StO2 field of the display. The system unit displays two dashes or other information that indicates that no average of the oximetry reading values is available for display in the average StO2 field of the display. The number of oximetry reading values is zero, and zero may be displayed in the field for the number of measurements in the average. The system unit displays the message “Invert to Reset” on the display, indicating to a user that the system unit can be inverted to reset the stored oximetry information in the unit. The state of the system unit at line item 1 is the state of the unit after being inverted.

TABLE C

| Line item | User Action | Live StO2 | Average StO2 | Number of Values in Average | Text | Notes |
|---|---|---|---|---|---|---|
| 1 | Surgeon holding system unit in the air | — | — | 0 | Invert to Reset | State after initial system unit inversion |
| 2 | Surgeon places system unit in contact with tissue | valueA | — | 0 | Invert to Reset | Since the contact is valid with tissue, a reading gets displayed on the display |
| 3 | After five seconds of contact with tissue | valueB | — | 0 | LIFT UP | Since the system unit was in contact with tissue for a while, the logic for averaging is triggered |
| 4 | Surgeon continues holding | valueN | — | 0 | LIFT UP | This state persists until the surgeon ends their measurement |
| 5 | Surgeon lifts up | — | valueN-1 | 1 | Saved Value N-1% | Live reading no longer valid, so reverts to - - |
| 6 | Surgeon holding system unit in the air | — | valueN-1 | 1 | Invert to Reset | The ‘averaging fields’ persist |
| 7 | Surgeon places system unit in contact with tissue | valueC | valueN-1 | 1 | Invert to Reset | Same as line item 2, excepts we now have averages |
| 8 | Surgeon lifts up before 5 seconds of contact | — | valueN-1 | 1 | Invert to Reset | Nothing saved into average if the LIFT UP message was not displayed on the display |
| 9 | Surgeon lifts up before 5 seconds of contact | — | valueN-1 | 1 | Invert to Reset | Same system unit state as line item 6 |

TABLE C-continued

| Line item | User Action | Live StO2 | Average StO2 | Number of Values in Average | Text | Notes |
|---|---|---|---|---|---|---|
| 10 | Surgeon places system unit in contact with tissue | valueD | valueN-1 | 1 | Invert to Reset | Same as line item 7 |
| 11 | After five seconds of contact with tissue | valueM | valueN-1 | 1 | LIFT UP | Surgeon can lift immediately at the 'LIFT UP' message |
| 12 | Surgeon lifts up | — | avg([vN-1 vM-1]) | 2 | Saved Value M-1% | First' real' averaging behavior. The values from line items 5 and 12 are averaged together |
| 13 | Surgeon inverts system unit | Display shows a confirmation message | Display shows a confirmation message | Display shows a confirmation message | Display shows a confirmation message | Everything gets reset back to default |
| 14 | Surgeon holding system unit in the air | — | — | 0 | Invert to Reset | Same as line item 1 |

The display can display additional information, such as a quality metric indicator. The quality metric indicator is labeled "Measurement Quality Indicator" in FIG. 22A. In the implementation shown in FIG. 22A, the quality metric indicator can highlight 5 bars. The bars can be highlighted or not highlighted to include the quality of contact of the sheath with the tissue. The display can also display a battery charge indicator. The battery charge indicator can be displayed on the display below the center field as shown in FIGS. 24-25 or can be displayed in other locations on the display.

FIG. 27 is a flow diagram for a flow of information and a processing flow performed by the system unit. The steps of the diagram can be implemented in circuits in the system unit, software modules that include software than can be executed by various circuits of the system unit, user operation of the system unit, or any combination of circuits, software, and user operation.

In an implementation, at 3600 a sensor window of the sheath with the system unit located in the sheath is placed into contact with tissue to be measured. The source structures of the system unit can direct light (e.g., visible, near infrared, or both) into the tissue through the sensor window. After the light is transmitted through the tissue, the detectors structures of the system unit can detect the tissue. At 3605, the system unit digitizes light information generated by the detectors in response to the detected light. The digitized values can be adjusted using one or more calibration coefficients stored in the memory of the system unit. At 3610, the system unit generates oximetry reading values from the digitized information. The other intermediate values in a calculation can also be generated, such as absorption coefficient, reduced absorption coefficients, or other values. At 3615, the system unit performs error checking, an oximetry reading value update rate, other logic, one of these processes, or any combination of these processes. At 3620, the system unit generates values for the live oximetry reading values. At 3635, the system unit generates the values for the measurement averages. The oximetry reading values, the measurement averages, and the number of measurements in an average are provided to the display for display at 3635. At 3630, the system unit generates information from physical input from various modules of the system unit, such as the accelerometer. The accelerometer can provide information for inversion of the system unit for resetting information for the oximetry readings, the measurement averages, and the number of measurements in an average. The physical input information is provided to the display at 3635 for control of the display to display reset information or other physical information. The steps of the method are described further below with respect to circuit elements of the system unit that may perform the described functions.

Table D shown below includes code that facilitates the operation of the system unit as described.

TABLE D

```
// There is a way to "turn off" the display by setting the display mode to ALL_OFF,
// which sets all the pixels to black. If this feature is used and you want to
//"turn on" the display again, you need to set the display mode to NORMAL again.
// To achieve this, #define FORCE_NORMAL_DISLAY_MODE
//---------------------------------------------------------------------------
/// @name oled_selectDevice
```

TABLE D-continued

```
///
/// @brief Asserts low/high on the OLED chip select pin
///
/// @param _1Bool bSelect -- _TRUE to select the device and commence
/// SPI transactions, _FALSE otherwise
///
/// @return void
///
/// @note This function is registered as a bsp_devIoctl function when
/// oled_useBus is called.
//------------------------------------------------------------------------------
//------------------------------------------------------------------------------
/// @name oled_selectFunction
///
/// @brief Asserts low/high on the OLED DC pin to specify data/command operations
///
/// @param UInt8 uDCValue -- the logical value to assert on the DC pin
///
/// @return void
///
/// @note
///
//------------------------------------------------------------------------------
//------------------------------------------------------------------------------
/// @name nfc_open
///
/// @brief Assigns the SPI device handle
///
/// @param void
///
/// @return _LResult -- Error code
///
/// @note
//------------------------------------------------------------------------------
//------------------------------------------------------------------------------
/// @name oled_useBus
///
/// @brief Configures and locks the SPI bus
///
/// @param void
///
/// @return _LResult -- error code
///
/// @note
//------------------------------------------------------------------------------
//------------------------------------------------------------------------------
/// @name oled_disuseBus
///
/// @brief Deconfigures and unlocks the SPI bus to release OLED use
///
/// @param void
///
/// @return _LResult -- error code
///
/// @note
//------------------------------------------------------------------------------
//------------------------------------------------------------------------------
/// @name oled_writeCommand
///
/// @brief Writes command codes (see MP_SSD1351_Defs.h) to the OLED controller
///
/// @param UInt8 uCommand -- command code that will be written to the
/// command register
///
/// @return _LResult -- error code
///
/// @note This function does NOT handle SPI bus locking/unlocking
//------------------------------------------------------------------------------
//------------------------------------------------------------------------------
/// @name oled_singleWriteData
///
/// @brief Writes a single data byte to the OLED controller
///
/// @param UInt8 uData -- byte that will be written to the GRAM
///
/// @return_LResult -- error code
///
/// @note This function does NOT handle SPI bus locking/unlocking
//------------------------------------------------------------------------------
//------------------------------------------------------------------------------
```

TABLE D-continued

```
/// @name oled_batchWriteData
///
/// @brief Writes multiple data bytes to the OLED controller
///
/// @param UInt8 *puData -- pointer for the data buffer that will be
/// written to the GRAM
///
/// @param UNativeInt nBytesToWrite -- number of bytes to be written
///
/// @return _LResult -- error code
///
/// @note Writes via DMA for blocks larger than SSI_FIFO_DEPTH.
/// This function does NOT handle SPI bus locking/unlocking.
//-----------------------------------------------------------------------------
//-----------------------------------------------------------------------------
/// @name oled_setDrawArea
///
/// @brief Specifies the start/end addresses of the display data RAM
///
/// @param int xStart, yStart -- start column and row addresses,
/// respectively
///
/// @param int xEnd, yEnd -- end column and row addresses, respectively
///
/// @return _LResult -- error code
///
/// @note This also prepares the controller to write color data to RAM
//-----------------------------------------------------------------------------
///// EXTERNAL FUNCTIONS ////////////////////////////////////////////////////////
//-----------------------------------------------------------------------------
/// @name OLED_powerOnOff
///
/// @brief Enables/disables power to display
///
/// @param _lBool bOn -- _TRUE to enable power, _FALSE otherwise
///
/// @return void
///
/// @note
//-----------------------------------------------------------------------------
//-----------------------------------------------------------------------------
/// @name OLED_sleepOnOff
///
/// @brief Enters/exits sleep mode
///
/// @param _lBool bOn -- _TRUE to enter sleep mode, _FALSE otherwise
///
/// @return void
///
/// @note
//-----------------------------------------------------------------------------
//-----------------------------------------------------------------------------
/// @name OLED_pulseReset
///
/// @brief Resets the display
///
/// @param void
///
/// @return void
///
/// @note
//-----------------------------------------------------------------------------
//-----------------------------------------------------------------------------
/// @name OLED_initialize
///
/// @brief Initial configuration sequence for the display
///
/// @param void
///
/// @return _LResult -- error code
///
/// @note This function handles SPI bus locking/unlocking
//-----------------------------------------------------------------------------
//-----------------------------------------------------------------------------//
// OLED_drawArea( ) expects a contiguous color array that exactly corresponds
// with the the draw area, i.e. it assumes that there is no padding before,
// after, or between rows and columns of pixels.
//
// This poses a problem for selections because if we have a 128 × 128 array
// where only part of it is occupied with color data, OLED_drawArea will
```

TABLE D-continued

```
// not render it correctly, even with the selection area as a parameter.
//
// OLED_drawSelection offers a workaround by doing a row-by-row draw
// of the selection.
//---------------------------------------------------------------------------
//-----------------------------------------------------------------------------
/// @name OLED_drawArea
///
/// @brief Draws part of a screen
///
/// @param OLED_DRAW_AREA *pDrawArea -- pointer to the struct indicating the
/// bounds of the draw area
///
/// @param UInt16 colorData[ ] -- pixel data (RGB565 color codes) of the draw area
///
/// @return _LResult -- error code
///
/// @note
//---------------------------------------------------------------------------
//---------------------------------------------------------------------------
/// @name OLED_singleColorFill
///
/// @brief Fills the specified draw area with a single color
///
/// @param OLED_DRAW_AREA *pDrawArea -- pointer to the struct containing the
/// start/end row/col
///
/// @param UInt16 fillColor -- RGB565 color code
///
/// @return _LResult -- error code
///
/// @note This function is non-reentrant, since it uses a static buffer. The
/// OLED device must be locked before calling this function.
//---------------------------------------------------------------------------
//---------------------------------------------------------------------------
/// @name OLED_cleanDrawFullScreen
///
/// @brief Draws a full screen by redrawing each pixel.
///
/// @param const UInt16 colorData[ ] -- pixel data (RGB565 color codes)
///
/// @return _LResult -- error code
//---------------------------------------------------------------------------
//---------------------------------------------------------------------------
/// @name OLED_clearScreen
///
/// @brief Clears the screen by turning off the display
///
/// @param --
///
/// @return _LResult
///
/// @note Previously displayed screen will appear again once display
/// is turned back on.
//---------------------------------------------------------------------------
//---------------------------------------------------------------------------
/// @name OLED_getDeviceId
///
/// @brief Returns the value of s_hSPI
///
/// @param void
///
/// @return BSP_HDEVICE -- value of s_hSPI
///
/// @note
//---------------------------------------------------------------------------
//---------------------------------------------------------------------------
/// @name OLED_setRotation
///
/// @brief Returns the value of s_hSPI
///
/// @param void
///
/// @return BSP_HDEVICE -- value of s_hSPI
//---------------------------------------------------------------------------
//---------------------------------------------------------------------------
/// @name OLED_drawSelection
///
/// @brief Draws in the area inside a selection
///
```

TABLE D-continued

```
/// @param const OLED_DRAW_AREA *pSelArea -- pointer to the struct
/// indicating the bounds of the selection area
///
/// @param const OLED_DRAW_AREA *pFullArea -- pointer to the struct indicating
/// the bounds of the overall bitmap (i.e. the selection is a subset of the overall bitmap)
///
/// @param const UInt16 fullAreaData[ ] -- overall bitmap color data
///
/// @return _LResult -- result code
//
// +-----------------+
// | |<--- pFullArea
// | +---------+ |
// | |//////////////|<------- pSelArea
// | |//////////////| |
// | +---------+ | //// = pixels to draw
// | |
// +-----------------+
//---------------------------------------------------------------------------
//---------------------------------------------------------------------------
/// @name OLED_drawInverseSelection
///
/// @brief Draws in the area outside a selection
///
/// @param const OLED_DRAW_AREA *pSelArea -- pointer to the struct
/// indicating the bounds of the selection area
///
/// @param const OLED_DRAW_AREA *pFullArea -- pointer to the struct indicating
/// the bounds of the overall bitmap (i.e. the selection is a subset of the overall bitmap)
///
/// @param const UInt16 fullAreaData[ ] -- overall bitmap color data
///
/// @return _LResult -- result code
//
// +-----------------+
// |///////////////////////|<--- pFullArea
// |////+---------+///|
// |////| |<------- pSelArea
// |////| |///|
// |////+---------+///| //// = pixels to draw
// |///////////////////////|
// +-----------------+
// Draw the top
// +-----------------+
// |///////////////////////|
// | +---------+ |
// | | | |
// | | | |
// | +---------+ |
// | |
// +-----------------+
// Draw the left side
// +-----------------+
// | |
// |///+---------+ |
// |///| | |
// |///| | |
// |///+---------+ |
// | |
// +-----------------+
// Draw the right side
// +-----------------+
// | |
// | +---------+////|
// | | |////|
// | | |////|
// | +---------+////|
// | |
// +-----------------+
// Draw the bottom
// +-----------------+
// | |
// | +---------+ |
// | | | |
// | | | |
// | +---------+ |
// |///////////////////////|
// +-----------------+
//---------------------------------------------------------------------------
/// @name OLED_fillSelection
```

TABLE D-continued

```
///
/// @brief Fills a selection with a single color
///
/// @param const OLED_DRAW_AREA *pSelArea -- pointer to the struct
/// indicating the bounds of the selection area
///
/// @param const OLED_DRAW_AREA *pFullArea -- pointer to the struct indicating
/// the bounds of the overall bitmap (i.e. the selection is a subset of the overall bitmap)
///
/// @param UInt16 fillColor - RGB565 encoding of the fill color
///
/// @return _LResult -- result code
//-----------------------------------------------------------------------------
//-----------------------------------------------------------------------------
/// @name OLED_fillInverseSelection
///
/// @brief Fills the area outside a selection with a single color
///
/// @param const OLED_DRAW_AREA *pSelArea -- pointer to the struct
/// indicating the bounds of the selection area
///
/// @param const OLED_DRAW_AREA *pFullArea -- pointer to the struct indicating
/// the bounds of the overall bitmap (i.e. the selection is a subset of the overall bitmap)
///
/// @param UInt16 fillColor - RGB565 encoding of the fill color
///
/// @return _LResult -- result code
//-----------------------------------------------------------------------------
```

In an implementation, the display is a pixilated display, having pixels arranged in rows and columns. The display can be an OLED (organic LED) display or a PLED (polymer OLED) display. In another implementation, the display is an LCD (liquid crystal display including for example, passive matrix LCD, active matrix LCD, IPS LCD, TN LCD, AFFS LCD, backlit LCD, and others) or an LED (light emitting diode display). The display can have a number of heights and widths. In an implementation, the display area of the display is square and is about 38 millimeters (1.5 inches) high by about 38 millimeters (1.5 inches) wide. The display can have a number of different pixels in each row and each column. In an implementation, the display is a square arranged with the same number of pixels horizontally and vertically, such as 128 pixels by 128 pixels. The display can be a color display or a monochrome (e.g., black and white, blue and white, or other single color and white) display. In a specific implementation, the display is a 4DOLED-282815 display manufactured by 4D System of Minchinbury Australia.

Table E below provides information for the locations of information displayed on the display. The location information includes a number of pixels that a piece of information is displayed at relative to the left side of the display and is referred to in table E as the left pixel offset. The location information includes a number of pixels that a piece of information is displayed relative to the top side of the display and is referred to in table E as the top pixel offset. The location information includes a pixel width value and pixel height value that indicate an area in pixels in which particular information is displayed. Table E is one particular implementation for information display on the display. Other implementations include the information displayed on the display located at alternative locations. It will be understood by those of skill in the art that displaying the displayed information a relatively small number (e.g., up to 1 to 10 pixels) of pixels from those pixels in table E are not a variation from the particular embodiment shown in this table.

TABLE E

| | Left Pixel Offset | Top Pixel Offset | Pixel Width | Pixel Height |
|---|---|---|---|---|
| Real-Time St02 | 56 | 79 | 32 | 30 |
| Average Number of Measurements in an Average | 29 | 27 | 10 | 16 |
| Average Over Multiple Measurements | 53.5 (e.g., 52 or 53 or 54) | 7 | 48 | 37 |
| Quality Metric Indicator | 0 | 113 | 128 | 15 |
| Battery | 18 | 104 | 28 | 9 |
| Center Field | 0 | 52 | 128 | 16 |

Figure 29:
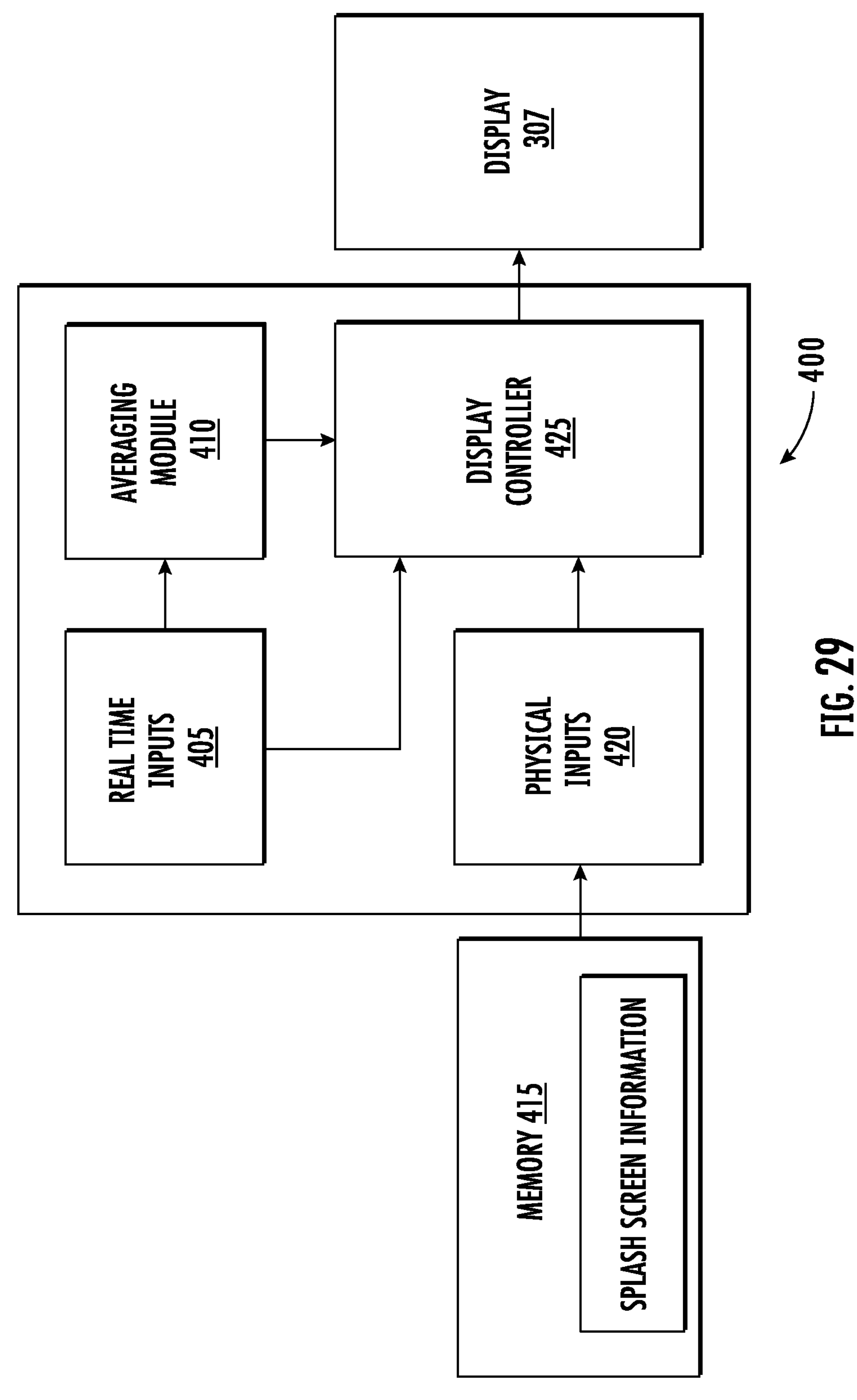
FIG. 29 shows a display system of an oximeter or other medical device that provides real-time and average values on a display.

FIG. 29 shows a display system of an oximeter or other medical device that provides real-time and average values on a display. The oximeter or other medical device can be a self-contained or standalone unit that is battery-operated and wireless or cordless (e.g., no power cord).

More specifically, a circuit 400 controls the display of information that is displayed on the display. The circuit includes a real-time input circuit 405, an averaging circuit 410, a physical input circuit 420, and a display controller circuit 425. FIG. 29 also shows display 307 and a memory 415 (e.g., a flash memory) connected to circuit 400.

In an implementation, real-time inputs circuit 305 is connected to the detectors of the system unit. The real-time inputs circuit can be a digital circuit that can receive digitized information for light that is collected by the detectors. An analog-to-digital converter circuit can be connected between the detectors and the real-time inputs circuit. In an implementation, the real-time inputs circuit can be a mixed signal device that includes an analog-to-digital converter circuit and additional circuits that can perform one or more of a variety of functions on light information received from the detectors. The real-time inputs circuit can include the processor of the system unit. The real-time inputs circuit can include additional circuits such as one or more buffer memories, timing circuits, control circuits, logic circuits, other circuits, or any combination of these circuits.

The real-time inputs circuit is coupled to both the averaging circuit 410 and the display controller 425. The real-time input circuit 410 can buffer oximetry reading values and transmit these values to the averaging circuit 410 and to the display controller circuit 425. The averaging module can receive the information from the real-time inputs circuit to determine a value for a measurement average from the information received from the real-time inputs circuit, one or more other circuits, or a combination of these circuits. For example, in an embodiment where the system unit includes an accelerometer, the averaging module can collect information directly or indirectly from the accelerometer to determine a number of measurements that the system unit has made for use in determining the average. In another embodiment, the averaging circuit module may be adapted to determine the beginning and end of a measurement based on the oximetry measurement values received from the real-time inputs circuit, such as determining oximetry reading values associated with the sheath coming out of contact with tissue. The averaging circuit can transmit the value for the measurement average, the value of the number of measurements in an average, one of these values, or both of these values to the display controller circuit.

Memory 415 can store information for a background screen for the display. The background screen information is sometimes referred to as splash screen information. The information for the background screen can include information for display elements displayed on the display that do not change except when the display is taken over for the display of other information, such as warning information regarding the system unit. The background screen information can include information that is generally static on the display when oximetry information is being displayed, when the system unit is ready to take a measurement and display oximetry information, and after the system unit has been inverted and the oximetry information generated by the system unit has been reset.

In an implementation, the information for the background screen includes the information for the text "avg of," "live," and "% StO2" for both the measurement average and the real-time oximetry measurements. In an implementation, the information for the background screen includes some or all of the portions for the black background of the display as shown in FIGS. 23-27. In an implementation, the information for the background screen includes some or all of the portions for the black background of the display as shown in FIGS. 23-27.

In an implementation, the information for the color inverted portions of the display are included in the information for the background screen. For example, the information for the color inverted portions of the background screen can include the portion (e.g., first white box portion) of the display in which the number of measurements in an average is displayed and the portion (e.g., second white box portion) of the background screen in which the measurement average is displayed.

The background screen can include the quality metric status indicator without any elements of the indicator highlighted to indicate the quality status. The quality metric status indicator is a template that is stored as a hex table in the memory. For example, the quality metric status indicator can be stored in a hex table of up to 6 rows of 0x0000 data before the first hex value appears. Any other portion of the background screen can similarly be stored in the form of one or more hex tables in the memory. A read performed on the memory by the physical inputs circuit or another circuit can retrieve information from the tables from the memory so that various portions of the background screen can be displayed on the display.

The background information can be transmitted to the display controller circuit by the physical input circuit 420. Alternatively, the background information can be transferred to the display controller circuit by other circuits of circuit 400.

In an implementation, the pixel location information of table E shown above is stored in the memory, such as in a hex table. The pixel information can be retrieved by the physical inputs circuit for transmission to the display controller. In another implementation, the display controller can access the memory to retrieve the background information including the pixel location information.

In an implementation, the physical inputs circuit 420 is coupled to other circuits that are included in the system unit, such as a timing circuit, an accelerometer circuit, an ambient light detector circuit, a microphone circuit, other circuits, or any one of these circuits, or one combination of these circuits. For example, the physical inputs circuit can be connected to the accelerometer circuit to collect information about the movement of the system unit, such as the detected inversion of the system unit. Information for an inversion of the system unit can be transmitted from the physical inputs circuit to the display controller circuit. Other physical information received by the physical inputs circuit can be transmitted from the physical inputs circuit to the display controller.

The display controller circuit 425 can be an ASIC circuit, a configuration circuit, a non-configurable circuit, or another type of circuit that is adapted to format collected information for transfer to the display for display. The display controller circuit can include a scaler circuit, be connected to a scaler circuit, or another circuit so that characters and graphics can be displayed at predetermined sizes on the display.

The display controller circuit can receive input values for scale information for scaling. The display controller circuit can be connected to a clock circuit so that information is transmitted from the display controller circuit to the display at a predetermined clock rate. The system unit can include a clock tree that adapts a clock signal from the clock circuit for use by the display controller, the display, and another circuit of the system unit.

The display controller circuit can include one or more memories to buffer collected information prior to transmission of the information to the display. The buffer memory can be a RAM or another memory type. Alternatively, the display controller circuit can be connected to an external memory (e.g., a RAM) that the display controller circuit accesses for use as a buffer memory.

The display controller circuit 425 is connected to the display. The display controller circuit can transmit collected information from the real-time inputs circuit, the averaging circuit, the physical inputs circuits, other circuits, or any combination of these circuits to the display controller circuit. The transmitted information can be transmitted in a format the display can receive for use for display on the display. The information can be transmitted through a serial port to the display. Alternatively, the information can be transmitted through a parallel port to the display. In an implementation, the display is configurable to operate a serial port or a parallel port to receive information from the display controller circuit.

The information for the background screen can be transferred from the display controller to the display. The background information may not need to be rewritten on the display unless the displayed information is replaced with other information that does not use the background, such as a warning that is displayed on the display. Transferring the background information to the display from the display control reduces the amount of information that has to be refreshed on the display when new information is displayed on the display. For example, information in the fields in which numerical values are displayed, the central field in which text information is displayed, the battery indicator, and the quality information display can be provided from the display controller circuit to the display independently from the information for the background screen and the display can update the displayed information for these fields independently from the background. Updating the information in the described fields allows for the information in these fields to be updated relatively quickly so that a user of the system unit is relatively quickly shown stable or changing oximetry information, which the system unit generates for a patient's tissue. The quick display of accurate oximetry information can aid in facilitating a successful surgery, for example, such as a tissue flap surgery for breast reconstruction, where accurate oximetry information can aid in the success of the surgery.

In an implementation, memory locations of memory 415 are mapped to pixels of display 307. Mapping memory locations of memory 415 to pixels of display 307 allow for the pixels to be efficiently used to display information in the mapped memory and not update the display of information displayed in other pixels of the display that are not mapped to the memory locations.

The memory location can include rows of the memory, columns of the memory, rows and columns of the memory, or other locations. In an implementation, the system unit includes the display, which is arranged in an array of pixels in rows and columns. The system unit 301 includes display controller circuit 425, which is coupled to display 307. The display controller circuit 425 can be a graphics processing unit (GPU) or another circuit type.

In an implementation, a first subset of the array of pixels of the display includes a number of first pixels arranged in first rows and first columns, where there are more first rows than first columns. A second subset of the array of pixels of the display includes a second number of second pixels arranged in second rows and second columns, where there are more second columns than second rows. A third subset of the array of pixels of the display includes a second number of third pixels arranged in third rows and third columns, where there are more third rows than third columns. Table E shows an example of the subsets of arrays of pixels where specific oximetry information is displayed on the display.

A pixel coordinate of an upper left corner of the first subset of the array of pixels plus the number of first rows includes a first range of rows of pixels. A pixel coordinate of an upper left corner of the second subset includes a row coordinate that is within the first range of rows of pixels. The display memory 415 is connected to the display controller circuit 425, wherein a first number of memory bits of the display memory map to the first subset of the array of pixels, a second number of memory bits map to the second subset of the array of pixels, and a third number of memory bits map to the third subset of the array of pixels. For example, the memory locations of the memory are mapped to locations to the pixels for the real-time StO2 values to the average number of measurements in an average, to the average over multiple measurements, to the quality metric indicator, to the battery indicator, and to the center field where use information (e.g., lift up) is displayed. Table E above shows an example map of the pixels for these values on the display.

In an implementation, the display includes an organic light emitting diode display. A row of the display includes n pixels and a column of the display includes n pixels, and n is an integer 16 or greater.

A pixel coordinate of an upper left corner of the first subset of the array of pixels plus the number of first columns includes a first range of columns of pixels. And, a pixel coordinate of an upper left corner of the third subset includes a column coordinate that is within the first range of column of pixels. A character font written to the first subset of the array of pixels is an inverse of the character font written to the second subset of the array of pixels. The third subset of the array of pixels displays a real-time value (e.g., a real-time oxygen saturation value) of an output of the system unit. The first subset of the array of pixels is configured to display the average of two or more real-time values (e.g., real-time oxygen saturation values) generated by the system unit. The first subset of the array of pixels displays the number of real-time values used to generate the average of the real-time values.

In an implementation, the display memory includes a fourth number of memory bits that maps to the pixels of the display. A coordinate of the upper left corner of the first subset of the array of pixels is also within the fourth number of the memory bits. And, a coordinate of upper left corner of the second subset of the array of pixels is also within the fourth number of the memory bits.

Figure 30:
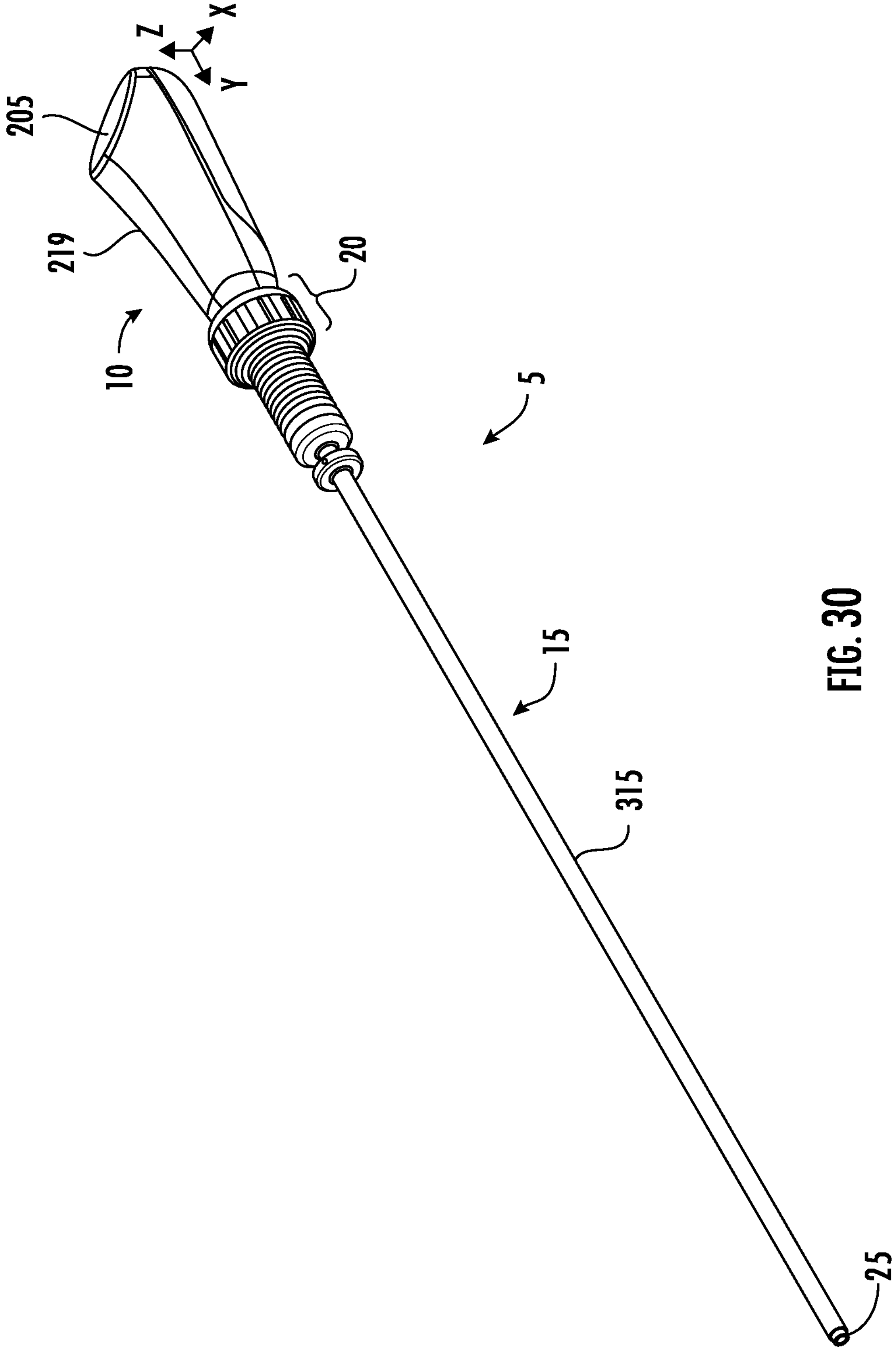
FIG. 30 shows a diagram of a laparoscopic oximeter, in an implementation.

FIG. 30 shows a diagram of a laparoscopic oximeter 5, in an implementation. The laparoscopic oximeter is a handheld device and is configured for use in laparoscopic surgeries for generating oximetry information, such as an oxygen saturation value, of tissue within the abdominal cavity of a patient.

Laparoscopic oximeter 5 includes a probe unit 10, a laparoscopic tube 15, and a number of connectors 20 that detachably connect the probe unit to the elongated tube. Connectors 20 can include one or more mechanical connectors, one or more optical connectors, one or more electrical connectors, or any of these types of connectors in any combination.

The laparoscopic tube 15 includes an elongated tube 315 that can be adapted to be inserted into an abdominal cavity of a patient via a trocar for interoperative surgery. The elongated tube 315 includes a sensor head 25 that is adapted to emit light (e.g., visible light, near infrared light, or both) into internal tissue and collected reflected light from the tissue based on the emitted light for making oximetry measurements of the internal tissue during the interoperative surgery. Laparoscopic oximeter 5 can be a tissue oximeter adapted to make tissue oximetry measurements or a pulse oximeter adapted to make pulse oximetry measurements.

An outside surface of the laparoscopic tube can be smooth so that the laparoscopic tube can slide through the trocar smoothly, can rotate within the trocar smoothly, and can slide into contact and past patient tissue smoothly and without abrading the tissue. The laparoscopic oximeter can be used on various internal tissue to determine various oximetry information for the tissue, such as oxygen saturation. Internal tissue under test can include intestinal tissue, such as the large intestine, small intestine, tissue that supports these tissues, such as the mesentery tissue, muscle, the liver, kidneys, stomach, gallbladder, pancreas, arteries, heart, lungs, veins, or other internal tissue.

The laparoscopic oximeter is fully self-contained and does not need to be connected to another device to be fully operational, in an implementation. That is, the laparoscopic oximeter does not need to be wire connected or wirelessly connected to another device to operate. In an implementation, the laparoscopic oximeter does connect to other devices, such as one or more other medical devices, a computer system, a display, these devices or systems, or other devices or systems.

In an implementation, connectors 20 facilitate the separation of the probe unit from the laparoscopic tube. For example, the probe unit and laparoscopic tube can be separated after the laparoscopic oximeter has been used for a laparoscopic surgery. The probe unit can be reused after the surgery and the laparoscopic tube can be discarded. The probe unit can be cleaned after the surgery and connected to a different laparoscopic tube to form another laparoscopic oximeter. The probe unit can thereafter be used in a different surgery. The probe unit is sometimes referred to as a durable unit because this unit is reusable, whereas the laparoscopic tube is sometimes referred to as a disposable unit because it is to be disposed of after use on a patient.

In an implementation, the laparoscopic oximeter (e.g., probe unit 10) includes the circuits shown in any one or a combination of FIGS. 4-7. The circuits of FIGS. 4-7 are relatively costly. Allowing for the probe unit to be reused allows for cost savings by the reuse. Allowing for the probe unit to be reused also allows for ecological advantages because the probe unit can be reused a number of times before the probe unit is disposed of.

In an implementation, the laparoscopic oximeter is configured to make average oximetry measurements as described above and display the average oximetry information on a display 205 of the laparoscopic oximeter as described with respect to FIGS. 12-21, FIGS. 24-30, and tables A-E. In a further implementation, the laparoscopic oximeter is configured to reset or erase one or more pieces of oximetry information, average oximetry information, and reset the display of the laparoscopic oximeter as described above. For example, the laparoscopic oximeter can reset or erase the number of measurements in average 3110, the average over multiple measurements 3105, the real-time StO2 3100, and reset the display of these values on the display of the laparoscopic oximeter. For example, information used for generating average oximetry information or an average oximetry value is erased from memory of the laparoscopic oximeter, such as memory 312, 315, one of these memories, or both of these memories and is removed from the display. In an implementation, these values used for generating an average oximetry measurement value and the measurement value can be erased from the accelerometer 332 detecting one or more of a variety of movements that the laparoscopic oximeter experiences. A method for resetting information used for generating average oximetry information, erasing information used for generating average oximetry information, or both is described further below. It will be understood that in one implementation, erasing values from the memory includes allowing the values to be overwritten with subsequently generated values.

Figure 31:
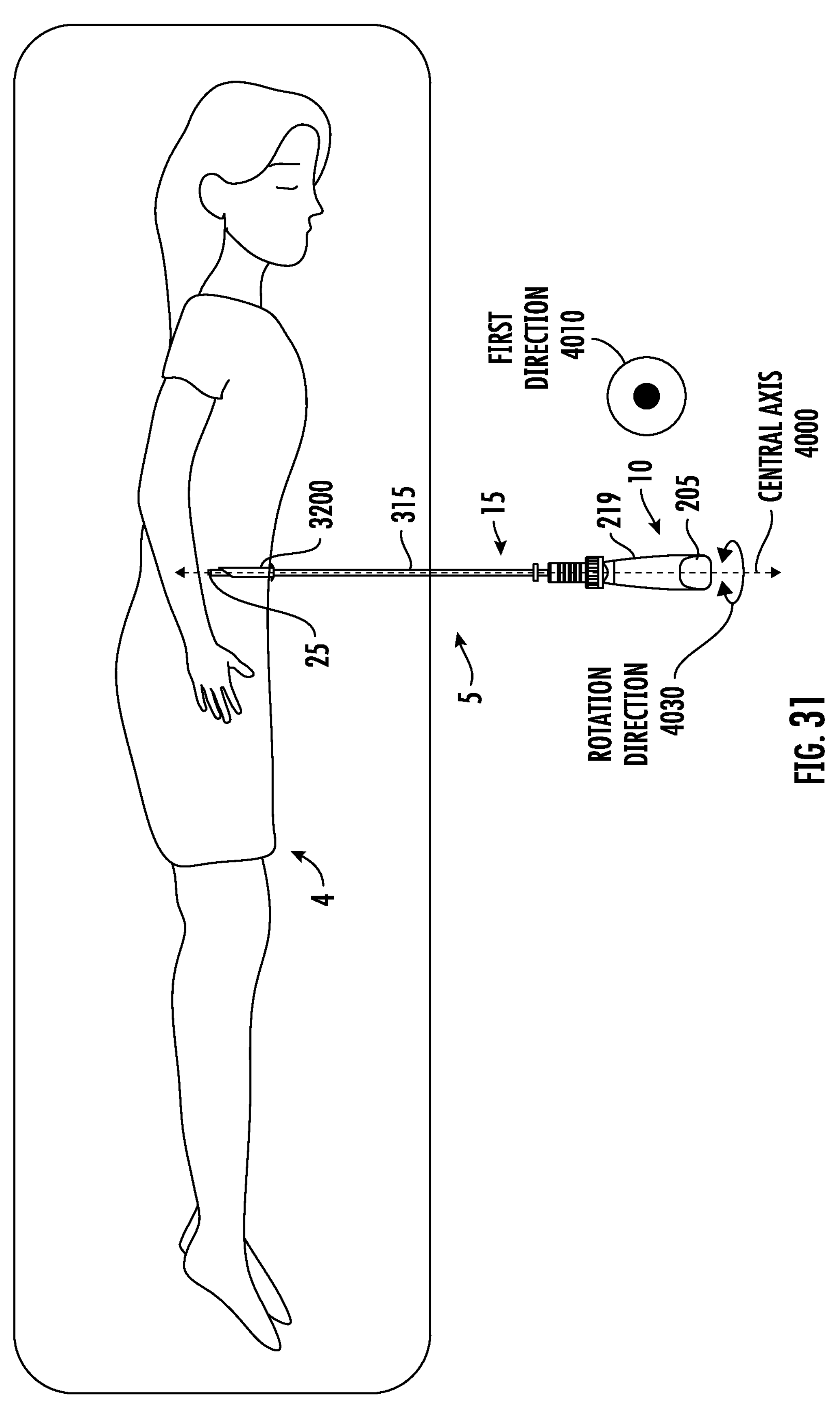
FIGS. 31-32 show a portion of the tube element of the laparoscopic oximeter inserted in the abdomen of a patient lying on their side through a trocar and show a time-ordered sequence of events.
Figure 32:
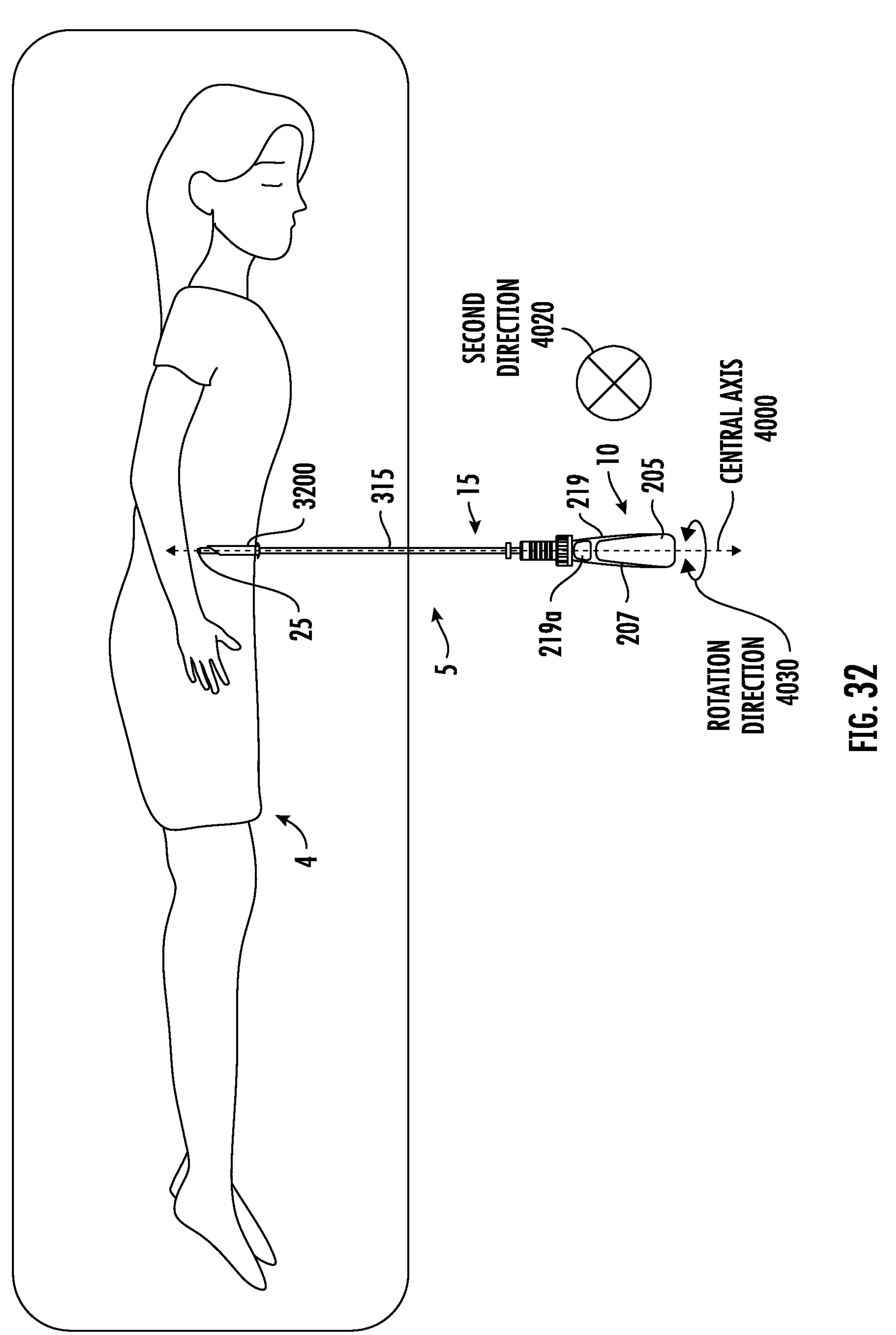

FIGS. 31-32 show a portion of tube element 315 of laparoscopic oximeter 5 inserted in the abdomen of a patient 4 through a trocar 3200 and show a time-ordered sequence of events. The patient is shown lying on their side in the figures. FIG. 31 shows the laparoscopic oximeter at a first time. The laparoscopic oximeter at the first time is oriented in a first rotational direction (e.g., display 205 facing upward) indicated by axis 4010, which is pointing out of the plane of the page. The upward direction out of the plane of the page is indicated by a circle with a dot inside of the circle (e.g., diagram of an arrow pointing out of the page). FIG. 32 shows the laparoscopic oximeter at a second time. The laparoscopic oximeter at the second time is oriented in a second rotational direction (e.g., display 205 pointing downward and not shown in FIG. 32, battery compartment 207 facing up, and finger rest 291*a* facing up) indicated by axis 4020 pointing into the plane of the page. The downward direction into the plane of the page is indicated by a circle with a cross inside of the circle (e.g., diagram of an arrow pointing into the page). The first time can be before the second time. The central axis 4000 of the laparoscopic oximeter can be approximately perpendicular to the direction of the acceleration of gravity vector (e.g., parallel to the floor of the operating room in which the patient is located).

The laparoscopic oximeter can be rotated (indicated by arrow 4030) about central axis 4000 by a user while a portion of laparoscopic element 315 is located in the trocar and in the patient's abdomen. For example, the laparoscopic oximeter can be rotated from the display up orientation of FIG. 31 to the display down orientation of FIG. 32.

Rotation of the laparoscopic oximeter about axis 4000 through a predetermined number of degrees initiates the laparoscopic oximeter to perform the reset and erasure of values described above for generating an average oximetry value and resetting the display as described above. The number of degrees of rotation about axis 4000 can be about 90-160 degrees to affect the resets, erasures, or both.

In an implementation, accelerometer 332 detects the rotation of the laparoscopic oximeter about central axis 4000. Accelerometer 332 can be a two axes accelerometer, a three axes accelerometer, or two two-axes accelerometers. The accelerometer can be mounted in the laparoscopic oximeter (e.g., on a PCB) so that the accelerometer can detect rotation about central axis 4000. In various implementations, the accelerometer can detect rotation about one, two, or three axes of rotation or any combination of these axes of rotation. In an implementation, the accelerometer can detect the rotation of the laparoscopic oximeter with respect to the vector for the acceleration of gravity. The accelerometer can detect a change in the rotational direction about axis 4000 with respect to the acceleration of gravity vector. In an implementation, the average information is reset by an impulse motion applied to the laparoscopic oximeter. The impulse motion can be applied, for example, when the laparoscopic oximeter is outside of the abdominal cavity of a patient.

The accelerometer, the processor, or both can implement hysteresis so that the laparoscopic oximeter does not reset the averaging information and measurements when not intended. The laparoscopic oximeter can implement the hysteresis described above with respect to FIG. 21, where the rotations are horizontal about axis 4000 rather than vertical as described with respect to system unit 305.

For example, the laparoscopic oximeter can be rotated about axis 4000 by about 90 degrees to about 160 degrees (e.g., solid line in FIG. 21) from the orientation of the laparoscopic oximeter shown in FIG. 31 to the orientation of the oximeter shown in FIG. 32 for the averaging information to reset including the information displayed on the display. In an embodiment, the rotation about axis 4000 is 135 degrees for the averaging information to reset. The laparoscopic oximeter can thereafter be returned from the rotated orientation (e.g., FIG. 32 orientation) to the unrotated orientation (e.g., FIG. 31 orientation). The laparoscopic oximeter will not be able to perform another reset of the averaging information until the rotational orientation of the laparoscopic oximeter is returned to about 45 degrees or less (e.g., the dashed line shown in FIG. 21) from the unrotated orientation shown in FIG. 31 from the rotated orientation shown in FIG. 32.

Additionally, the accelerometer of the laparoscopic oximeter may not be configured to determine whether the oximeter is oriented in the first orientation of FIG. 31 with the display upward or oriented down in the second orientation of FIG. 32. That is, by configuring the laparoscopic oximeter detect the laparoscopic oximeter being rotated about axis 4000 by the first angle (e.g., solid line of FIG. 21) and being unrotated at the second angle (e.g., dashed line of FIG. 21), the laparoscopic oximeter unit can use motion detection detected by the accelerometer and the hysteresis to determine whether the laparoscopic oximeter is being rotated from the first orientation of FIG. 31 (e.g., display up) to the second orientation of FIG. 32 (e.g., display down).

Figure 33:
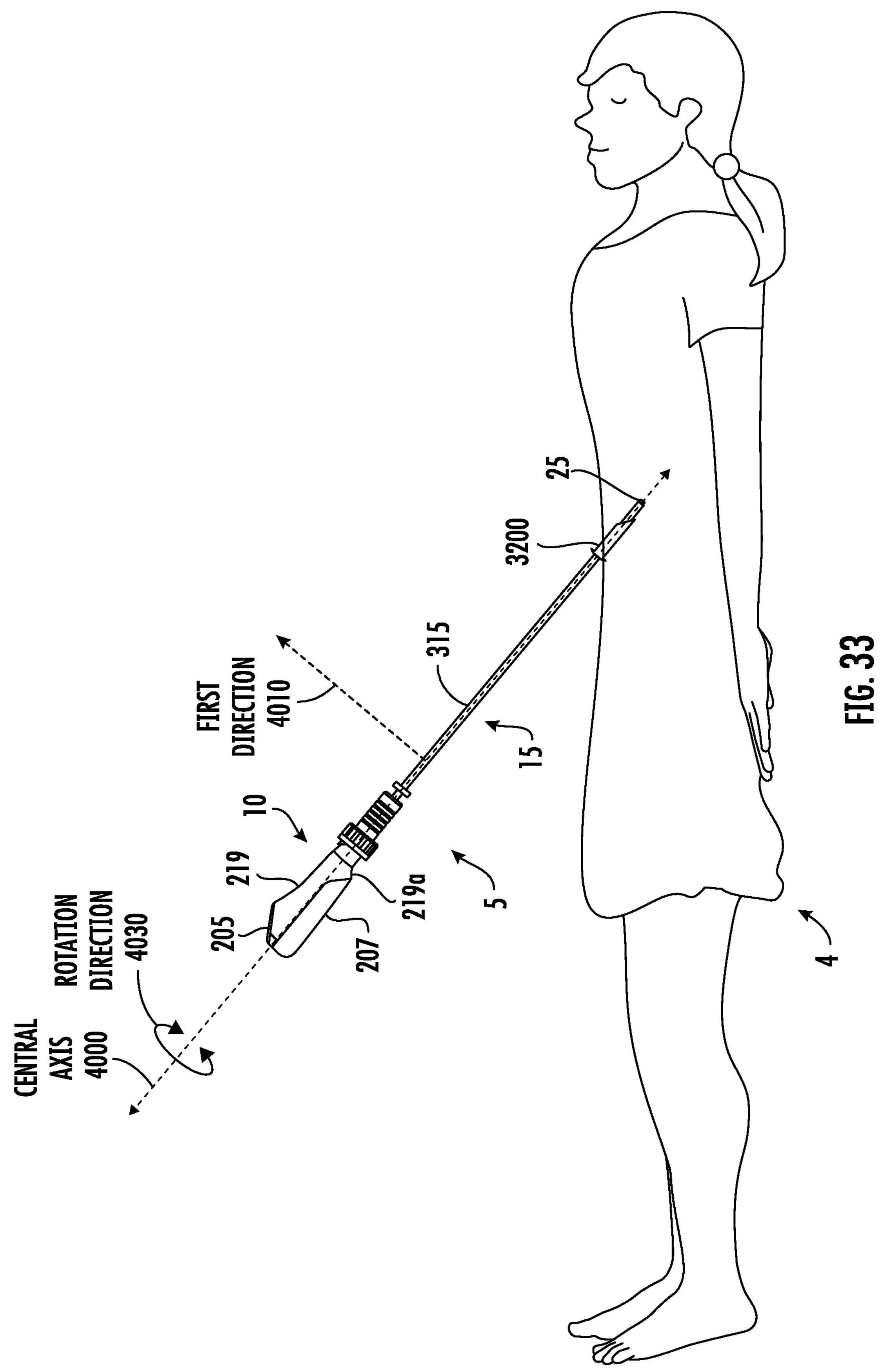
FIGS. 33-34 show a portion of a tube element of the laparoscopic oximeter inserted in the abdomen of a patient lying on their back through a trocar and show a time-ordered sequence of events.
Figure 34:
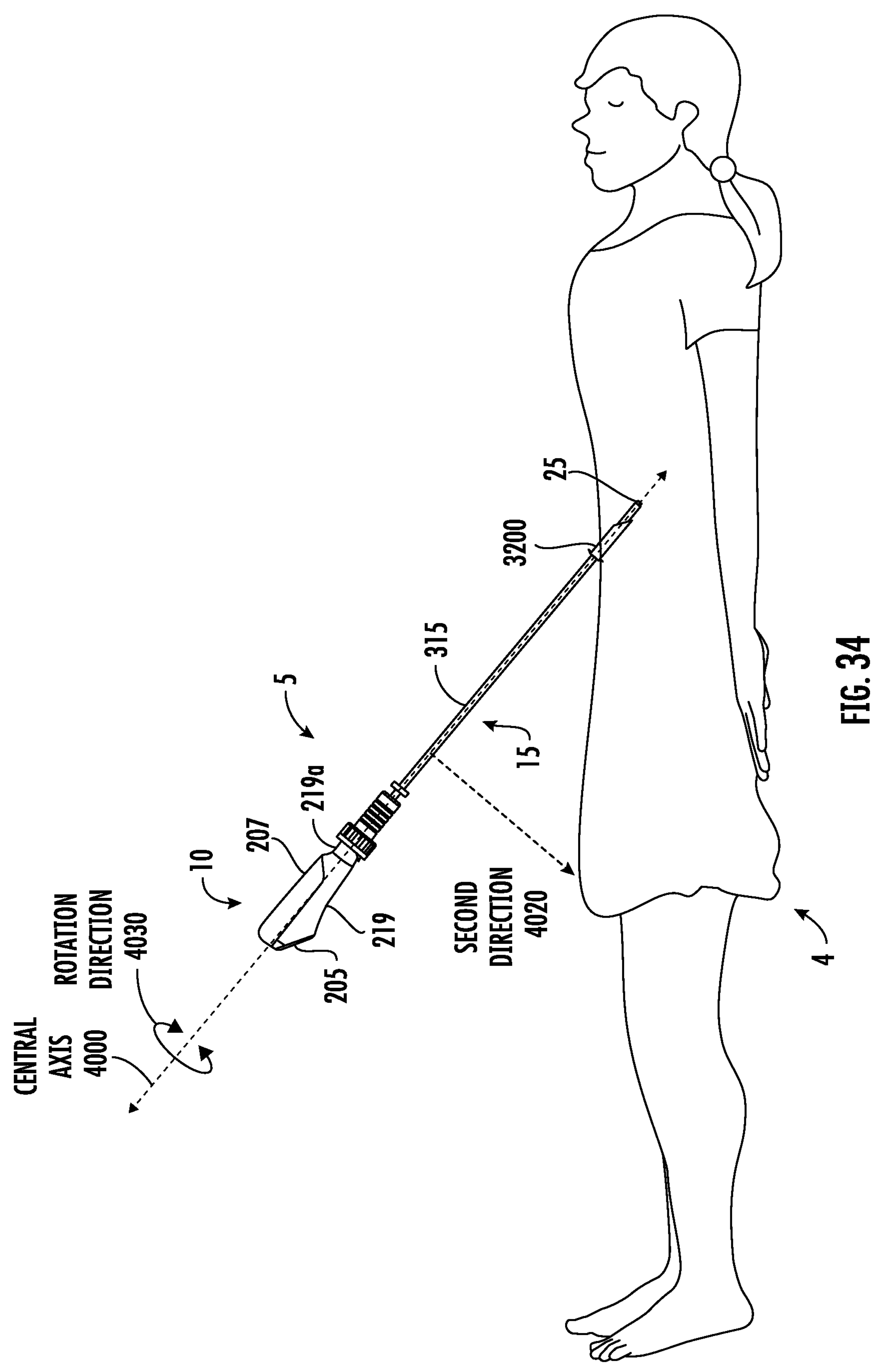

FIGS. 33-34 show a portion of tube element 315 of laparoscopic oximeter 5 inserted in the abdomen of a patient 4 through a trocar 3200 and show a time-ordered sequence of events. The patient 4 is lying on their back and the acceleration of gravity vector is downward in the plane of the drawing page. FIG. 33 shows the laparoscopic oximeter at a first time oriented in a first rotational direction (e.g., display 205 facing upward) indicated by axis 4010. FIG. 34 shows the laparoscopic oximeter at a second time oriented in a second rotational direction (e.g., display 205 pointing downward) indicated by axis 4020. The first time can be before the second time. The central axis 4000 of the laparoscopic oximeter can be angled with respect to the direction of gravity from about 0 degrees (parallel to the direction of gravity) to about 90 degrees (perpendicular to the direction of gravity). The laparoscopic oximeter can be rotated (indicated by arrow 4030) about central axis 4000 by a user while a portion of laparoscopic element 315 is located in the trocar and in the patient's abdomen for the laparoscopic oximeter to reset the average oximetry information, the real time oximetry information, and the displayed values. For example, the laparoscopic oximeter can be rotated from the display up orientation of FIG. 33 to the display down orientation of FIG. 32 to reset the average oximetry information, the real time oximetry information, and the displayed values.

Rotation of the laparoscopic oximeter about axis 4000 through a first predetermined number of degrees initiates the laparoscopic oximeter to perform the reset and erasure of values described above for generating an average oximetry value and resetting the display as described above. The number of degrees of rotation about axis 4000 can be about 100-160 degrees (e.g., about 135 degrees and represented by the solid line in the hysteresis graph shown in FIG. 21) to affect the reset and erasures. The laparoscopic oximeter can be rotated back to its approximate original orientation without performing a second reset due to the described hysteresis according to which the laparoscopic oximeter operates. The angle at which the laparoscopic oximeter is able to perform a second reset is a second predetermined number of degrees that is less than the first predetermined number of degrees. The second predetermined number of degrees may be about 90 degrees or less (e.g., represented by the dashed line in the hysteresis graph shown in FIG. 21).

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

The invention claimed is:

1. An oximetry device comprising:

a housing;

a processor housed by the housing;

a memory, housed by the housing, coupled to the processor;

a display, housed by the housing and visible from an exterior of the housing, coupled to the processor; and a sensor head, housed by the housing and visible from an exterior of the housing, comprising at least a first source structure and at least a first detector structure, wherein the processor controls the at least first source structure and the at least first detector structure of the sensor head to make a number n of optical oximetry measurements of tissue to be measured, wherein when the n measurement is greater or less than a threshold amount, the processor controls storage of a value for the n−1 measurement in the memory and storage of a value of one in the memory, after the n optical oximetry measurements of the tissue are measured, the processor controls the at least first source structure and the at least first detector structure of the sensor head to make a number m of optical oximetry measurements of the tissue to be measured, wherein when a value for the m measurement is greater or less than the threshold amount, the processor controls storage of a value for a first sum of the value for the n−1 measurement and an m−1 value for the m−1 measurement in the memory and storage of a value of two in the memory, and after the m optical oximetry measurements of the tissue are measured, the processor generates a first average value for the first sum divided by the stored value two and controls the display to display the first average value.

2. The device of claim 1 wherein after the m optical oximetry measurements of the tissue are measured, the processor controls the at least first source structure and the at least first detector structure of the sensor head to make a number p optical oximetry measurements of the tissue to be measured, wherein when a value of the p measurement is greater or less than the threshold amount, the processor controls storage of a value for a second sum of the first sum and a p−1 value for the p−1 measurement in the memory and storage of a value of three in the memory, and after the p optical oximetry measurements of the tissue are measured, the processor generates a second average value for the second sum divided by the stored value three and controls the display to display the second average value.

3. The device of claim 2 wherein after the p optical oximetry measurements of the tissue are measured, the processor controls the at least first source structure and the at least first detector structure of the sensor head to make a number q optical oximetry measurements of the tissue to be measured, wherein when a q value for the q measurement is greater or less than the threshold amount, the processor controls storage of a value for a third sum of the second sum and a q−1 value for the q−1 measurement in the memory and storage of a value of four in the memory, and after the q optical oximetry measurements of the tissue are measured, the processor generates a third average value for the third sum divided by the stored value four and controls the display to display the third average value.

4. The device of claim 1 comprising an accelerometer, housed by the housing, coupled to the processor, wherein the accelerometer is adapted to detect rotation of the housing with respect to a direction of the acceleration of gravity by a predetermined number of degrees, wherein the processor controls the at least first source structure and the at least first detector structure of the sensor head to make a number p of optical oximetry measurements of tissue to be measured, wherein when a value for the p measurement is greater or less than the threshold amount, the processor controls storage of a value for the p−1 measurement in the memory and storage of a value of one in the memory, after the p optical oximetry measurements of the tissue are measured, the processor controls the at least first source structure and the at least first detector structure of the sensor head to make a number q of optical oximetry measurements of the tissue to be measured, wherein when a value for the q measurement is greater or less than the threshold amount, the processor controls storage of a value for a second sum of the p−1 value and the q−1 value in the memory and storage of a value of two in the memory, and after the q optical oximetry measurements of the tissue are measured, the processor generates a second average value for the second sum divided by the stored value two and controls the display to display the second average value.

5. An oximetry device comprising:

a housing;

a processor housed by the housing;

a memory, housed by the housing, coupled to the processor;

a display, housed by the housing and visible from an exterior of the housing, coupled to the processor; and a sensor head, housed by the housing and visible from an exterior of the housing, comprising at least a first source structure and at least a first detector structure, wherein when the sensor head contacts a first tissue of a patient, the processor controls the oximetry device to make a plurality of first oximetry readings of the first tissue using the sensor head, when the sensor head is removed from contact with the first tissue of the patient, the processor detects the sensor head being removed from contact from the first tissue and stores a value in the memory of one of the first oximetry readings, when the sensor head of the oximetry device contacts a second tissue of the patient, the processor controls the oximetry device to make a plurality of second oximetry readings of the second tissue, when the sensor head of the oximetry device is removed from contact from the second tissue, the processor detects the sensor head being removed from contact from the second tissue and retrieves from the memory the one of the first oximetry readings, the processor generates an average of the value for the one of the first oximetry reading and a value for one of the second oximetry readings based on the device detecting being removed from contact from the second tissue, and the processor controls the display to display the value for the average.

6. The device of claim 5 wherein the first and second tissues are different tissue of the patient.

7. The device of claim 5 wherein the first and second tissues are the same tissue of the patient.

8. The device of claim 5 wherein the stored value is a value for a second to last one of the first oximetry readings taken by the oximetry device prior to the device unit being removed from contact from the first tissue.

9. The device of claim 5 wherein the value for the one of the second oximetry readings is a value for a second to last one of the second oximetry readings taken by the oximetry device prior to the device unit being removed from contact from the second tissue.

10. The device of claim 5 wherein the oximetry device is a tissue oximeter.

11. The device of claim 10 wherein the oximetry device is a laparoscopic oximeter.

12. The device of claim 10 wherein when the oximetry device is rotated about a horizontal axis by a predetermined number of degrees, the processor controls the oximetry device to start a first new averaging of oximetry readings.

13. The device of claim 12 wherein when the oximetry device is rotated about a horizontal axis by a predetermined number of degrees, the processor removes oximetry information displayed on the display.

14. The device of claim 12 wherein when the oximetry device is rotated within a predetermined second number of degrees from the first number of degrees after the oximetry device is rotated by the first number of degrees, the processor controls the oximetry device to prevent a start of a second new averaging.

15. The device of claim 1 comprising the processor not storing values for the n and m optical oximetry measurements.

16. The device of claim 15 comprising the processor not including the values for the n and m optical oximetry measurements in the first average value.

17. The device of claim 15 comprising after the n optical oximetry measurement is made by the oximeter device, the processor controls storage of the value for the n−1 optical oximetry measurement for generation of the first average value.

18. The device of claim 15 comprising after the m optical oximetry measurement is made by the oximeter device, the processor controls storage of the value for the m−1 optical oximetry measurement for generation of the first average value.

* * * * *